US008709999B2

(12) United States Patent
Zhong et al.

(10) Patent No.: US 8,709,999 B2
(45) Date of Patent: Apr. 29, 2014

(54) SUBSTITUTED BICYCLIC HCV INHIBITORS

(75) Inventors: Min Zhong, Palo Alto, CA (US); Leping Li, Burlingame, CA (US)

(73) Assignee: Presidio Pharmaceuticals, Inc., San Francisco, CA (US)

( * ) Notice: Subject to any disclaimer, the term of this patent is extended or adjusted under 35 U.S.C. 154(b) by 232 days.

(21) Appl. No.: 13/260,334

(22) PCT Filed: Mar. 26, 2010

(86) PCT No.: PCT/US2010/028950
§ 371 (c)(1),
(2), (4) Date: Sep. 25, 2011

(87) PCT Pub. No.: WO2010/111673
PCT Pub. Date: Sep. 30, 2010

(65) Prior Publication Data
US 2012/0028978 A1 Feb. 2, 2012

Related U.S. Application Data

(60) Provisional application No. 61/163,865, filed on Mar. 27, 2009.

(51) Int. Cl.
*A61K 38/00* (2006.01)
*A01N 37/18* (2006.01)

(52) U.S. Cl.
USPC .......................................... 514/3.7; 514/4.3

(58) Field of Classification Search
None
See application file for complete search history.

(56) References Cited

U.S. PATENT DOCUMENTS

| 5,527,808 | A | 6/1996 | Lowe, III et al. |
| 6,255,483 | B1 | 7/2001 | Fletcher et al. |
| 8,088,368 | B2 | 1/2012 | Guo et al. |
| 8,101,643 | B2 * | 1/2012 | Qiu et al. .................. 514/394 |
| 2007/0299050 | A1 | 12/2007 | Lal et al. |
| 2008/0044380 | A1 | 2/2008 | Bachand et al. |
| 2010/0226882 | A1 | 9/2010 | Or et al. |
| 2011/0064695 | A1 | 3/2011 | Qiu et al. |

FOREIGN PATENT DOCUMENTS

| WO | WO 2007/019937 A1 | 2/2007 |
| WO | WO 2008/021927 A2 | 2/2008 |
| WO | WO 2008/021928 A2 | 2/2008 |
| WO | WO 2008/021936 A2 | 2/2008 |
| WO | WO 2010/065668 A1 | 6/2010 |
| WO | WO 2010/065674 A1 | 6/2010 |
| WO | WO 2010/065681 A1 | 6/2010 |

OTHER PUBLICATIONS

PCT International Search Report and Written Opinion of the International Searching Authority, PCT/US2010/028950, May 12, 2010, 11 Pages.
Albert, A. et al., "275. Benzylamine Analogues of Chemotherapeutic Diamidines," Journal of the Chemical Society (Resumed), 1947, p. 1452-1455.
European Extended Search Report, European Application No. 10756966.7, Sep. 21, 2012, 5 pages.
Koyama, K. et al., "Free Radical Reactions in Organic Electrode Processes—III," Tetrahedron, 1967, pp. 2665-2674, vol. 23.
Shelton, J.R. et al., "Reactions of Free Radicals of Olefins. Dehydro Dimer Structures of 4-Vinylcyclohexene," The Journal of Organic Chemistry, 1966, pp. 2028-2030, vol. 31.
Sindelar, K. et al., "Potential Antidepressants. Synthesis of 6, 11-Dihydrodibenzo[b,e]thiepin-11-yl4-(Dimethylaminomethyl)phenyl Ketone and of Some Related Compounds," Journal of Heterocyclic Chemistry, 1989, pp. 1325-1330, vol. 26.
Xing, B. et al., "Multivalent Antibiotics Via Metal Complexes: Potent Divalent Vancomycins Against Vancomycin-Resistant *Enterococci*," Journal of Medicinal Chemistry, 2003, pp. 4904-4909, vol. 46.
Ziyaev, A. A. et al., "Dimerization of N-Methylanabasine in the Presence of Raney Nickel," Chemistry of Heterocyclic Compounds, Sep. 1978, pp. 988-989, vol. 14, No. 9.

\* cited by examiner

*Primary Examiner* — Thomas Heard
(74) *Attorney, Agent, or Firm* — Fenwick & West LLP

(57) ABSTRACT

Provided herein are compounds, pharmaceutical compositions and combination therapies for treatment of hepatitis C.

17 Claims, No Drawings

SUBSTITUTED BICYCLIC HCV INHIBITORS

STATEMENT OF RELATED APPLICATIONS

This application is the U.S. national phase of PCT/US2010/028950 and claims the benefit of U.S. provisional application 61/163,865 filed Mar. 27, 2009, both of which are hereby incorporated by reference in their entirety for all purposes.

FIELD OF THE INVENTION

The invention relates to compounds useful for inhibiting the non-structural 5A ("NS5A") protein of hepatitis C virus ("HCV").

BACKGROUND OF THE INVENTION

HCV is a single-stranded RNA virus that is a member of the Flaviviridae family. The virus shows extensive genetic heterogeneity as there are currently seven identified genotypes and more than 50 identified subtypes. In HCV infected cells, viral RNA is translated into a polyprotein that is cleaved into ten individual proteins. At the amino terminus are structural proteins: the core (C) protein and the envelope glycoproteins, E1 and E2, and p7, an integral membrane protein that follows E1 and E2. Additionally, there are six non-structural proteins, NS2, NS3, NS4A, NS4B, NS5A and NS5B, which play a functional role in the HCV lifecycle. (see, for example, Lindenbach, B. D. and Rice, C. M. *Nature*. 436:933-938, 2005).

Infection by HCV is a serious health issue. It is estimated that 170 million people worldwide are chronically infected with HCV. HCV infection can lead to chronic hepatitis, cirrhosis, liver failure and hepatocellular carcinoma. Chronic HCV infection is thus a major worldwide cause of liver-related premature mortality.

The present standard of care treatment regimen for HCV infection involves interferon-alpha, alone or in combination with ribavirin. The treatment is cumbersome and sometimes has debilitating and severe side effects and many patients do not durably respond to treatment. New and effective methods of treating HCV infection are urgently needed.

SUMMARY OF THE INVENTION

Essential features of the NS5A protein of HCV make it an ideal target for inhibitors. The present disclosure describes a class of compounds targeting the NS5A protein and methods of their use to treat HCV infection in humans.

In a first aspect of the invention, compounds of formula I are provided:

I

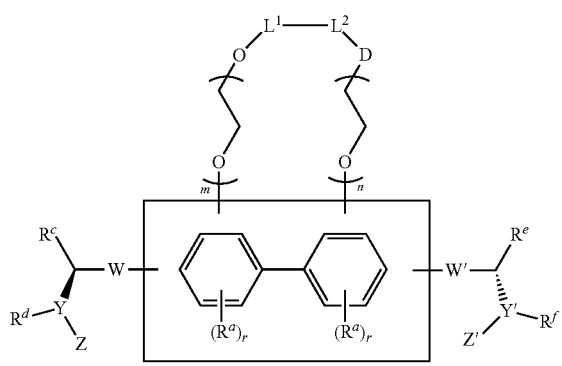

wherein:

$L^1$ and $L^2$ are either linked or not linked, when not linked, $L^1$ and $L^2$ are independently H or lower alkyl (containing 1 to 4 carbons) moieties;

when linked, $L^1$-$L^2$ are independently —$CH_2C(O)$—, —$C(O)$—, —$(CH_2CH_2$—O—$CH_2CH_2)_p$— wherein p is independently 1, 2 or 3, or lower alkyl (containing 1 to 4 carbons) moieties;

D is a bond, $CH_2$, NH, O, or S;

m and n are independently 0, 1, 2, 3 or 4 and m and n may not be both 0;

each $R^a$ is independently selected from the group consisting of —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

W and W' are each independently selected from the group consisting of

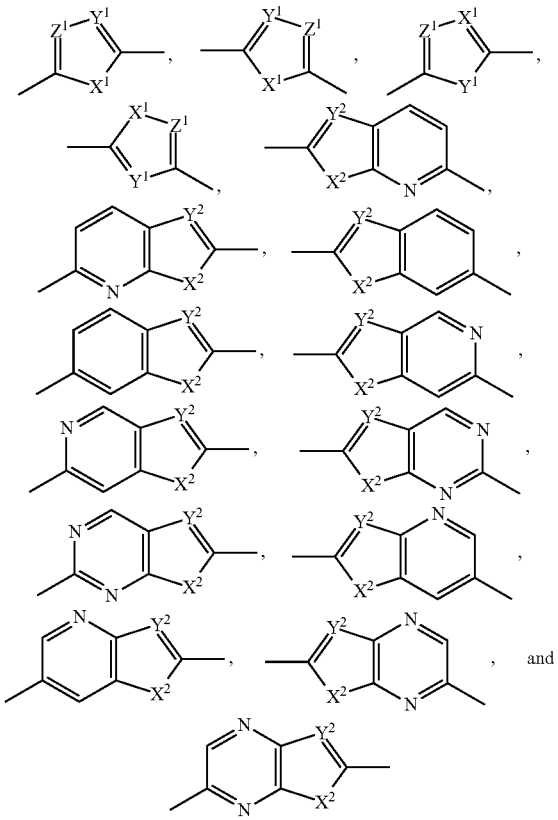

wherein:

$X^1$ is $CH_2$, NH, O or S, $Y^1$, $Y^2$ and $Z^1$ are each independently CH or N, $X^2$ is NH, O or S, W and W' are each independently optionally substituted with one or more substituents selected from the group consisting of —CN, —$NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and W and W' attached to the central biphenyl moiety can have the following substitution patterns:

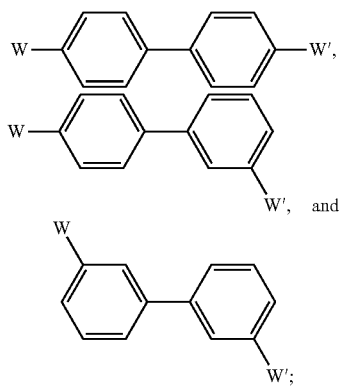

wherein, the biphenyl moiety may contain with 0-4 nitrogen atom(s); and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, $-[U-(CR^4{}_2)_t-NR^5-C(R^4{}_2)_t]_u-U-(CR^4{}_2)_t-NR^7-(CR^4{}_2)_t-R^8$, $-U-(CR^4{}_2)_t-R^8$, and $-[U-(CR^4{}_2)_t-NR^5-(CR^4{}_2)_t]_u-U-(CR^4{}_2)_t-O-(CR^4{}_2)_t-R^8$, wherein, U is selected from the group consisting of $-C(O)-$, $-C(S)-$ and $-S(O)_2-$, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, $-C(O)-R^{81}$, $-C(S)-R^{81}$, $-C(O)-O-R^{81}$, $-C(O)-N-R^{81}{}_2$, $-S(O)_2-R^{81}$ and $-S(O)_2-N-R^{81}{}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the first aspect, one or both of W and W' are selected from the group consisting of

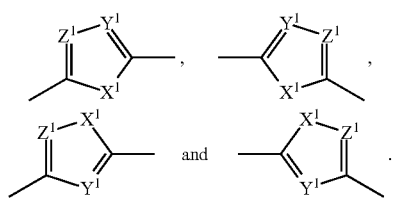

In a second embodiment of the first aspect, one or both of W and W' are selected from the group consisting of

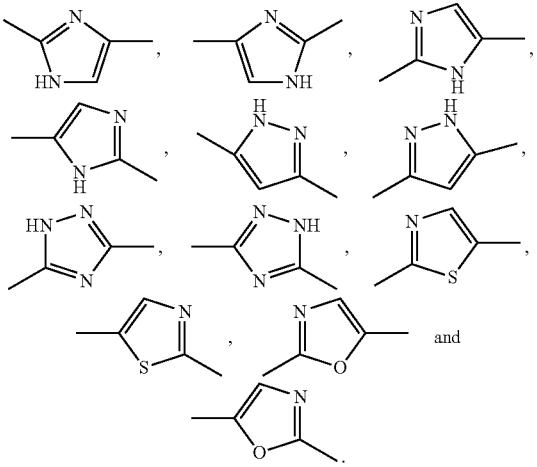

In a third embodiment of the first aspect, $R^c$, $R^d$, $R^e$ and $R^f$ are each independently selected from the group consisting of: hydrogen, $C_1$ to $C_8$ alkyl and $C_1$ to $C_8$ heteroalkyl, wherein, each hetero atom, if present, is independently N, O or S, $R^c$ and $R^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In a fourth embodiment of the first aspect, one or both of $R^c$ and $R^d$ or $R^e$ and $R^f$ are optionally joined to form a 4- to 8-membered heterocycle which is optionally fused to another 3- to 6-membered heterocycle.

In a fifth embodiment of the first aspect, $R^c$ and $R^d$ are joined and form a heterocyclic fused ring system selected from the group consisting of:

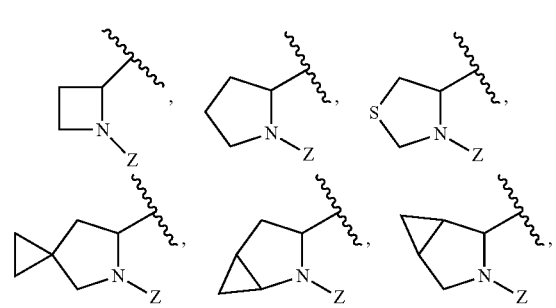

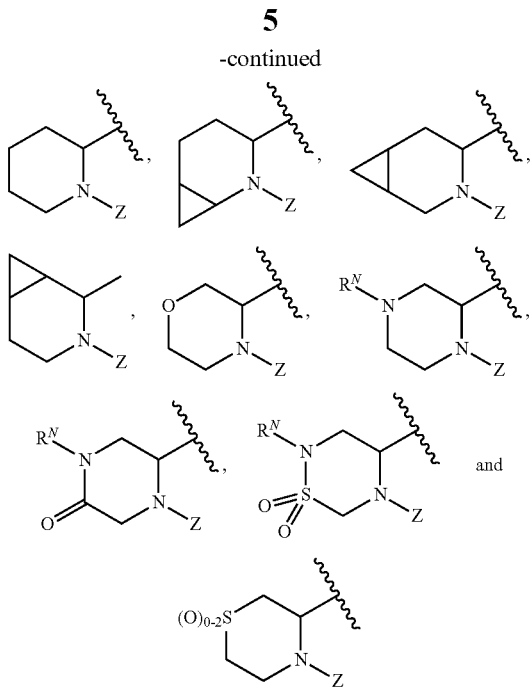

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment of the first aspect, $R^e$ and $R^f$ are joined and form a heterocyclic fused ring system selected from the group consisting of:

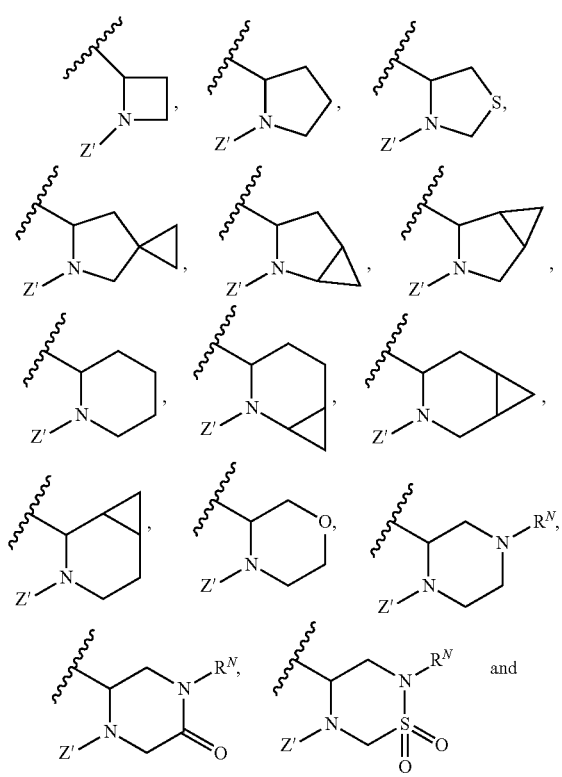

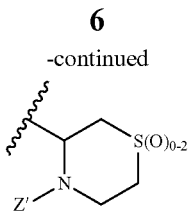

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula II:

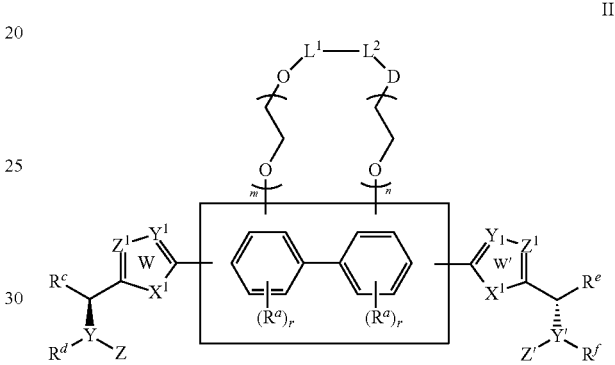

II wherein:

$L^1$ and $L^2$ are either linked or not linked, when not linked, $L^1$ and $L^2$ are independently H or lower alkyl (containing 1 to 4 carbons) moieties;

when linked, $L^1$-$L^2$ are independently —CH$_2$C(O)—, —C(O)—, —(CH$_2$CH$_2$—O—CH$_2$CH$_2$)$_p$— wherein p is independently 1, 2 or 3, or lower alkyl (containing 1 to 4 carbons) moieties;

D is a bond, CH$_2$, NH, O, or S;

m and n are independently 0, 1, 2, 3 or 4 and m and n may not be both 0;

each $R^a$ is independently selected from the group consisting of —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is CH$_2$, NH, O or S, $Y^1$, $Y^2$ and $Z^1$ are each independently CH or N, $X^2$ is NH, O or S, W and W' are each independently optionally substituted with one or more substituents selected from the group consisting of —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and W and W' attached to the central biphenyl moiety can have the following substitution patterns:

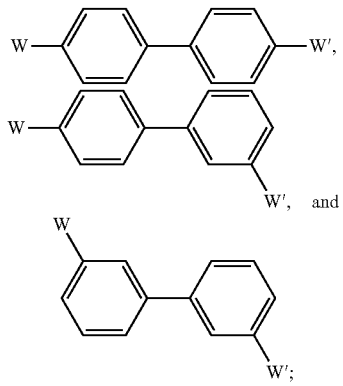

wherein, the biphenyl moiety can be substituted with 0-4 nitrogen atom(s); and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, $-[U-(CR^4_2)_t-NR^5-C(R^4_2)_t]_u-U-(CR^4_2)_t-NR^7-(CR^4_2)_t-R^8$, $-U-(CR^4_2)_t-R^8$, and $-[U-(CR^4_2)_t-NR^5-(CR^4_2)_t]_u-U-(CR^4_2)_t-O-(CR^4_2)_t-R^8$, wherein, U is selected from the group consisting of $-C(O)-$, $-C(S)-$ and $-S(O)_2-$, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, $-C(O)-R^{81}$, $-C(S)-R^{81}$, $-C(O)-O-R^{81}$, $-C(O)-N-R^{81}_2$, $-S(O)_2-R^{81}$ and $-S(O)_2-N-R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and
u is 0, 1, or 2.

In a third aspect of the invention, compounds have formula III:

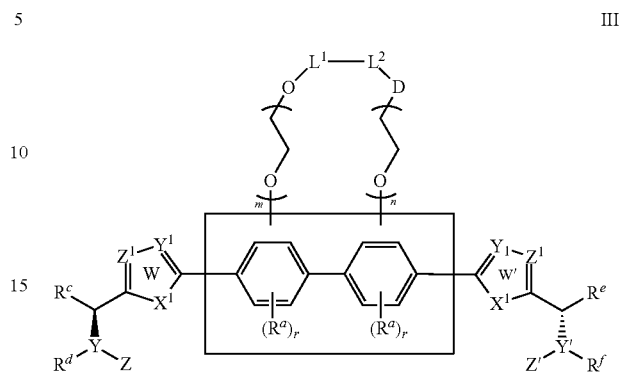

wherein:

$L^1$ and $L^2$ are either linked or not linked, when not linked, $L^1$ and $L^2$ are independently H or lower alkyl (containing 1 to 4 carbons) moieties;

when linked, $L^1$-$L^2$ are independently $-CH_2C(O)-$, $-C(O)-$, $-(CH_2CH_2-O-CH_2CH_2)_p-$ wherein p is independently 1, 2 or 3, or lower alkyl (containing 1 to 4 carbons) moieties;

D is a bond, $CH_2$, NH, O, or S;

m and n are independently 0, 1, 2, 3 or 4 and m and n may not be both 0;

each $R^a$ is independently selected from the group consisting of $-CN$, $-NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is $CH_2$, NH, O or S, $Y^1$, $Y^2$ and $Z^1$ are each independently CH or N, $X^2$ is NH, O or S, W and W' are each independently optionally substituted with one or more substituents selected from the group consisting of $-CN$, $-NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—$(CR^4_2)_t$—$NR^5$—$C(R^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$(CR^4_2)_t$—$R^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —S(O)$_2$—$R^{81}$ and —S(O)$_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the third aspect, compounds of formula IIIa are provided:

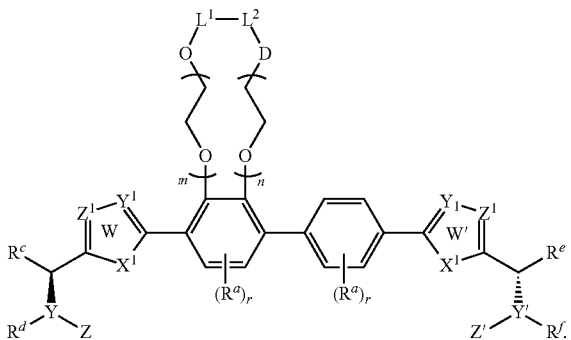

IIIa

In a second embodiment of the third aspect, compounds of formula IIIb are provided:

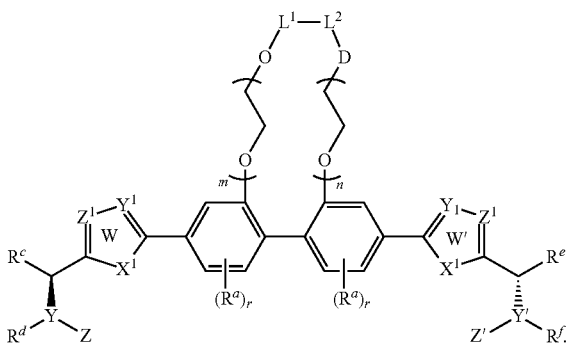

IIIb

In a third embodiment of the third aspect, compounds of formula IIIc are provided:

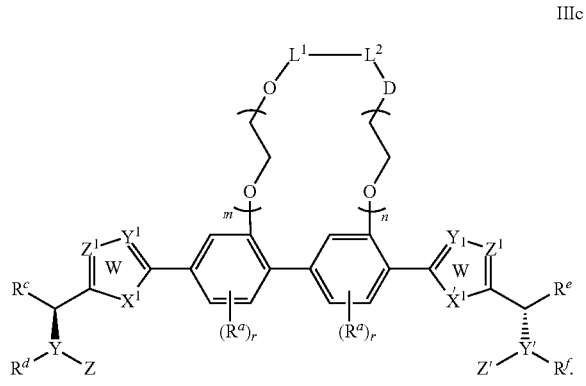

IIIc

In a fourth embodiment of the third aspect, compounds of formula IIId are provided:

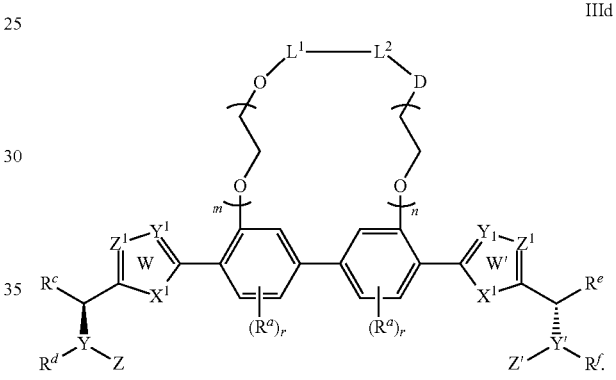

IIId

In a fifth embodiment of the third aspect, one or both of $X^1$ are —S—.

In a six embodiment of the third aspect, one or both of $X^1$ are —O—.

In a seventh embodiment of the third aspect, one or both of $X^1$ are —NH—.

In an eighth embodiment of the third aspect, one or both of $Z^1$ is —N—.

In a ninth embodiment of the third aspect, one or both of $Y^1$ is —N—.

In a fourth aspect of the invention, Z and Z' in any of the previous aspects are each 1-3 amino acids.

In a second embodiment of the fourth aspect, Z and Z' are each independently selected from the group consisting of —[U—$(CR^4_2)_t$—$NR^5$—$(CR^4_2)_t]_u$—U—$(CR^4_2)_t$—$NR^7$—$(CR^4_2)_t$—$R^8$, —U—$(CR^4_2)_t$—$R^8$ and —[U—$(CR^4_2)_t$—$NR^5$—$(CR^4_2)_t]_u$—U—$(CR^4_2)_t$—O—$(CR^4_2)_t$—$R^8$.

In a third embodiment of the fourth aspect, one or both of Z and Z' are —[U—$(CR^4_2)_t$—$NR^5$—$(CR^4_2)_t]_u$—U—$(CR^4_2)_t$—$NR^7$—$(CR^4_2)_t$—$R^8$.

In a fourth embodiment of the fourth aspect, one or both of Z and Z' are —U—$(CR^4_2)_t$—$NR^5$—$(CR^4_2)_t$—U—$(CR^4_2)_t$—$NR^7$—$(CR^4_2)_t$—$R^8$.

In a fifth embodiment of the fourth aspect, one or both of Z and Z' are —U—$(CR^4_2)_t$—$NR^7$—$(CR^4_2)_t$—$R^8$.

In a sixth embodiment of the fourth aspect, one or both of Z and Z' are —[C(O)—$(CR^4_2)_t$—$NR^5$—$(CR^4_2)_t]_u$—U—$(CR^4_2)_t$—$NR^7$—$(CR^4_2)_t$—$R^8$.

In a seventh embodiment of the fourth aspect, one or both of Z and Z' are —C(O)—(CR$^4_2$)$_t$—NR$^5$—(CR$^4_2$)$_t$—U—(CR$^4_2$)$_t$—NR$^7$—(CR$^4_2$)$_t$—R$^8$.

In an eighth embodiment of the fourth aspect, one or both of Z and Z' are —[C(O)—(CR$^4_2$)$_t$—NR$^5$—(CR$^4_2$)$_t$]$_u$—C(O)—(CR$^4_2$)$_t$—NR$^7$—(CR$^4_2$)$_t$—R$^8$.

In a ninth embodiment of the fourth aspect, one or both of Z and Z' are —C(O)—(CR$^4_2$)$_t$—NR$^5$—(CR$^4_2$)$_t$—C(O)—(CR$^4_2$)$_t$—NR$^7$—(CR$^4_2$)$_t$—R$^8$.

In a tenth embodiment of the fourth aspect, one or both of Z and Z' are —C(O)—(CR$^4_2$)$_t$—NR$^7$—(CR$^4_2$)$_t$—R$^8$.

In an eleventh embodiment of the fourth aspect, one or both of Z and Z' are —C(O)—(CR$^4_2$)$_n$—NR$^7$—(CR$^4_2$)$_n$—C(O)—R$^{81}$.

In a twelfth embodiment of the fourth aspect, one or both of Z and Z' are —C(O)—(CR$^4_2$)$_n$—NR$^7$—C(O)—R$^{81}$.

In a thirteenth embodiment of the fourth aspect, one or both of Z and Z' are —C(O)—(CR$^4_2$)$_n$—NR$^7$—(CR$^4_2$)$_n$—C(O)—O—R$^{81}$.

In a fourteenth embodiment of the fourth aspect, one or both of Z and Z' are —C(O)—(CR$^4_2$)$_n$—NR$^7$—C(O)—O—R$^{81}$.

In a fifteenth embodiment of the fourth aspect, one or both of Z and Z' are —U—(CR$^4_2$)$_t$—R$^8$.

In a sixteenth embodiment of the fourth aspect, one or both of Z and Z' are —C(O)—(CR$^4_2$)$_t$—R$^8$.

In a seventeenth embodiment of the fourth aspect, one or both of Z and Z' are —[U—(CR$^4_2$)$_t$—NR$^5$—(CR$^4_2$)$_t$]$_u$—U—(CR$^4_2$)$_t$—O—(CR$^4_2$)$_t$—R$^8$.

In an eighteenth embodiment of the fourth aspect, one or both of Z and Z' are —U—(CR$^4_2$)$_t$—NR$^5$—(CR$^4_2$)$_t$—U—(CR$^4_2$)$_t$—O—(CR$^4_2$)$_t$—R$^8$.

In a nineteenth embodiment of the fourth aspect, one or both of Z and Z' are —C(O)—(CR$^4_2$)$_t$—NR$^5$—(CR$^4_2$)$_t$—C(O)—(CR$^4_2$)$_t$—O—(CR$^4_2$)$_t$—R$^8$.

In a twentieth embodiment of the fourth aspect, one or both of Z and Z' are —U—(CR$^4_2$)$_t$—O—(CR$^4_2$)$_t$—R$^8$.

In a twenty-first embodiment of the fourth aspect, one or both of Z and Z' are —C(O)—(CR$^4_2$)$_t$—O—(CR$^4_2$)$_t$—R$^8$.

In a twenty-second embodiment of the fourth aspect, one or both of Z and Z' are —C(O)—(CR$^4_2$)$_n$—NR$^7$—R$^8$ wherein R$^7$ and R$^8$ together form a 4-7 membered ring.

A fifth aspect of the invention provides a pharmaceutical composition comprising the compounds of the invention.

A sixth aspect of the invention provides use of the compounds of the invention in the manufacture of a medicament.

In a first embodiment of the sixth aspect the medicament is for the treatment of hepatitis C.

A seventh aspect of the invention provides a method of treating hepatitis C comprising administering to a subject in need thereof, a therapeutically effective amount of a compound of the invention.

DETAILED DESCRIPTION

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg (2007) "Advanced Organic Chemistry" 5$^{th}$ Ed. Vols. A and B, Springer Science+Business Media LLC, New York. The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology.

The term "alkanoyl" as used herein contemplates a carbonyl group with a lower alkyl group as a substituent.

The term "alkoxy" as used herein contemplates an oxygen with a lower alkyl group as a substituent and includes methoxy, ethoxy, butoxy, trifluoromethoxy and the like. It also includes divalent substituents linked to two separated oxygen atoms such as, without limitation, —O—(CH$_2$)$_{1-4}$—O—, —O—CF$_2$—O—, —O—(CH$_2$)$_{1-4}$—O—(CH$_2$CH$_2$—O)$_{1-4}$— and —(O—CH$_2$CH$_2$—O)$_{1-4}$—.

The term "alkoxycarbonyl" as used herein contemplates a carbonyl group with an alkoxy group as a substituent.

The term "alkyl" as used herein contemplates substituted or unsubstituted, straight and branched chain alkyl radicals containing from one to fifteen carbon atoms. The term "lower alkyl" as used herein contemplates both straight and branched chain alkyl radicals containing from one to six carbon atoms and includes methyl, ethyl, propyl, isopropyl, butyl, isobutyl, tert-butyl and the like. The alkyl group may be optionally substituted with one or more substituents selected from halogen, —CN, —NO$_2$, —C(O)$_2$R, —C(O)R, —O—R, —N(R$^N$)$_2$, —N(R$^N$)C(O)R, —N(R$^N$)S(O)$_2$R, —SR, —C(O)$_N$(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "amino" as used herein contemplates a group of the structure —NR$^N_2$.

The term "amino acid" as used herein contemplates a group of the structure

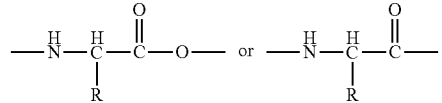

in either the D or the L configuration and includes but is not limited to the twenty "standard" amino acids: isoleucine, leucine, lysine, methionine, phenylalanine, threonine, tryptophan, valine, alanine, asparagine, aspartate, cysteine, glutamate, glutamine, glycine, proline, serine, tyrosine, arginine and histidine. The present invention also includes, without limitation, D-configuration amino acids, beta-amino acids, amino acids having side chains as well as all non-natural amino acids known to one skilled in the art.

The terms "aryl," "aromatic group" or "aromatic ring" as used herein contemplates substituted or unsubstituted single-ring and multiple aromatic groups (for example, phenyl, pyridyl and pyrazole, etc.) and polycyclic ring systems (naphthyl and quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocycles and/or heteroaryls. The aryl group may be optionally substituted with one or more substituents selected from halogen, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The term "aralkyl" as used herein contemplates a lower alkyl group which has as a substituent an aromatic group, which aromatic group may be substituted or unsubstituted.

The aralkyl group may be optionally substituted with one or more substituents selected from halogen, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, phosphate, phosphonate, cycloalkyl, cycloalkenyl, aryl and heteroaryl.

The term "carbamoyl" as used herein contemplates a group of the structure

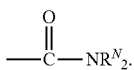

The term "carbonyl" as used herein contemplates a group of the structure

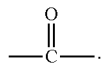

The term "cycloalkyl" as used herein contemplates substituted or unsubstituted cyclic alkyl radicals containing from three to twelve carbon atoms and includes cyclopropyl, cyclopentyl, cyclohexyl and the like. The term "cycloalkyl" also includes polycyclic systems having two rings in which two or more atoms are common to two adjoining rings (the rings are "fused"). The cycloalkyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "cycloalkenyl" as used herein contemplates substituted or unsubstituted cyclic alkenyl radicals containing from four to twelve carbon atoms in which there is at least one double bond between two of the ring carbons and includes cyclopentenyl, cyclohexenyl and the like. The term "cycloalkenyl" also includes polycyclic systems having two rings in which two or more atoms are common to two adjoining rings (the rings are "fused"). The cycloalkenyl group may be optionally substituted with one or more substituents selected from halo, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —S(O)$_2$N(R$^N$)$_2$, phosphate, phosphonate, alkyl, cycloalkenyl, aryl and heteroaryl.

The term "halo" or "halogen" as used herein includes fluorine, chlorine, bromine and iodine.

The term "heteroalkyl" as used herein contemplates an alkyl with one or more heteroatoms.

The term "heteroatom", particularly within a ring system, refers to N, O and S.

The term "heterocyclic group," "heterocycle" or "heterocyclic ring" as used herein contemplates substituted or unsubstituted aromatic and non-aromatic cyclic radicals having at least one heteroatom as a ring member. Preferred heterocyclic groups are those containing five or six ring atoms which includes at least one hetero atom and includes cyclic amines such as morpholino, piperidino, pyrrolidino and the like and cyclic ethers, such as tetrahydrofuran, tetrahydropyran and the like. Aromatic heterocyclic groups, also termed "heteroaryl" groups, contemplates single-ring hetero-aromatic groups that may include from one to three heteroatoms, for example, pyrrole, furan, thiophene, imidazole, oxazole, thiazole, triazole, pyrazole, oxodiazole, thiadiazole, pyridine, pyrazine, pyridazine, pyrimidine and the like. The term heteroaryl also includes polycyclic hetero-aromatic systems having two or more rings in which two or more atoms are common to two adjoining rings (the rings are "fused") wherein at least one of the rings is a heteroaryl, e.g., the other rings can be cycloalkyls, cycloalkenyls, aryl, heterocycles and/or heteroaryls. Examples of polycyclic heteroaromatic systems include quinoline, isoquinoline, cinnoline, tetrahydroisoquinoline, quinoxaline, quinazoline, benzimidazole, benzofuran, benzothiophene, benzoxazole, benzothiazole, indazole, purine, benzotriazole, pyrrolepyridine, pyrrazolopyridine and the like. The heterocyclic group may be optionally substituted with one or more substituents selected from the group consisting of halo, alkyl, —CN, —NO$_2$, —CO$_2$R, —C(O)R, —O—R, —N(R$^N$)$_2$, —N(R$^N$)C(O)R, —N(R$^N$)S(O)$_2$R, —SR, —C(O)N(R$^N$)$_2$, —OC(O)R, —OC(O)N(R$^N$)$_2$, —SOR, —SO$_2$R, —SO$_3$R, —S(O)$_2$N(R$^N$)$_2$, —SiR$_3$, —P(O)R, phosphate, phosphonate, cycloalkyl, cycloalkenyl, aryl and heteroaryl.

The terms "phosphate" and "phosphonate" as used herein refer to the moieties having the following structures, respectively:

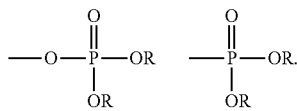

The term sulfonamide as used herein contemplates a group having the structure

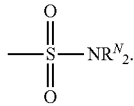

The term "sulfonate" as used herein contemplates a group having the structure

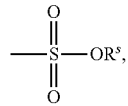

wherein R$^s$ is selected from the group consisting of hydrogen, C$_1$-C$_{10}$ alkyl, C$_2$-C$_{10}$ alkenyl, C$_2$-C$_{10}$ alkynyl, C$_1$-C$_{10}$ alkanoyl or C$_1$-C$_{10}$ alkoxycarbonyl.

The term "sulfonyl" as used herein contemplates a group having the structure

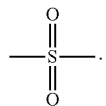

"Substituted sulfonyl" as used herein contemplates a group having the structure

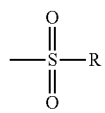

including, but not limited to alkylsulfonyl and arylsulfonyl.

The term "thiocarbonyl," as used herein, means a carbonyl wherein an oxygen atom has been replaced with a sulfur atom.

Each R is independently selected from hydrogen, —OH, —CN, —NO$_2$, halogen, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate, sulfonamide, amino and oxo.

Each R$^N$ is independently selected from the group consisting of hydrogen, —OH, C$_1$ to C$_{12}$ alkyl, C$_1$ to C$_{12}$ heteroalkyl, alkenyl, alkynyl, cycloalkyl, heterocycle, aryl, heteroaryl, aralkyl, alkoxy, alkoxycarbonyl, alkanoyl, carbamoyl, substituted sulfonyl, sulfonate and sulfonamide. Two R$^N$ may be taken together with C, O, N or S to which they are attached to form a 5 to 7 membered ring which may optionally contain a further heteroatom.

The compounds of the present invention may be used to inhibit or reduce the activity of HCV, particularly HCV's NS5A protein. In these contexts, inhibition and reduction of activity of the NS5A protein refers to a lower level of the measured activity relative to a control experiment in which the cells or the subjects are not treated with the test compound. In particular aspects, the inhibition or reduction in the measured activity is at least a 10% reduction or inhibition. One of skill in the art will appreciate that reduction or inhibition of the measured activity of at least 20%, 50%, 75%, 90% or 100% or any number in between, may be preferred for particular applications.

In a first aspect of the invention, compounds of formula I are provided:

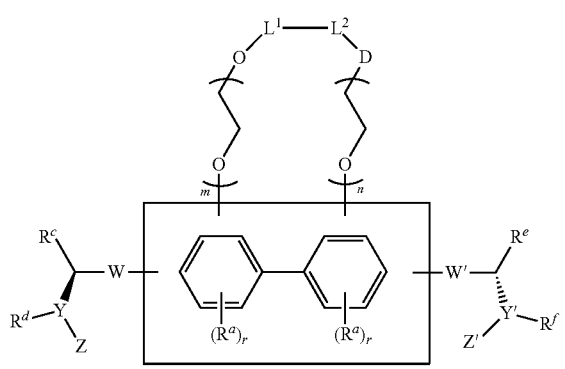

I wherein:
L$^1$ and L$^2$ are either linked or not linked,
when not linked, L$^1$ and L$^2$ are independently H or lower alkyl (containing 1 to 4 carbons) moieties;
when linked, L$^1$-L$^2$ are independently —CH$_2$C(O)—, —C(O)—, —(CH$_2$CH$_2$—O—CH$_2$CH$_2$)$_p$— wherein p is independently 1, 2 or 3, or lower alkyl (containing 1 to 4 carbons) moieties;
D is a bond, CH$_2$, NH, O, or S;
m and n are independently 0, 1, 2, 3 or 4 and m and n may not be both 0;
each R$^a$ is independently selected from the group consisting of —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1 or 2 or 3;

W and W' are each independently selected from the group consisting of

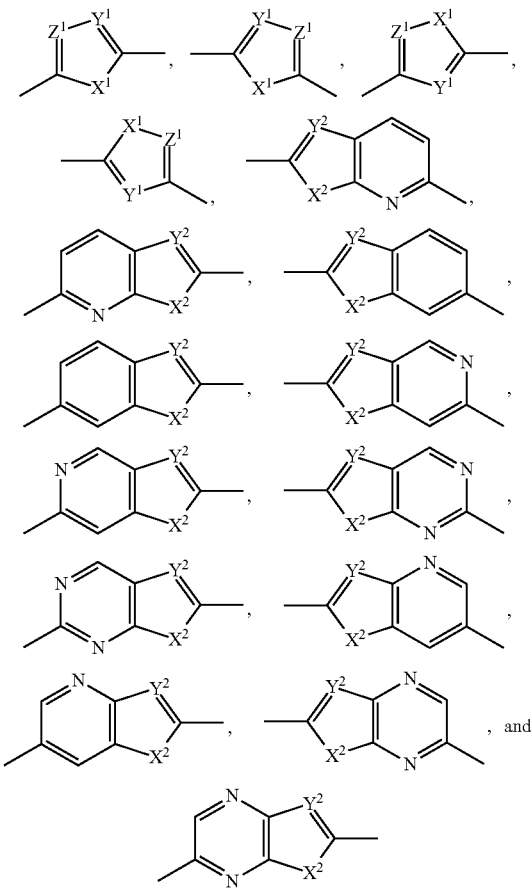

wherein:
X$^1$ is CH$_2$, NH, O or S,
Y$^1$, Y$^2$ and Z$^1$ are each independently CH or N,
X$^2$ is NH, O or S,
W and W' are each independently optionally substituted with one or more substituents selected from the group consisting of —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and W and W' attached to the central biphenyl moiety can have the following substitution patterns:

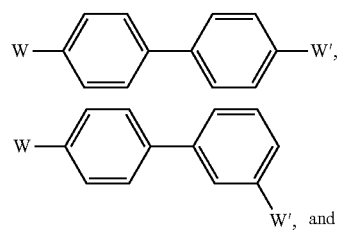

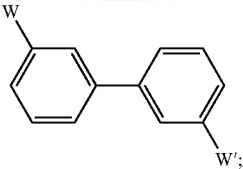

wherein, the biphenyl moiety can be substituted with 0-4 nitrogen atom(s); and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, —[U—$(CR^4_2)_t$—$NR^5$—$C(R^4_2)_t]_u$—U—$(CR^4_2)_t$—$NR^7$—$(CR^4_2)_t$—$R^8$, —U—$(CR^4_2)_t$—$R^8$, and —[U—$(CR^4_2)_t$—$NR^5$—$(CR^4_2)_t]_u$—U—$(CR^4_2)_t$—O—$(CR^4_2)_t$—$R^8$, wherein, U is selected from the group consisting of —C(O)—, —C(S)— and —S(O)$_2$—, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, —C(O)—$R^{81}$, —C(S)—$R^{81}$, —C(O)—O—$R^{81}$, —C(O)—N—$R^{81}_2$, —S(O)$_2$—$R^{81}$ and —S(O)$_2$—N—$R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the first aspect, one or both of W and W' are selected from the group consisting of

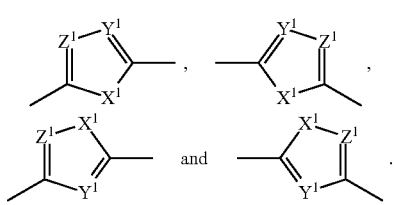

In a second embodiment of the first aspect, one or both of W and W' are selected from the group consisting of

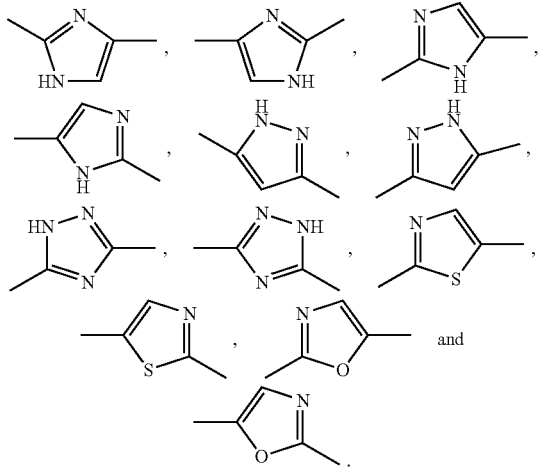

In a third embodiment of the first aspect, $R^c$, $R^d$, $R^e$ and $R^f$ are each independently selected from the group consisting of: hydrogen, $C_1$ to $C_8$ alkyl and $C_1$ to $C_8$ heteroalkyl, wherein, each hetero atom, if present, is independently N, O or S, $R^c$ and $R^d$ are optionally joined to form a 4- to 8-membered heterocycle which is optionally fused to another 3- to 6-membered heterocycle, and $R^e$ and $R^f$ are optionally joined to form a 4- to 8-membered heterocycle which is optionally fused to another 3- to 6-membered heterocycle.

In a fourth embodiment of the first aspect, one or both of $R^c$ and $R^d$ or $R^e$ and $R^f$ are optionally joined to form a 4- to 8-membered heterocycle which is optionally fused to another 3- to 6-membered heterocycle.

In a fifth embodiment of the first aspect, $R^e$ and $R^d$ are joined and form a heterocyclic fused ring system selected from the group consisting of:

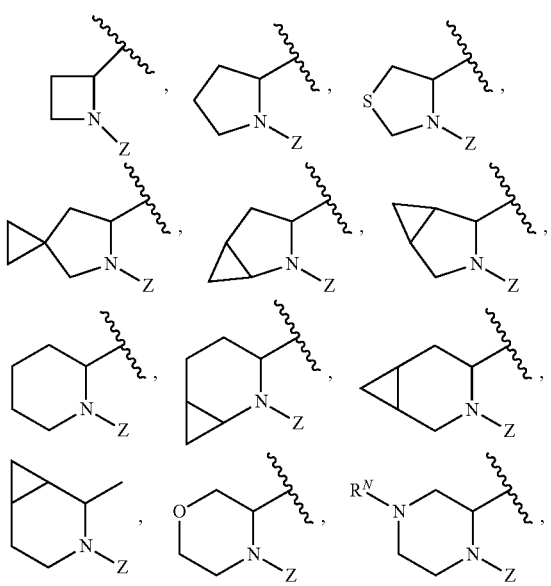

19
-continued

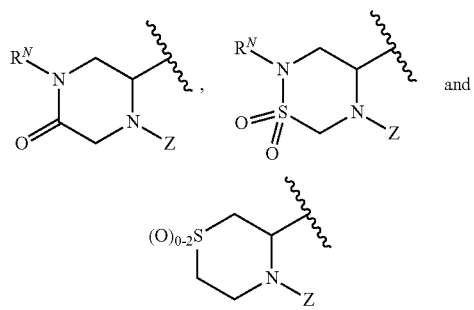

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a sixth embodiment of the first aspect, $R^e$ and $R^f$ are joined and form a heterocyclic fused ring system selected from the group consisting of:

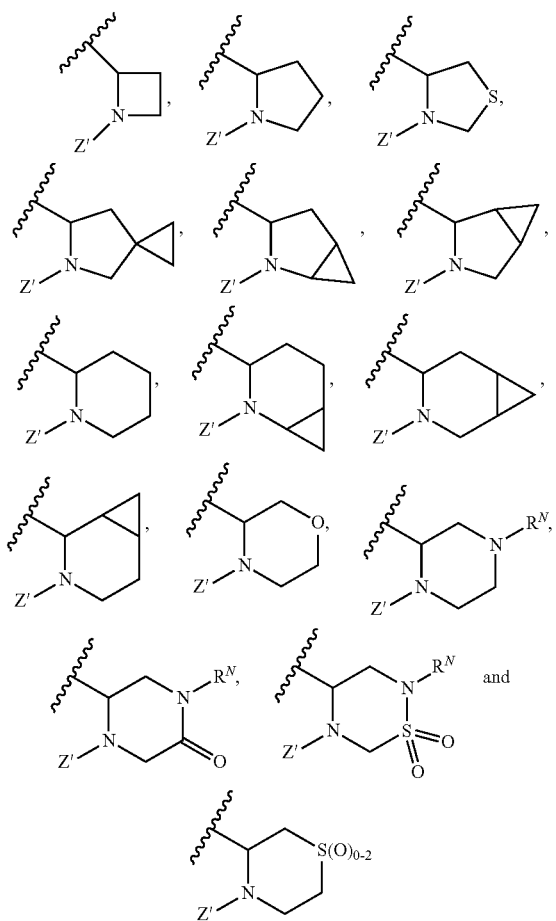

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

In a second aspect of the invention, compounds have formula II:

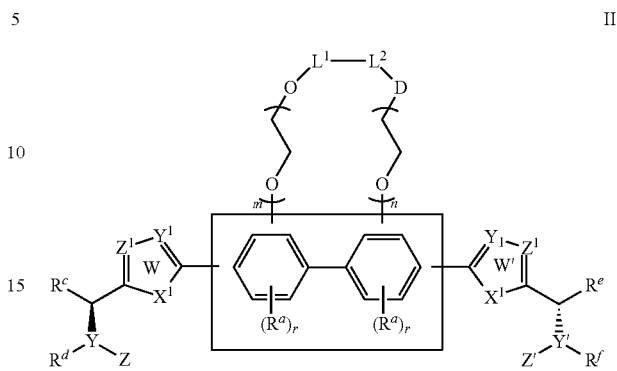

II wherein:
$L^1$ and $L^2$ are either linked or not linked, when not linked, $L^1$ and $L^2$ are independently H or lower alkyl (containing 1 to 4 carbons) moieties;
when linked, $L^1$-$L^2$ are independently —CH$_2$C(O)—, —C(O)—, —(CH$_2$CH$_2$—O—CH$_2$CH$_2$)$_p$— wherein p is independently 1, 2 or 3, or lower alkyl (containing 1 to 4 carbons) moieties;
D is a bond, CH$_2$, NH, O, or S;
m and n are independently 0, 1, 2, 3 or 4 and m and n may not be both 0;
each $R^a$ is independently selected from the group consisting of —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1, 2 or 3;
$X^1$ is CH$_2$, NH, O or S,
$Y^1$, $Y^2$ and $Z^1$ are each independently CH or N,
$X^2$ is NH, O or S,
W and W' are each independently optionally substituted with one or more substituents selected from the group consisting of —CN, —NO$_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
W and W' attached to the central biphenyl moiety can have the following substitution patterns:

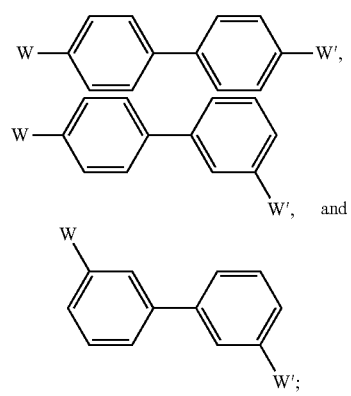

wherein, the biphenyl moiety can be substituted with 0-4 nitrogen atom(s); and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, $—[U—(CR^4_2)_t—NR^5—C(R^4_2)_t]_u—U—(CR^4_2)_t—NR^7—(CR^4_2)_t—R^8$, $—U—(CR^4_2)_t—R^8$, and $—[U—(CR^4_2)_t—NR^5—(CR^4_2)_t]_u—U—(CR^4_2)_t—O—(CR^4_2)_t—R^8$, wherein, U is selected from the group consisting of $—C(O)—$, $—C(S)—$ and $—S(O)_2—$, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, $—C(O)—R^{81}$, $—C(S)—R^{81}$, $—C(O)—O—R^{81}$, $—C(O)—N—R^{81}_2$, $—S(O)_2—R^{81}$ and $—S(O)_2—N—R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a third aspect of the invention, compounds have formula III:

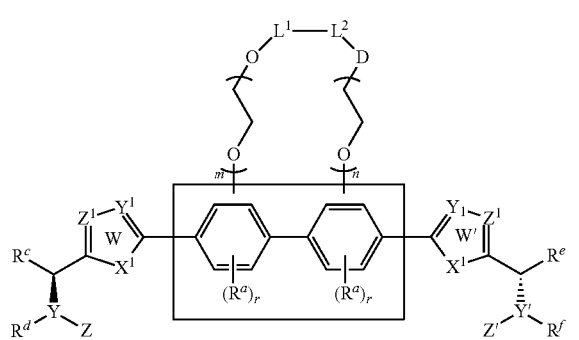

wherein:

$L^1$ and $L^2$ are either linked or not linked, when not linked, $L^1$ and $L^2$ are independently H or lower alkyl (containing 1 to 4 carbons) moieties;

when linked, $L^1$-$L^2$ are independently $—CH_2C(O)—$, $—C(O)—$, $—(CH_2CH_2—O—CH_2CH_2)_p—$ wherein p is independently 1, 2 or 3, or lower alkyl (containing 1 to 4 carbons) moieties;

D is a bond, $CH_2$, NH, O, or S;

m and n are independently 0, 1, 2, 3 or 4 and m and n may not be both 0;

each $R^a$ is independently selected from the group consisting of $—CN$, $—NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;

each r is independently 0, 1, 2 or 3;

$X^1$ is $CH_2$, NH, O or S, $Y^1$, $Y^2$ and $Z^1$ are each independently CH or N, $X^2$ is NH, O or S, W and W' are each independently optionally substituted with one or more substituents selected from the group consisting of $—CN$, $—NO_2$, halogen, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and each $R^c$, $R^d$, $R^e$ and $R^f$ is independently selected from the group consisting of: hydrogen, $C_1$ to $C_8$ alkyl, $C_1$ to $C_8$ heteroalkyl, aralkyl and a 4- to 8-membered ring which may be cycloalkyl, heterocycle, heteroaryl or aryl, wherein, each hetero atom, if present, is independently N, O or S, each of $R^c$, $R^d$, $R^e$ and $R^f$ may optionally be substituted by $C_1$ to $C_8$ alkyl, $C_1$ to $C_8$ heteroalkyl, aralkyl, or a 4- to 8-membered ring which may be cycloalkyl, heterocycle, heteroaryl or aryl and wherein each heteroatom, if present, is independently N, O or S, $R^c$ and $R^d$ are optionally joined to form a 4- to 8-membered heterocycle which is optionally fused to another 3- to 5-membered heterocycle or heteroaryl ring, and $R^e$ and $R^f$ are optionally joined to form a 4- to 8-membered heterocycle which is optionally fused to another 3- to 5-membered heterocycle or heteroaryl ring;

Y and Y' are each independently carbon or nitrogen; and

Z and Z' are independently selected from the group consisting of hydrogen, $C_1$ to $C_8$ alkyl, $C_1$ to $C_8$ heteroalkyl, cycloalkyl, heterocycle, aryl, heteroaryl, aralkyl, 1-3 amino acids, $—[U—(CR^4_2)_t—NR^5—C(R^4_2)_t]_u—U—(CR^4_2)_t—NR^7—(CR^4_2)_t—R^8$, $—U—(CR^4_2)_t—R^8$, and $—[U—(CR^4_2)_t—NR^5—(CR^4_2)_t]_u—U—(CR^4_2)_t—O—(CR^4_2)_t—R^8$, wherein, U is selected from the group consisting of $—C(O)—$, $—C(S)—$ and $—S(O)_2—$, each $R^4$, $R^5$ and $R^7$ is independently selected from the group consisting of hydrogen, $C_1$ to $C_8$ alkyl, $C_1$ to $C_8$ heteroalkyl, cycloalkyl, heterocycle, aryl, heteroaryl and aralkyl, $R^8$ is selected from the group consisting of hydrogen, $C_1$ to $C_8$ alkyl, $C_1$ to $C_8$ heteroalkyl, cycloalkyl, heterocycle, aryl, heteroaryl, aralkyl, $—C(O)—R^{81}$, $—C(S)—R^{81}$, $—C(O)—O—R^{81}$, $—C(O)—N—R^{81}_2$, $—S(O)_2—R^{81}$ and $—S(O)_2—N—R^{81}_2$, wherein each $R^{81}$ is independently chosen from the group consisting of hydrogen, $C_1$ to $C_8$ alkyl, $C_1$ to $C_8$ heteroalkyl, cycloalkyl, heterocycle, aryl, heteroaryl and aralkyl, optionally, $R^7$ and $R^8$ together form a 4-7 membered ring, each t is independently 0, 1, 2, 3, or 4, and u is 0, 1, or 2.

In a first embodiment of the third aspect, compounds of formula IIIa are provided:

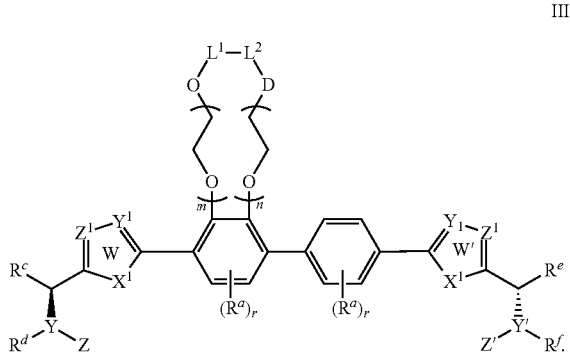

IIIa

In a second embodiment of the third aspect, compounds of formula IIIb are provided:

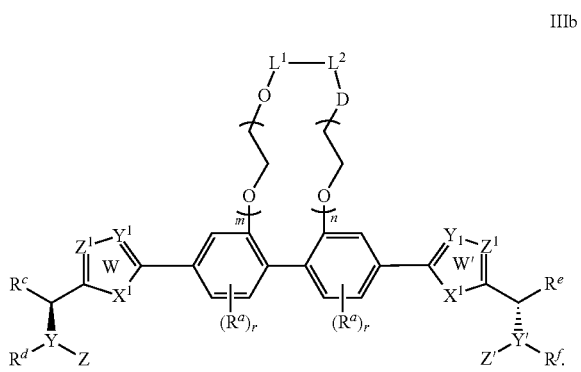

IIIb

In a third embodiment of the third aspect, compounds of formula IIIc are provided:

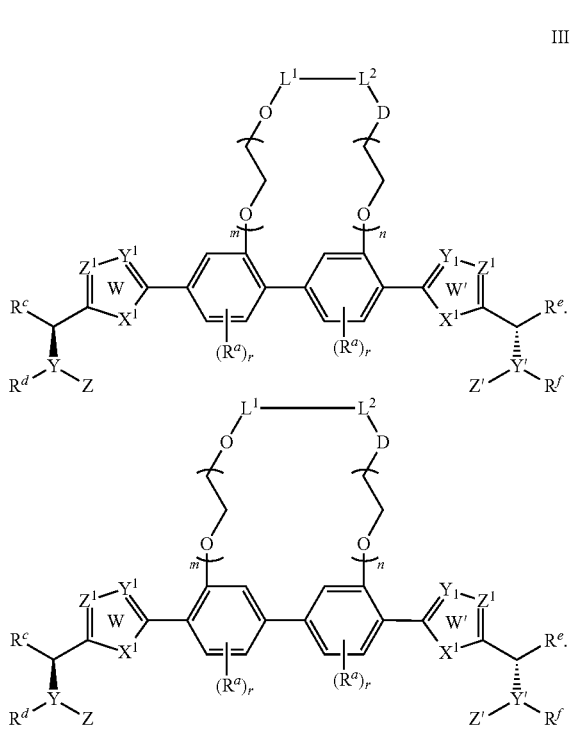

IIIc

In a fourth embodiment of the third aspect, compounds of formula IIId are provided:

In a fifth embodiment of the third aspect, one or both of $X^1$ are —S—.

In a six embodiment of the third aspect, one or both of $X^1$ are —O—.

In a seventh embodiment of the third aspect, one or both of $X^1$ are —NH—.

In an eighth embodiment of the third aspect, one or both of $Z^1$ is —N—.

In a ninth embodiment of the third aspect, one or both of $Y^1$ is —N—.

In a fourth aspect of the invention, Z and Z' in any of the previous aspects are each 1-3 amino acids.

In a second embodiment of the fourth aspect, Z and Z' are each independently selected from the group consisting of —[U—$(CR^4{}_2)_t$—$NR^5$—$(CR^4{}_2)_t]_u$—U—$(CR^4{}_2)_t$—$NR^7$—$(CR^4{}_2)_t$—$R^8$, —U—$(CR^4{}_2)_t$—$R^8$ and —[U—$(CR^4{}_2)_t$—$NR^5$—$(CR^4{}_2)_t]_u$—U—$(CR^4{}_2)_t$—O—$(CR^4{}_2)_t$—$R^8$.

In a third embodiment of the fourth aspect, one or both of Z and Z' are —[U—$(CR^4{}_2)_t$—$NR^5$—$(CR^4{}_2)_t]_u$—U—$(CR^4{}_2)_t$—$NR^7$—$(CR^4{}_2)_t$—$R^8$.

In a fourth embodiment of the fourth aspect, one or both of Z and Z' are —U—$(CR^4{}_2)_t$—$NR^5$—$(CR^4{}_2)_t$—U—$(CR^4{}_2)_t$—$NR^7$—$(CR^4{}_2)_t$—$R^8$.

In a fifth embodiment of the fourth aspect, one or both of Z and Z' are —U—$(CR^4{}_2)_t$—$NR^5$—$(CR^4{}_2)_t$—$R^8$.

In a sixth embodiment of the fourth aspect, one or both of Z and Z' are —[C(O)—$(CR^4{}_2)_t$—$NR^5$—$(CR^4{}_2)_t]_u$—U—$(CR^4{}_2)_t$—$NR^7$—$(CR^4{}_2)_t$—$R^8$.

In a seventh embodiment of the fourth aspect, one or both of Z and Z' are —C(O)—$(CR^4{}_2)_t$—$NR^5$—$(CR^4{}_2)_t$—U—$(CR^4{}_2)_t$—$NR^7$—$(CR^4{}_2)_t$—$R^8$.

In an eighth embodiment of the fourth aspect, one or both of Z and Z' are —[C(O)—$(CR^4{}_2)_t$—$NR^5$—$(CR^4{}_2)_t]_u$—C(O)—$(CR^4{}_2)_t$—$NR^7$—$(CR^4{}_2)_t$—$R^8$.

In a ninth embodiment of the fourth aspect, one or both of Z and Z' are —C(O)—$(CR^4{}_2)_t$—$NR^5$—$(CR^4{}_2)_t$—C(O)—$(CR^4{}_2)_t$—$NR^7$—$(CR^4{}_2)_t$—$R^8$.

In a tenth embodiment of the fourth aspect, one or both of Z and Z' are —C(O)—$(CR^4{}_2)_t$—$NR^7$—$(CR^4{}_2)_t$—$R^8$.

In an eleventh embodiment of the fourth aspect, one or both of Z and Z' are —C(O)—$(CR^4{}_2)_n$—$NR^7$—$(CR^4{}_2)_n$—C(O)—$R^{81}$.

In a twelfth embodiment of the fourth aspect, one or both of Z and Z' are —C(O)—$(CR^4{}_2)_n$—$NR^7$—C(O)—$R^{81}$.

In a thirteenth embodiment of the fourth aspect, one or both of Z and Z' are —C(O)—$(CR^4{}_2)_n$—$NR^7$—$(CR^4{}_2)_n$—C(O)—O—$R^{81}$.

In a fourteenth embodiment of the fourth aspect, one or both of Z and Z' are —C(O)—$(CR^4{}_2)_n$—$NR^7$—C(O)—O—$R^{81}$.

In a fifteenth embodiment of the fourth aspect, one or both of Z and Z' are —U—$(CR^4{}_2)_t$—$R^8$.

In a sixteenth embodiment of the fourth aspect, one or both of Z and Z' are —C(O)—$(CR^4{}_2)_t$—$R^8$.

In a seventeenth embodiment of the fourth aspect, one or both of Z and Z' are —[U—$(CR^4{}_2)_t$—$NR^5$—$(CR^4{}_2)_t]_u$—U—$(CR^4{}_2)_t$—O—$(CR^4{}_2)_t$—$R^8$.

In an eighteenth embodiment of the fourth aspect, one or both of Z and Z' are —U—$(CR^4{}_2)_t$—$NR^5$—$(CR^4{}_2)_t$—U—$(CR^4{}_2)_t$—O—$(CR^4{}_2)_t$—$R^8$.

In a nineteenth embodiment of the fourth aspect, one or both of Z and Z' are —C(O)—$(CR^4{}_2)_t$—$NR^5$—$(CR^4{}_2)_t$—C(O)—$(CR^4{}_2)_t$—O—$(CR^4{}_2)_t$—$R^8$.

In a twentieth embodiment of the fourth aspect, one or both of Z and Z' are —U—$(CR^4{}_2)_t$—O—$(CR^4{}_2)_t$—$R^8$.

In a twenty-first embodiment of the fourth aspect, one or both of Z and Z' are —C(O)—$(CR^4{}_2)_t$—O—$(CR^4{}_2)_t$—$R^8$.

In a twenty-second embodiment of the fourth aspect, one or both of Z and Z' are —C(O)—(CR$^4_2$)$_n$—NR$^7$—R$^8$ wherein R$^7$ and R$^8$ together form a 4-7 membered ring.

A fifth aspect of the invention provides a pharmaceutical composition comprising the compounds of the invention.

A sixth aspect of the invention provides use of the compounds of the invention in the manufacture of a medicament.

In a first embodiment of the sixth aspect the medicament is for the treatment of hepatitis C.

A seventh aspect of the invention provides a method of treating hepatitis C comprising administering to a subject in need thereof, a therapeutically effective amount of a compound of the invention.

General Synthesis

The following abbreviations are used throughout this application:
ACN Acetonitrile
AcOH Acetic acid
aq Aqueous
Boc t-Butoxycarbonyl
Cbz Benzoxylcarbonoyl
DCM Dichloromethane
DEAD Diethyl azodicarboxylate
DEPBT 3-(Diethoxy-phosphoryloxy)-3H-benzo[d][1,2,3]triazin-4-one
DIBAL Diisobutylaluminium hydride
DIEA (DIPEA) Diisopropylethylamine
DME 1,2-Dimethoxyethane
DMF N,N-Dimethylformamide
dppf 1,1'-Bis(diphenylphosphino)ferrocene
EDCI 1-Ethyl-3-[3-(dimethylamino)propyl]carbodiimide hydrochloride
EC$_{50}$ Effective concentration to produce 50% of the maximal effect
ESI Electrospray Ionization
Et$_3$N, TEA Triethylamine
EtOAc, EtAc Ethyl acetate
g Gram(s)
h or hr Hour(s)
HATU 2-(7-Aza-1H-benzotriazole-1-yl)-1,1,3,3-tetramethyluronium hexafluorophosphate
HOBt 1-Hydroxybenzotriazole
IC$_{50}$ The concentration of an inhibitor that causes a 50% reduction in a measured activity
LC-MS Liquid Chromatography Mass Spectrometry
MeOH Methanol
min Minute(s)
mmol Millimole(s)
Moc Methoxylcarbonyl
Ms Mesylate
NBS N-Bromosuccinimide
PEG Polyethylene glycol
PG Protective Group
Py, Pyr Pyridine
rt Room temperature
TEA Triethylamine
TFA Trifluoroacetic acid
THF Tetrahydrofuran
TLC Thin Layer Chromatography
TMSOTf Trimethylsilyl trifluoromethanesulfonate
Ts Tosylate Reagents and solvents used below can be obtained from commercial sources such as Aldrich Chemical Co. (Milwaukee, Wis., USA). Reagents and solvents used below can be obtained from commercial sources such as Aldrich Chemical Co. (Milwaukee, Wis., USA). $^1$HNMR spectra were recorded on a Bruker 400 MHz or 500 MHz NMR spectrometer. Significant peaks are tabulated in the order: chemical shift, multiplicity (s, singlet; d, doublet; t, triplet; q, quartet; m, multiplet; br s, broad singlet), coupling constant(s) in Hertz (Hz) and number of protons.

The following examples are provided by way of illustration only and not by way of limitation. Those skilled in the art will readily recognize a variety of noncritical parameters that could be changed or modified to yield essentially similar results. Efforts have been made to ensure accuracy with respect to numbers used (e.g., amounts, temperatures, etc.), but some experimental errors and deviations should, of course, be allowed for.

Liquid chromatography mass spectra (LC-MS) were obtained using an electrospray ionization (ESI) source in either the positive or negative mode.

The compounds were named using ChemDraw program from Cambridge Soft Inc.

The compounds of formula I in this invention are generally prepared following the synthetic strategies described in Scheme A. Key intermediate A-6 can be obtained via various paths, such as but not limited to Path A, Path B or Path C. The biphenyl moiety can be prepared bearing various substituents. The flanking W and W' moieties, along with the groups attached to them, may be constructed through a stepwise functional group transformation of G and G'. Once the central scaffold is in place, further elaboration of the two amine-bearing moieties gives additional derivatives.

Scheme A

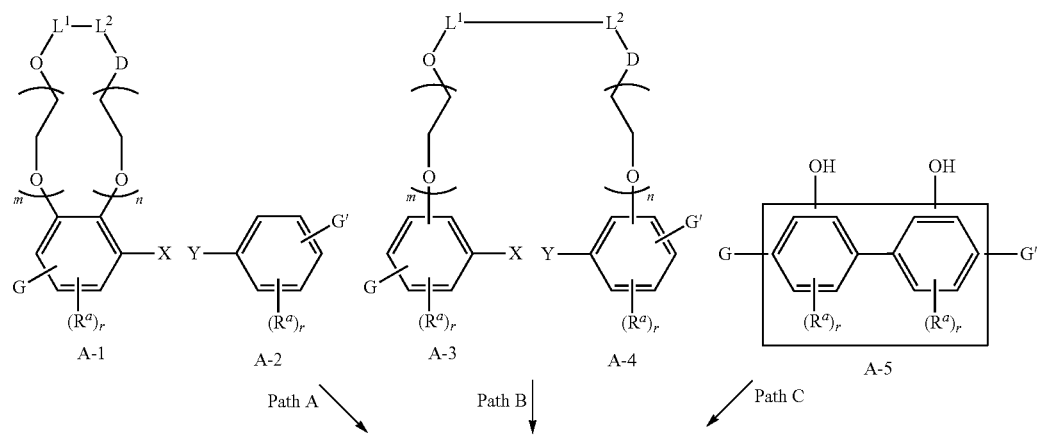

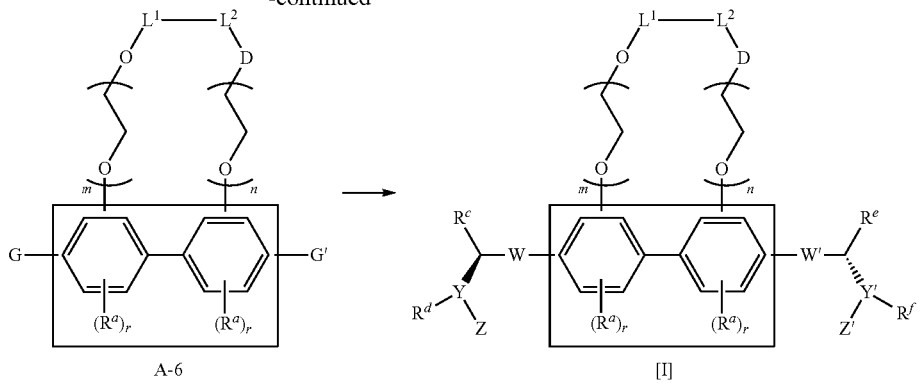

Preparations of the various chemical species are further illustrated in detail in the Examples section. The reactions are often carried out using known procedures, methods or analogous methods thereof. Examples of such known methods include these described in a general reference text such as Comprehensive Organic Transformations; Volumes 1-10, 1974-2002, Wiley Interscience; Comprehensive Organic Synthesis Volumes 1-9, Ed. B. M. Trost, I. Fleming, 1991, Pergamon. Using 2,2'-bis(2-methoxyethoxy)biphenyl as an example, we describe herein some of the approaches how W and W' are introduced.

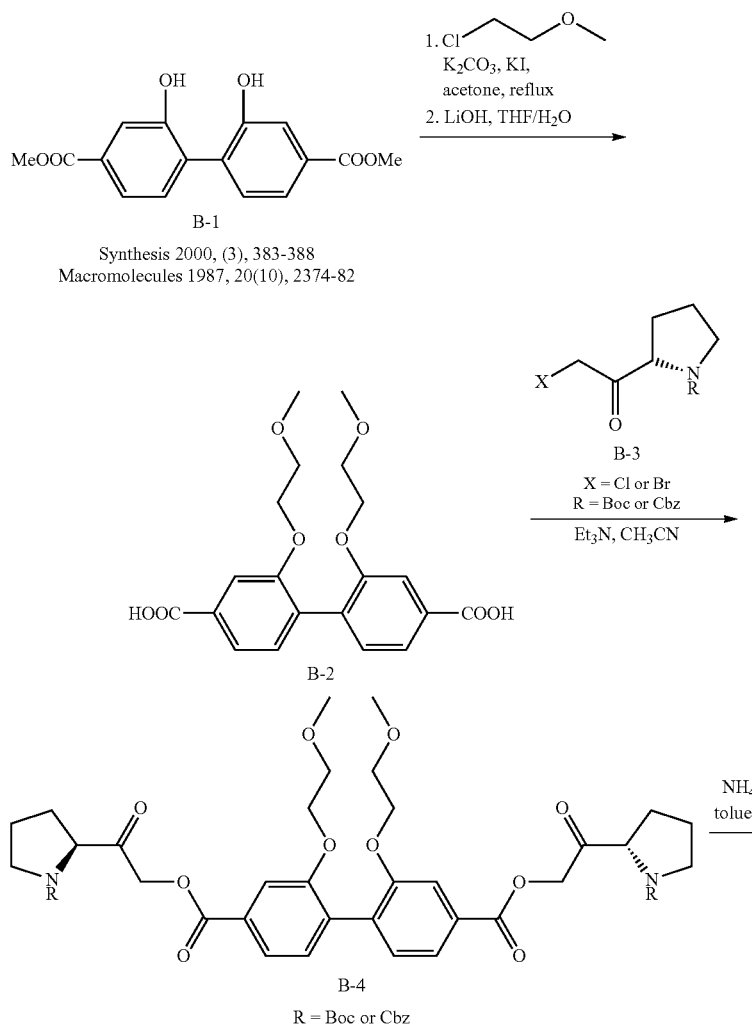

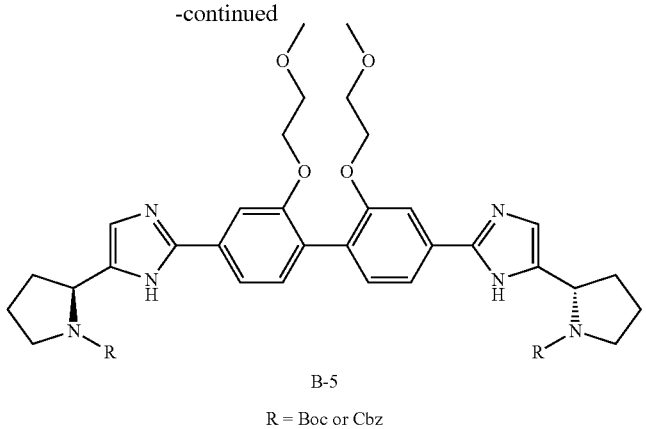

B-5

R = Boc or Cbz

As described in Scheme B, O-alkylation of B-1, followed by saponification, gives B-2, which reacts with B-3 to afford B-4. The subsequent imidazole ring formation of B-4 yield bis-imidazole B-5, which can be further transformed to give various analogs bearing different R groups through a sequence of typical de-protection and amide formation steps. Moreover, (S)-2-halo-1-(pyrrolidin-2-yl)ethanone B-3 can be replaced with other α-halo ketones derived from N-substituted D- or L-amino acids to generate bis-imidazole analogs of B-5.

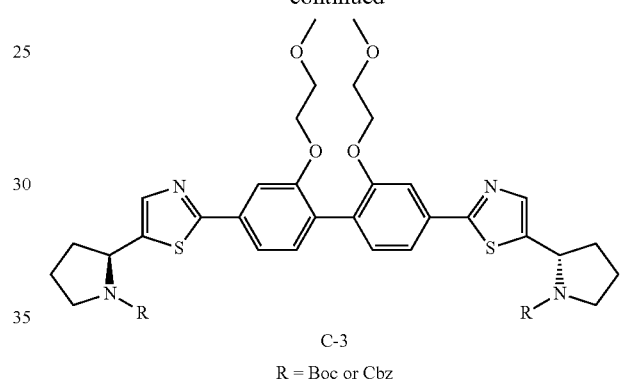

C-3

R = Boc or Cbz

As illustrated in Scheme C, bis-carboxylic acid B-2 is converted to the corresponding thio-amide derivative C-1, followed by treatment with N-substituted 2-bromo-2-((S)-pyrrolidin-2-yl)acetaldehyde (C-2) to give bis-thiazole analog C-3, which can be further transformed to give various analogs bearing different R groups through a sequence of typical de-protection and amide formation steps. Moreover, 2-bromo-2-((S)-pyrrolidin-2-yl)acetaldehyde (C-2) can be replaced with other 2-bromo-2-substituted acetaldehydes, derived from N-substituted D- or L-amino acids to generate bis-thiazole analogs of C-3.

Scheme C

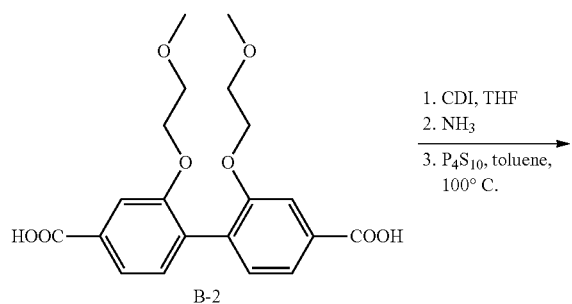

1. CDI, THF
2. NH$_3$
3. P$_4$S$_{10}$, toluene, 100° C.

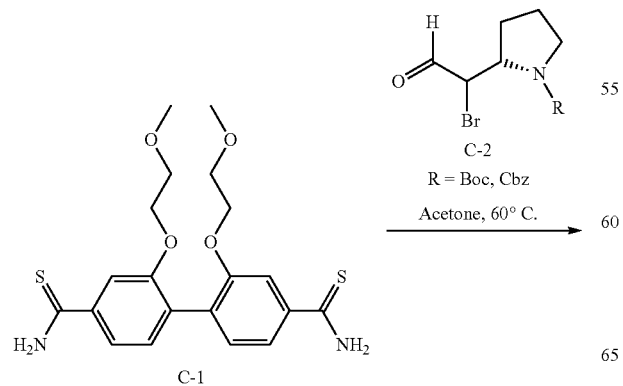

Scheme D

1. DIBAL, THF, -78° C.
2. CBr$_4$, PPh$_3$

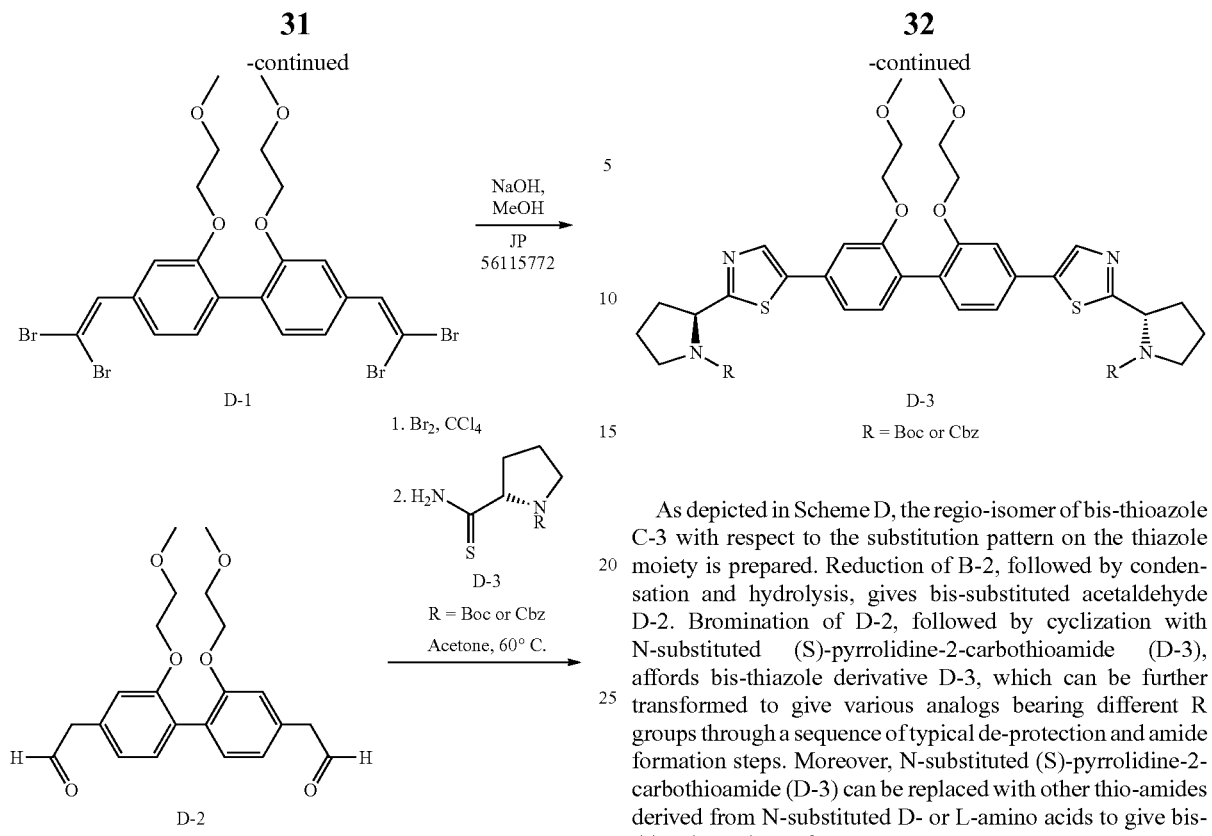

As depicted in Scheme D, the regio-isomer of bis-thioazole C-3 with respect to the substitution pattern on the thiazole moiety is prepared. Reduction of B-2, followed by condensation and hydrolysis, gives bis-substituted acetaldehyde D-2. Bromination of D-2, followed by cyclization with N-substituted (S)-pyrrolidine-2-carbothioamide (D-3), affords bis-thiazole derivative D-3, which can be further transformed to give various analogs bearing different R groups through a sequence of typical de-protection and amide formation steps. Moreover, N-substituted (S)-pyrrolidine-2-carbothioamide (D-3) can be replaced with other thio-amides derived from N-substituted D- or L-amino acids to give bis-thiazole analogs of D-3.

Scheme E

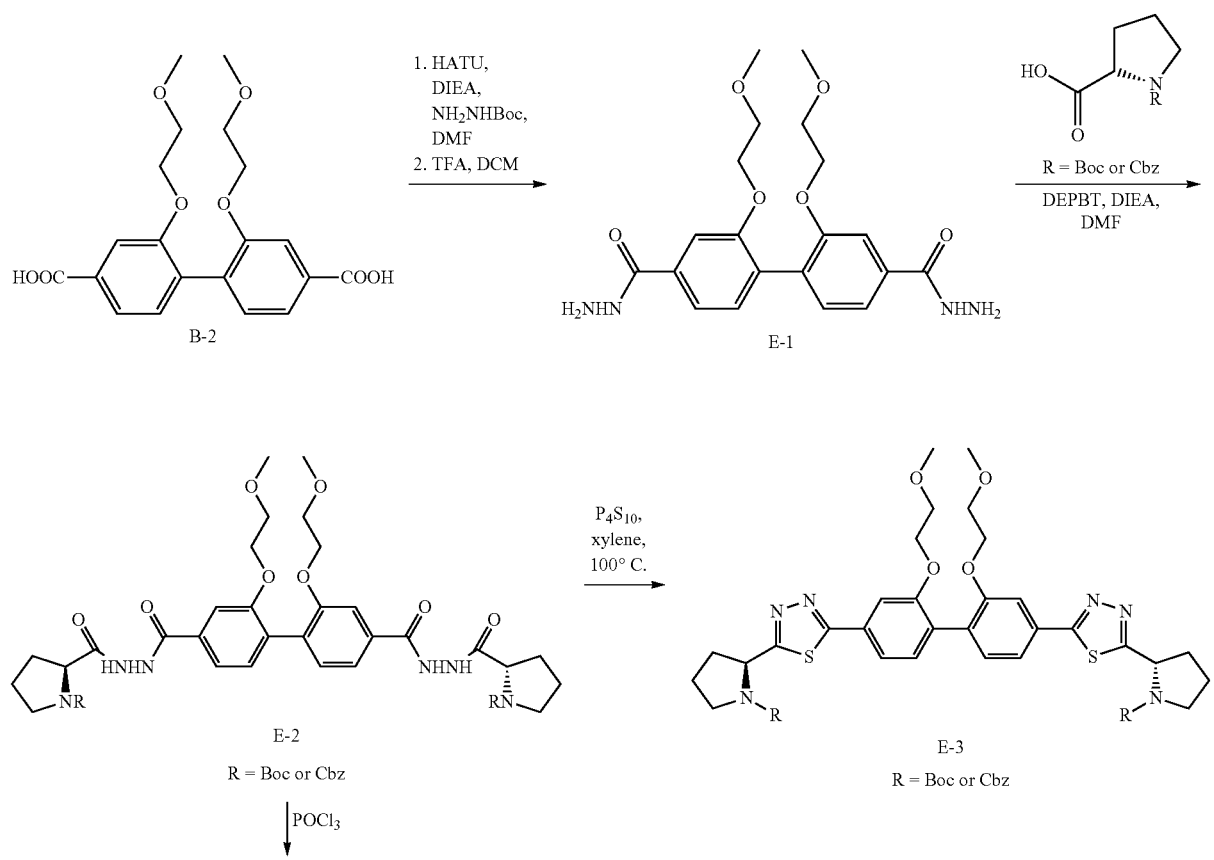

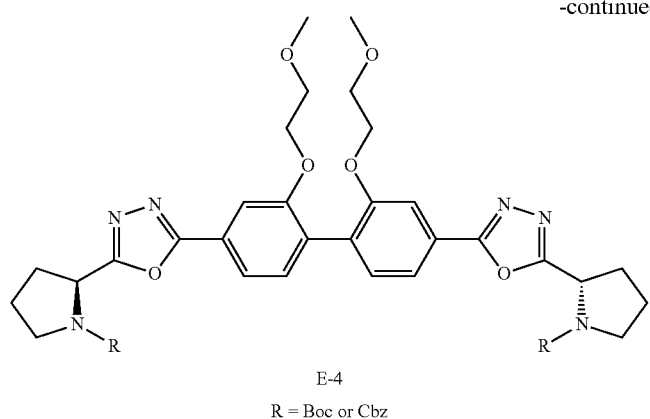

E-4

R = Boc or Cbz

As outlined in Scheme E, bis-carboxylic acid B-2 is converted to N,N'-diacylhydrazide E-2 through a three step sequence of amide formation, de-protection and amide formation. Ring cyclization of E-2 gives either bis-thiodiazole E-3 or bis-oxadiazole E-4 when the proper de-hydration reagents are used. Both E-3 and E-4 can be further transformed to give various analogs bearing different R groups through a sequence of typical de-protection and amide formation steps. Moreover, N-substituted-L-Pro-OH can be replaced with other N-substituted D- or L-amino acids to generate analogs of E-3 and E-4, respectively.

Scheme F

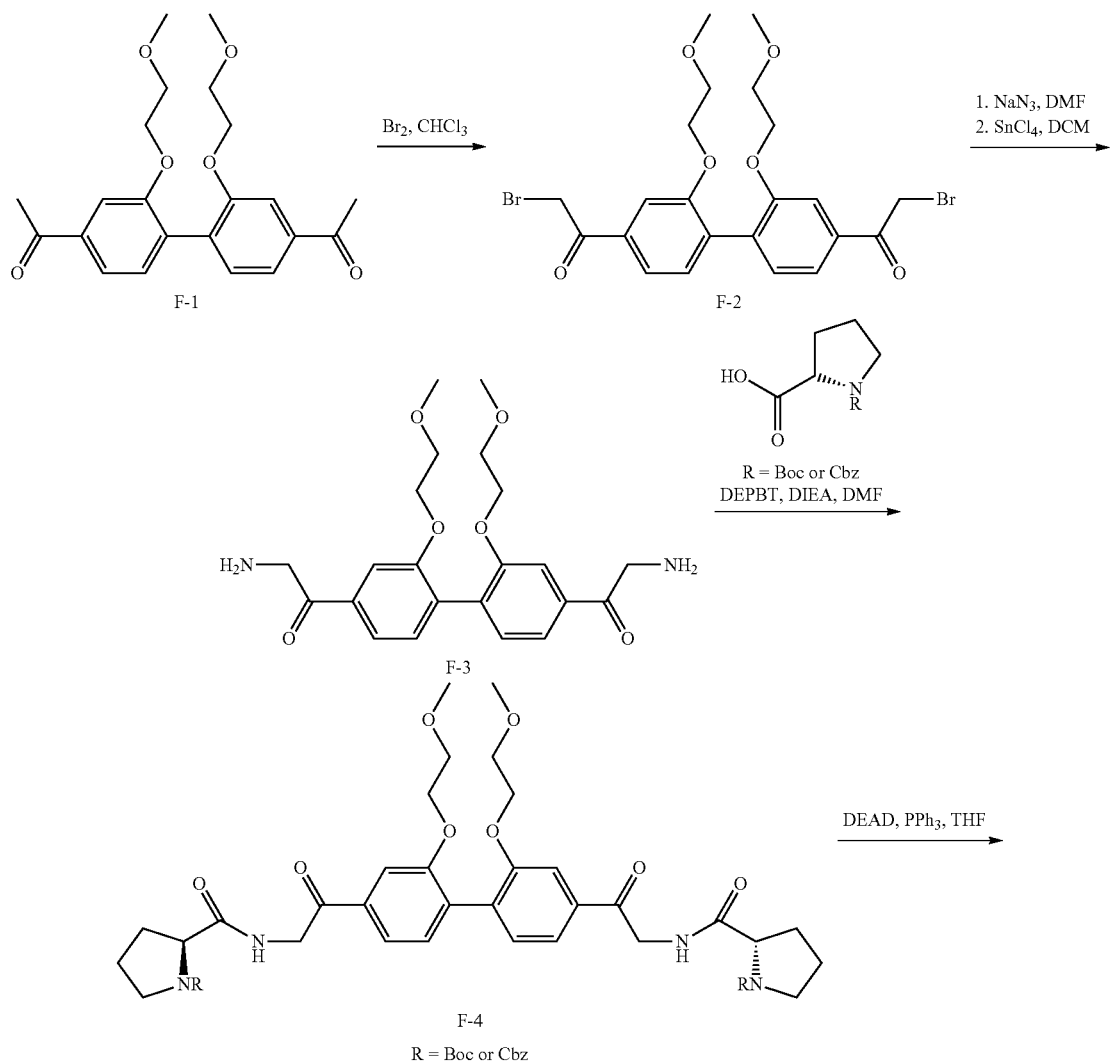

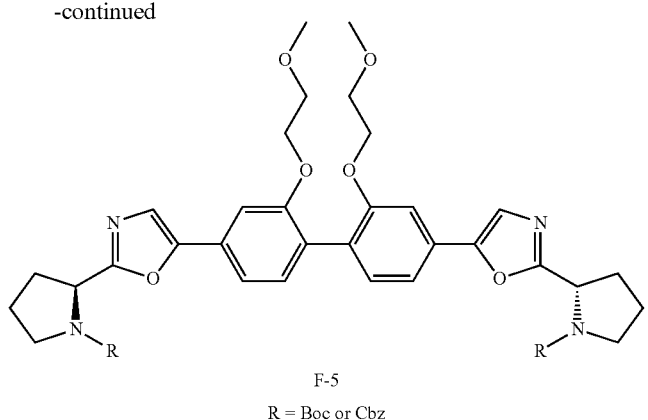

F-5

R = Boc or Cbz

As shown in Scheme G, α-chloro ketone F-2, readily prepared from F-1, is converted to the corresponding α-amino ketone F-3. Amide formation of F-3 with N-substituted-L-Pro-OH, followed by dehydration, affords bis-oxazole F-5, which can be further transformed to give various analogs bearing different R groups through a sequence of typical de-protection and amide formation steps. Moreover, N-substituted -L-Pro-OH can be replaced with other N-substituted D- or L-amino acids to generate bis-oxazole analogs of F-5.

Scheme G

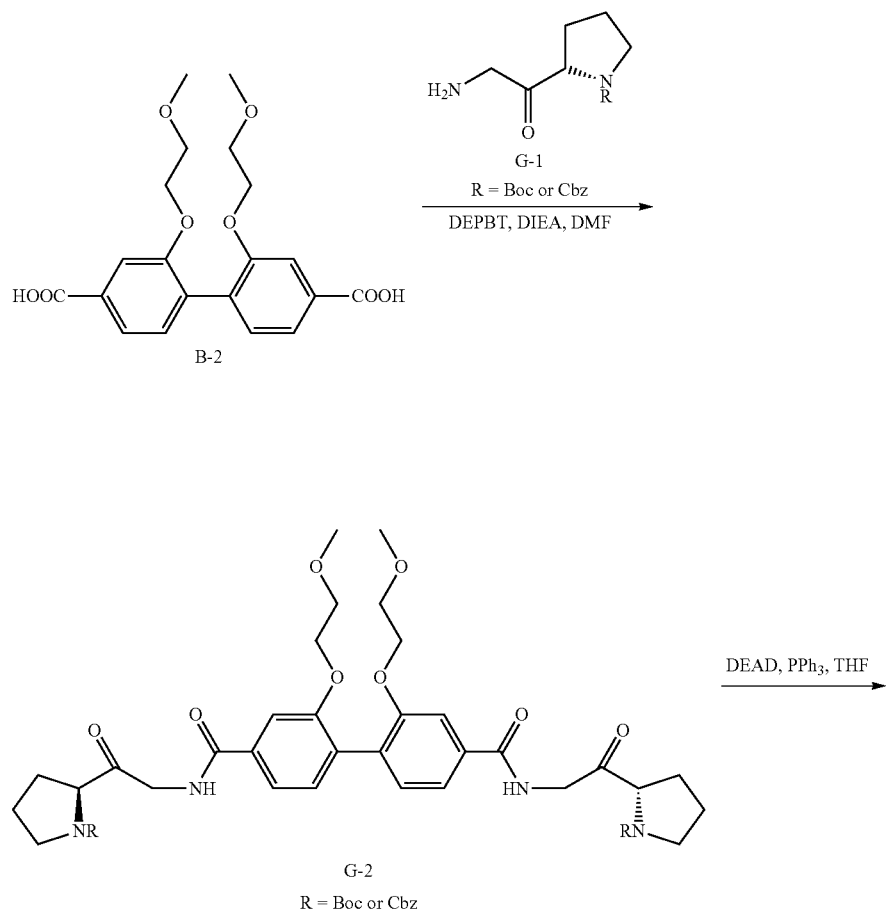

G-2

R = Boc or Cbz

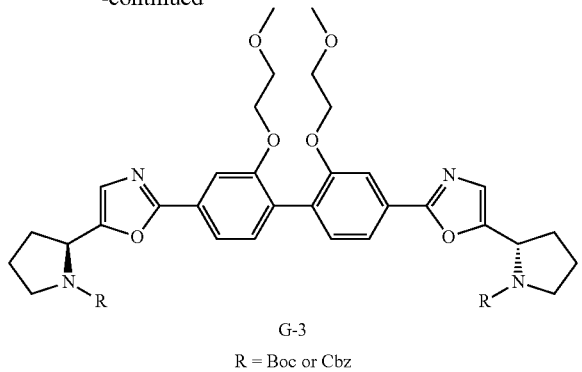

G-3

R = Boc or Cbz

As outlined in Scheme G, the regioisomer of F-5 with respect to the substitution pattern on the oxazole moiety is prepared. Amide formation of bis-carboxylic acid B-2 with (S)-2-amino-1-(pyrrolidin-2-yl)ethanone (G-1), followed by dehydration, gives bis-oxazole G-3, which can be further transformed to give various analogs bearing different R groups through a sequence of typical de-protection and amide formation steps. Moreover, (S)-2-amino-1-(pyrrolidin-2-yl)ethanone (G-1) can be replaced with other α-amino ketones derived from N-substituted D- or L-amino acids to generate bis-oxazole analogs of G-3.

The following schemes exemplify some of the synthetic routes that are used for the preparation of compounds and their analogs included in this invention. Those skilled in the art will understand that alternative routes may also be used to reach the same and similarly functionalized intermediates and target molecules. Alternative reagents for a given transformation are also possible.

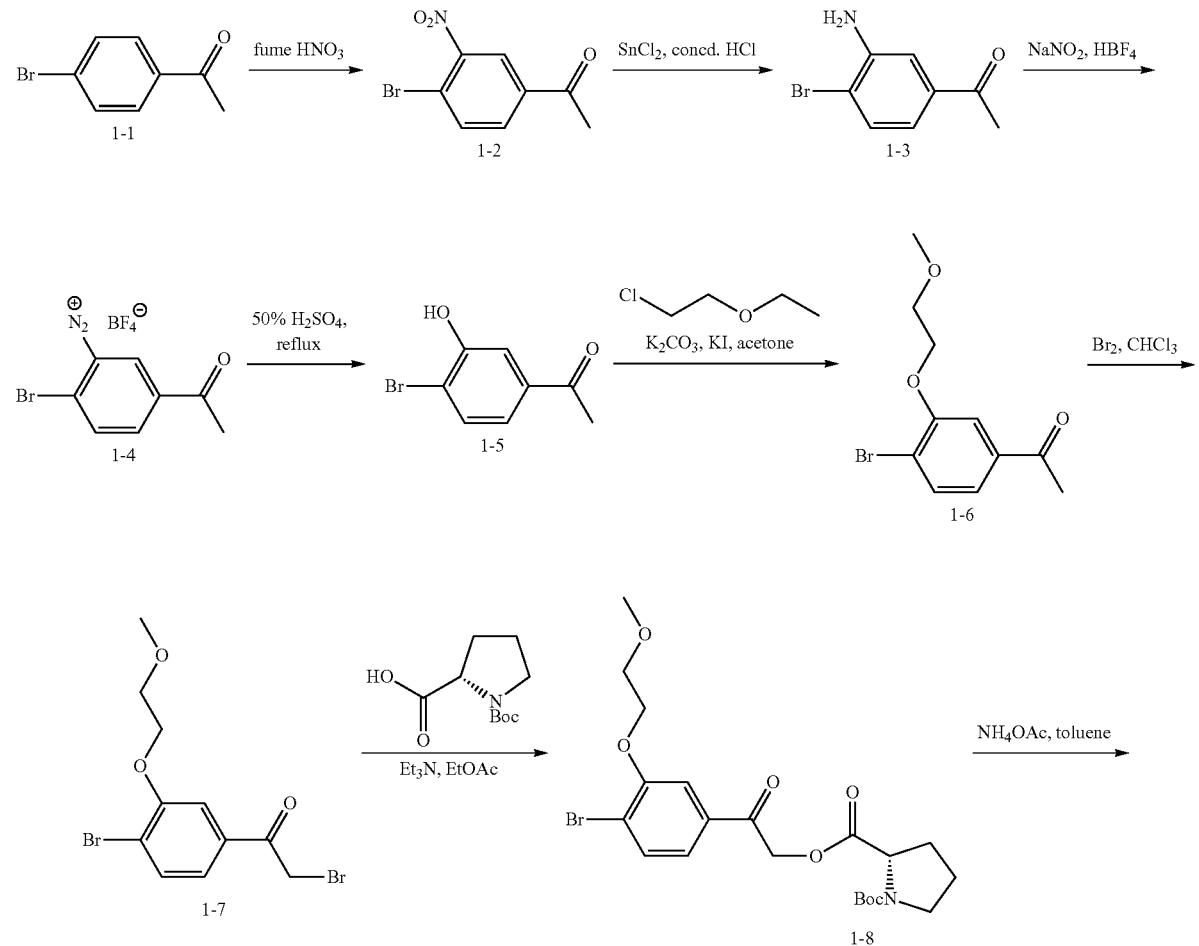

Scheme 1

-continued
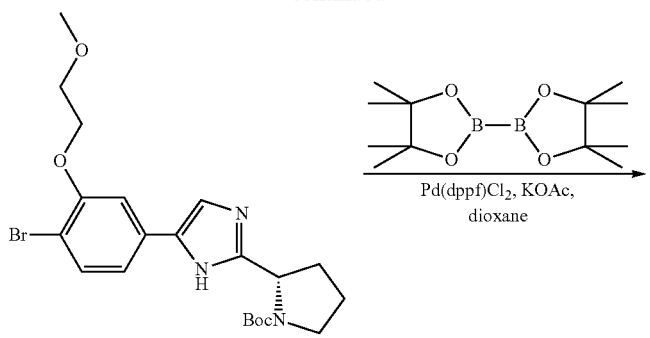
1-9
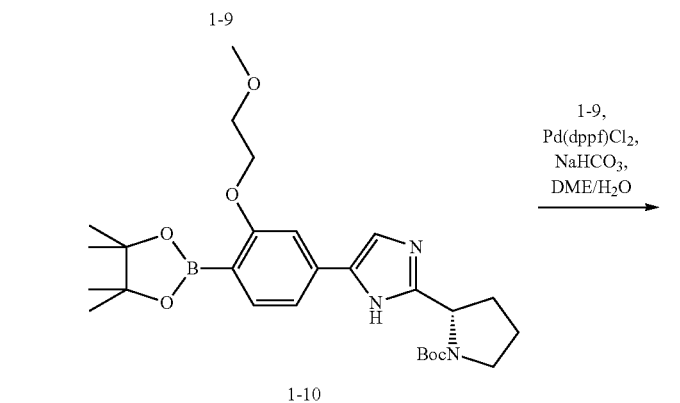
1-10
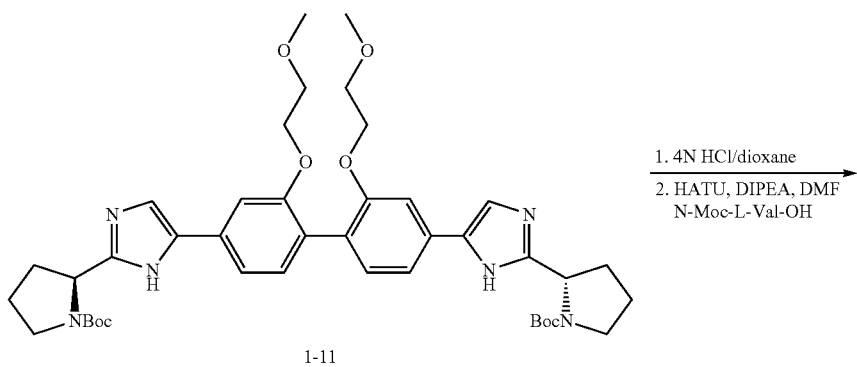
1-11
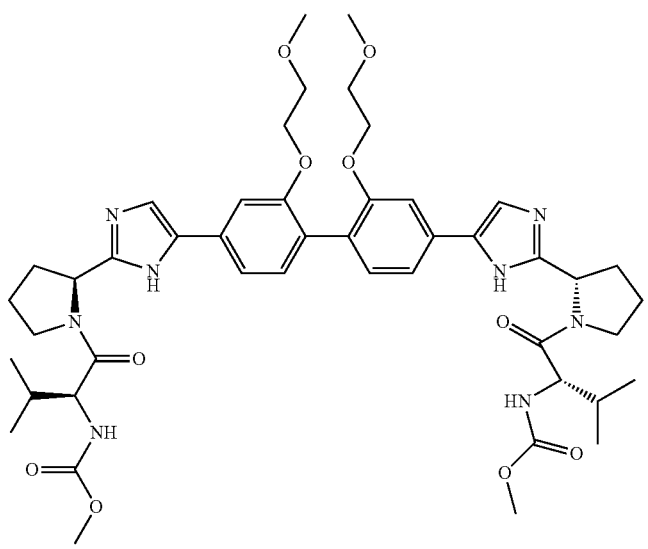
1-12

Example 1

Synthesis of 1-12, dimethyl(2S,2'S)-1,1'-((2S,2'S)-2,2'-(5,5'-(2,2'-bis(2-methoxyethoxy)biphenyl-4,4'-diyl)bis(1H-imidazole-5,2-diyl))bis(pyrrolidine-2,1-diyl))bis(3-methyl-1-oxobutane-2,1-diyl)dicarbamate as shown in Scheme 1

Step 1. Preparation of 1-2. To fuming nitric acid (200 mL), 1-(4-bromophenyl)-1-propanone (1-1) (40 g, 0.20 mol) was added while keeping the inside temperature of mixture at 5 to 10° C. The reaction solution was stirred at this temperature for 30 minutes and then poured into ice. The precipitate was collected by filtration, washed with distilled water (25 mL×2) and re-crystallized from methanol to give 1-2 (18 g, 37% yield). $^1$H NMR (500 MHz, CDCl$_3$) δ 8.38 (1H, d, J=2.0 Hz), 7.99 (1H, dd, J=8.2 Hz, 2.0 Hz), 7.86 (1H, d, J=8.2 Hz), 3.01 (2H, q, J=7.1 Hz), 1.25 (3H, t, J=7.1 Hz) ppm; LC-MS (ESI): m/z 244.0 (M+H)$^+$.

Step 2. Preparation of 1-3. To a solution of 4-bromo-3-nitroacetophenone (1-2) (5.0 g, 20.5 mmol) in 890 mL of methanol were added tin (II) chloride (19.4 g, 0.1 mol) and 17 mL of concentrated hydrochloric acid. After stirring at rt for 3.5 h, the reaction mixture was neutralized with 470 mL of saturated aqueous NaHCO$_3$. The precipitate was filtered off and the filtrate was extracted with ethyl acetate (2×150 mL). The organic extracts were combined, washed with water (35 mL) and brine (20 mL) and dried over anhydrous Na$_2$SO$_4$. The solvent was removed and the residue was dried in vacuo to give crude 1-3 (3.97 g, 90% yield). LC-MS (ESI): m/z 214.0 (M+H)$^+$.

Step 3. Preparation of 1-4. To a solution of 1-3 (1.07 g, 5.0 mmol) in H$_2$O (5 mL) was added NaNO$_2$ (0.69 g, 10.0 mmol), followed by HBF$_4$ (1 mL). After stirring at 0° C. for 1 h, the reaction mixture was filtered. The solid was washed with cold water and dried in vacuo to give 1-4 (1.35 g, 95% yield) as an orange solid. LC-MS (ESI): m/z 226.0 (M+H)$^+$.

Step 4. Preparation of 1-5. To a solution of 1-4 (5.0 g, 15 mmol) in H$_2$O (10 mL) was added 50% H$_2$SO$_4$ (65 mL). After refluxing for 30 min under an atmosphere of Ar, the reaction mixture was cooled to rt and extracted with EtOAc (100 mL×2). The combined organic extracts were washed with brine and dried over anhydrous Na$_2$SO$_4$. The solvent was removed and the residue was purified by silica gel column chromatography (Petroleum ether/EtOAc=2/1 (v/v)) to give 1-5 (2.5 g, 61% yield) as a white solid. $^1$H NMR (500 MHz, CDCl$_3$) δ7.60-7.57 (m, 2H), 7.40 (dd, 1H, J=8.0 Hz, 2.0 Hz), 5.79 (s, 1H), 2.58 (s, 3H) ppm. LC-MS (ESI): m/z 215.0 (M+H)$^+$.

Step 5. General Procedure A. Preparation of 1-6. To a solution of 1-5 (2.15 g, 10.0 mmol) in acetone (50 mL) were added K$_2$CO$_3$ (2.76 g, 20.0 mmol), 1-chloro-2-methoxyethane (1.88 g, 20.0 mmol) and KI (0.83 g, 5.0 mmol). After stirring at 75° C. for 96 h, the reaction mixture was filtered through CELITE™545 and the filtered cake was washed with EtOAc (50 mL×2). The filtrate was concentrated and the residue was purified by silica gel column chromatography (Petroleum ether/acetone=2/1 (v/v)) to give 1-6 (1.4 g, 51% yield) as yellow oil. $^1$H NMR (500 MHz, CDCl$_3$) δ7.63 (d, 1H, J=8.5 Hz), 7.51 (d, 1H, J=2.0 Hz), 7.41 (dd, 1H, J=8.0 Hz, 2.0 Hz), 4.25 (t, 2H, J=4.5 Hz), 3.83 (t, 2H, J=4.5 Hz), 3.49 (s, 3H), 2.59 (s, 3H) ppm. LC-MS (ESI): m/z 273.0 (M+H)$^+$.

Step 6. General Procedure B. Preparation of 1-7. To a solution of 1-6 (274 mg, 1.0 mmol) in CHCl$_3$ (20 mL) was added a solution of Br$_2$ (160 mg, 1.0 mmol) in CHCl$_3$ (1 mL). After stirring at rt for 2 h, the reaction mixture was diluted with water (30 mL). The organic layer was washed with aq. NaHCO$_3$, brine and dried with anhydrous Na$_2$SO$_4$. The solvent was removed and the residue was dried in vacuo to give crude 1-7 (370 mg, quantitative yield). LC-MS (ESI): m/z 350.9 (M+H)$^+$.

Step 8. General Procedure C. Preparation of 1-8. To a stirred solution of 1-7 (352 mg, 1.00 mmol) in 20 mL of AcOEt were added N-Boc-L-Pro-OH (237 mg, 1.1 mmol) and Et$_3$N (0.15 mL, 1.1 mmol). After stirring at rt for 2 h, the reaction mixture was washed with sat. NH$_4$Cl and dried with anhydrous Na$_2$SO$_4$. The solvent was removed and the residue was dried in vacuo to give crude 1-8 (487 mg), which was used for the next step without further purification. LC-MS (ESI): m/z 486.1 (M+H)$^+$.

Step 9. General Procedure D. Preparation of 1-9. To a stirred solution of 1-8 (487 mg, 1.0 mmol) in 10 mL toluene was added NH$_4$OAc (770 mg, 10.0 mmol) in a sealed tube. After refluxing for 12 h, the reaction mixture was cooled to rt and filtered through Celite° 545 and the filtered cake was washed with EtOAc (50 mL×2). The filtrate was washed with brine and dried with anhydrous Na$_2$SO$_4$. The solvent was removed and the residue was purified by silica gel column chromatography (PE/EtOAc=2/1 (v/v)) to give 1-9 (200 mg, 37% yield) as a yellowish solid. $^1$H NMR (500 MHz, CDCl$_3$) δ8.53 (brs, 1H), 7.49 (d, 1H, J=8.0 Hz), 7.22 (s, 1H), 7.14 (brs, 1H), 4.96 (brs, 1H), 4.25 (s, 2H), 3.84 (t, 2H, J=4.0 Hz), 3.75-3.71 (m, 2H), 3.51 (s, 3H), 3.41 (s, 3H), 2.16-1.97 (m, 4H), 1.40 (s, 9H) ppm. LC-MS (ESI): m/z 466.1 (M+H)$^+$.

Step 10. General Procedure E. Preparation of 1-10. To a stirred solution of 1-9 (364 mg, 1.0 mmol) in 15 mL dioxane was added 4,4,4',4',5,5,5',5'-octamethyl-2,2'-bi(1,3,2-dioxaborolane) (504 mg, 2.00 mmol), KOAc (294 mg, 3.0 mmol) and Pd(dppf)Cl$_2$ (81 mg, 0.10 mmol). After refluxing under an atmosphere of N$_2$, the reaction mixture was cooled to rt and filtered through Celite° 545 and the filtered cake was washed with EtOAc (50 mL×2). The filtrate was washed with brine and dried with anhydrous Na$_2$SO$_4$. The solvent was removed and the residue was purified by silica gel column chromatography (PE/EtOAc=2/1 (v/v)) to give 1-10 (250 mg, 49% yield). LC-MS (ESI): m/z 514.3 (M+H)$^+$.

Step 11. General Procedure F. Preparation of 1-11. To a stirred solution of 1-9 (228 mg, 0.49 mmol) and 1-10 (0.25 g, 0.49 mmol) in 20 mL DME and 10 mL H$_2$O were added NaHCO$_3$ (168 mg, 2.00 mmol) and Pd(dppf)Cl$_2$ (40 mg, 0.049 mmol). After refluxing under an atmosphere of N$_2$, the reaction mixture was cooled to rt and filtered through CELITE™545 and the filtered cake was washed with EtOAc (50 mL×2). The filtrate was washed with brine and dried with anhydrous Na$_2$SO$_4$. The solvent was removed and the residue was purified by silica gel column chromatography (PE/EtOAc=2/1 (v/v)) to give 1-11 (120 mg, 32% yield). $^1$H NMR (500 MHz, MeOH-d$_4$): δ 7.44-7.28 (m, 8H), 4.21 (s, 4H), 3.73-3.69 (m, 5H), 3.57-3.55 (m, 2H), 3.35 (s, 9H), 2.44-2.43 (m, 2H), 2.10-1.98 (m, 6H), 1.52 (s, 6H), 1.30 (s, 12H) ppm. LC-MS (ESI): m/z 773.4 (M+H)$^+$.

Step 12. General Procedure G. Preparation of 1-12. To a stirred solution of 1-11 (120 mg, 0.160 mmol) in dioxane (2 mL) was added 4N HCl in dioxane (2 mL). After stirring at rt overnight, the reaction mixture was concentrated and the residue was dried in vacuo to give an HCl salt, which was used directly for the next step without further purification. LC-MS (ESI): m/z 573 (M+H)$^+$. Subsequently, to the HCl salt were sequentially added DMF (4 mL), DIPEA (0.25 mL, 1.6 mmol), N-Moc-L-Val-OH (68 mg, 0.39 mmol) and HATU (147 mg, 0.390 mmol). After stirring at rt for 30 min, the reaction mixture was slowly added into water. The solid was collected, filtered and then purified by preparative HPLC to give 1-12 (50 mg, 34% yield) as an off-white solid. $^1$H NMR (500 MHz, CD$_3$OD) δ7.93 (s, 1H), 7.44-7.37 (m, 6H), 5.27-5.24 (m, 2H), 4.24 (d, 1H, J=7.0), 4.21 (s, 4H), 4.21-4.11 (m, 2H), 3.93-3.91 (m, 2H), 3.66 (s, 10H), 3.27 (s, 6H), 2.57 (s, 2H), 2.31-2.29 (m, 2H), 2.22-1.20 (m, 3H), 2.09-1.06 (m, 2H), 0.95-0.90 (m, 12H) ppm; LC-MS (ESI): m/z 887.5 (M+H)$^+$.
Scheme 2
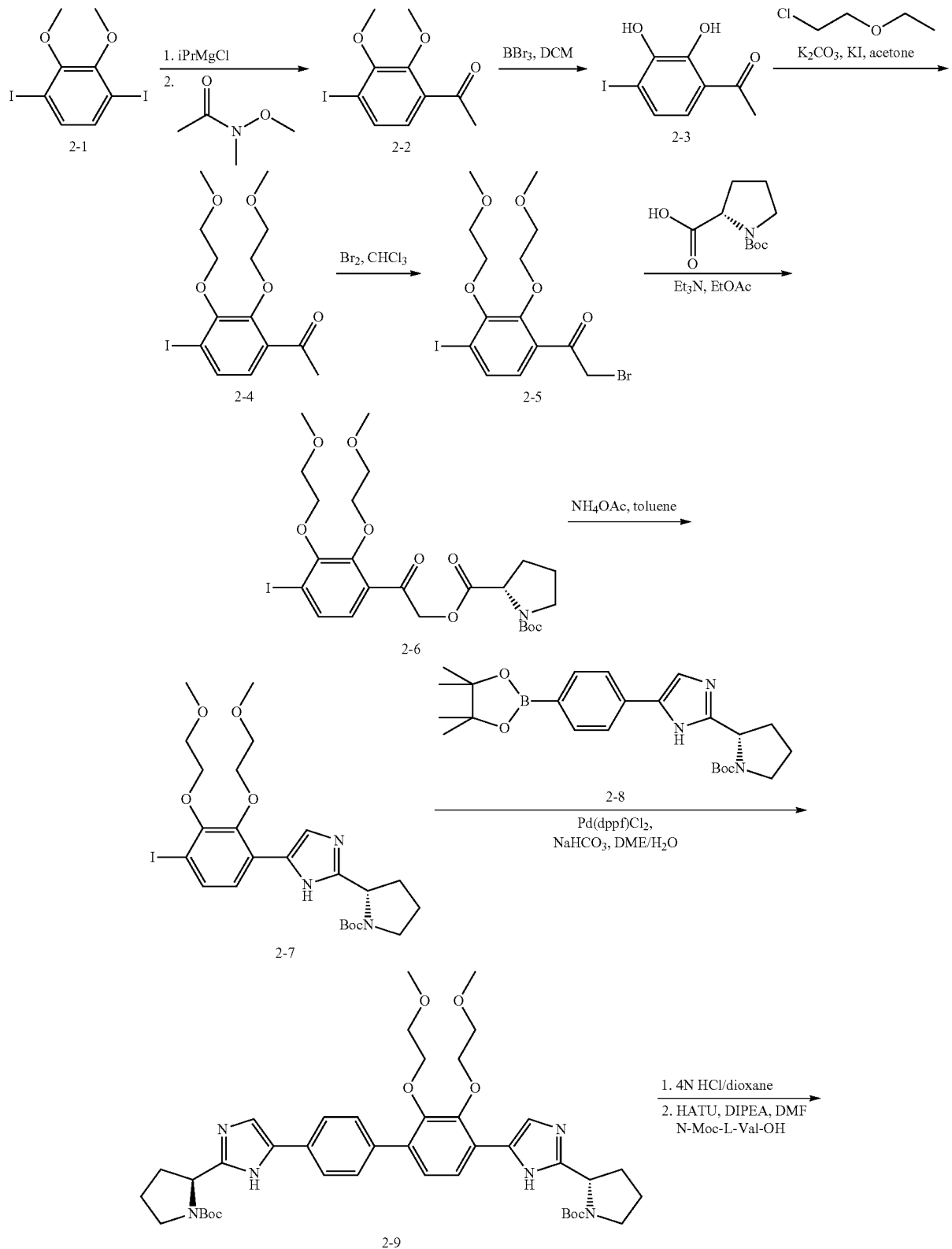

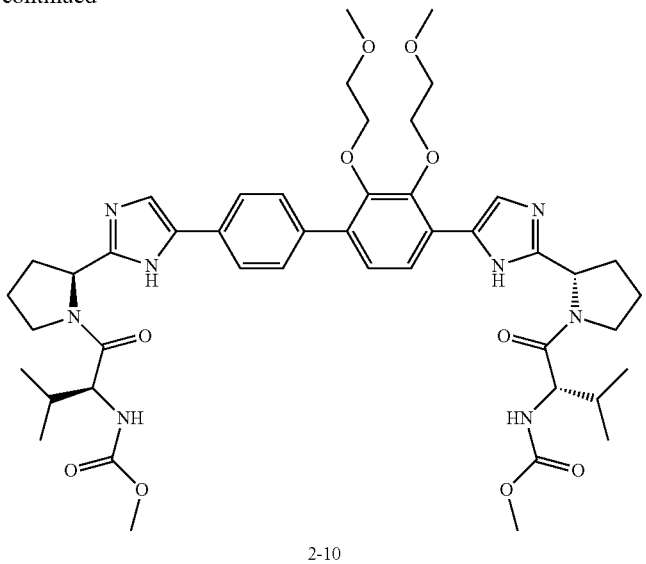

2-10

Example 2

Synthesis of 2-10, dimethyl(2S,2'S)-1,1'-((2S,2'S)-2,2'-(5,5'-(2,3-bis(2-methoxyethoxy)biphenyl-4,4'-diyl)bis(1H-imidazole-5,2-diyl))bis(pyrrolidine-2,1-diyl))bis(3-methyl-1-oxobutane-2,1-diyl)dicarbamate as shown Scheme 2

Step 1. Preparation of 2-2. To a solution of 2-1 (2.45 g, 6.3 mmol) in THF (20 mL) was slowly added 2.0M i-PrMgCl in Et$_2$O (3.2 mL) at −78° C. After stirring at −78° C. for 1 h, the reaction mixture was added N-methoxy-N-methylacetamide (779 mg, 7.6 mmol). Subsequently, the mixture was slowly warmed up to rt and diluted with EtOAc (100 mL). The mixture was washed with water (20 mL×3) and dried with anhydrous Na$_2$SO$_4$. The solvent was removed and the residue was purified by silica gel column chromatography (Petroleum ether/EtOAc=10/1 (v/v)) to give 2-2 (1.25 g, 65% yield). $^1$H NMR (CDCl$_3$, 500 MHz): δ 7.56 (d, 1H, J=10.0 Hz), 7.16 (d, 1H, J=10.5 Hz), 3.95 (s, 3H), 3.88 (s, 3H), 2.61 (s, 3H) ppm; LC-MS (ESI): m/z 307.0 [M+H]$^+$.

Step 2. Preparation of 2-3. To a solution of 2-2 (1.0 g, 3.3 mmol) in dichloromethane (20 mL) was slowly added 4N BBr$_3$ in DCM (4.9 mL) at 0° C. After stirring at rt for 30 min, the reaction was quenched by adding H$_2$O (20 mL). The organic layer was separated and dried with anhydrous MgSO$_4$. The solvent was removed and the residue was purified by silica gel column chromatography (PE/acetone=10/1 (v/v)) to give 2-3 (800 mg, 88% yield). $^1$H NMR (DMSO, 500 MHz): δ12.52 (s, 1H), 9.96 (s, 1H), 7.30 (d, 1H, J=8.5 Hz), 7.19 (d, 1H, J=9.0 Hz), 2.62 (s, 3H) ppm; LC-MS (ESI): m/z 278.9 [M+H]$^+$.

Step 3. Preparation of 2-4. Treatment of 2-3 under the conditions of general procedure A afforded 2-4 (651 mg, 57% yield). $^1$H NMR (CDCl$_3$, 500 MHz): δ 7.57 (d, 1H, J=8.0 Hz), 7.21 (d, 1H, J=8.0 Hz), 4.28 (t, 2H, J=5.0 Hz), 4.19 (t, 2H, J=4.0 Hz), 3.80 (t, 2H, J=5.0 Hz), 3.63 (t, 2H, J=4.5 Hz), 3.47 (s, 3H), 3.35 (s, 3H), 2.65 (s, 3H) ppm; LC-MS (ESI): m/z 395.0 [M+H]$^+$.

Step 4. Preparation of 2-5. Treatment of 2-4 under the conditions of general procedure B afforded 2-5. LC-MS (ESI): m/z 472.9 [M+H]$^+$.

Step 5. Preparation of 2-6. Treatment of 2-5 under the conditions of general procedure C afforded 2-6. LC-MS (ESI): m/z 608.1 [M+H]$^+$.

Step 6. Preparation of 2-7. Treatment of 2-6 under the conditions of general procedure D afforded 2-7 in 35% yield (three steps from 2-4). $^1$H NMR (400 MHz, CDCl$_3$) δ7.60-7.49 (m, 3H), 4.96 (d, 1H, J=4.8 Hz), 4.34-4.30 (m, 2H), 4.23-4.10 (m, 2H), 3.80-3.71 (m, 4H), 3.46 (s, 5H), 3.41 (s, 3H), 2.30-2.16 (m, 2H), 1.94-1.91 (m, 2H), 1.48 (s, 9H) ppm. LC-MS (ESI): m/z 588.1 [M+H]$^+$.

Step 7. Preparation of 2-9. Treatment of 2-7 and 2-8 (prepared according to US 2008/0044380) under the conditions of general procedure F afforded 2-9 in 76% yield. $^1$H NMR (400 MHz, CDCl$_3$) δ7.82 (brs, 2H), 7.62 (d, 3H, J=6.0 Hz), 7.52-7.46 (m, 1H), 7.40 (s, 1H), 7.17 (d, 1H, J=8.0 Hz), 5.00 (d, 2H, J=4.8 Hz), 4.48 (brs, 1H), 4.35 (brs, 1H), 3.88-3.83 (m, 5H), 3.53 (brs, 2H), 3.44 (d, 8H, J=7.3 Hz), 3.25 (d, 3H, J=9.2 Hz), 3.06 (brs, 1H), 2.58 (brs, 1H), 2.31-2.14 (m, 4H), 2.02-1.99 (m, 3H), 1.51 (d, 18H, J=10.0 Hz) ppm. LC-MS (ESI): m/z 773.4 [M+H]$^+$.

Step 8. Preparation of 2-10. Treatment of 2-9 under the conditions of general procedure G afforded 2-9 in 30% yield. LC-MS (ESI): m/z 887.5 [M+H]$^+$.

Example 3

Preparation of 2-9A, (S)-tert-butyl 2-(5-(4'-(2-((S)-1-(tert-butoxycarbonylamino)ethyl)-1H-imidazol-5-yl)-2,3-bis(2-methoxyethoxy)biphenyl-4-yl)-1H-imidazole-2-yl)pyrrolidine-1-carboxylate

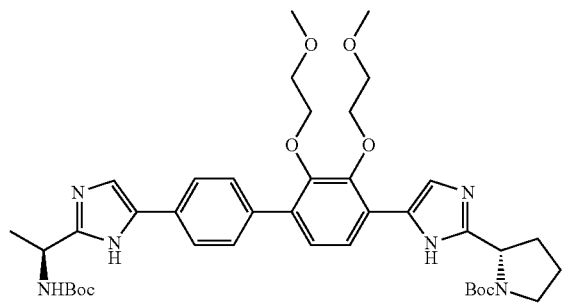

2-9A

Following general procedure F described above for synthesis of 2-9 and replacing (S)-tert-butyl 2-(5-(4-(4,4,5,5-tetramethyl-1,3,2-dioxaborolan-2-yl)phenyl)-1H-imidazol-2-yl)pyrrolidine-1-carboxylate (2-8) with (S)-tert-butyl 2-(5-(4-(4,4,5,5-tetramethyl-1,3,2-dioxaborolan-2-yl)phenyl)-1H-imidazol-2-yl)ethylcarbamate, compound 2-9A was obtained in 62% yield. LC-MS (ESI): m/z 747.4 [M+H]⁺.

Example 4

Preparation of 2-10A

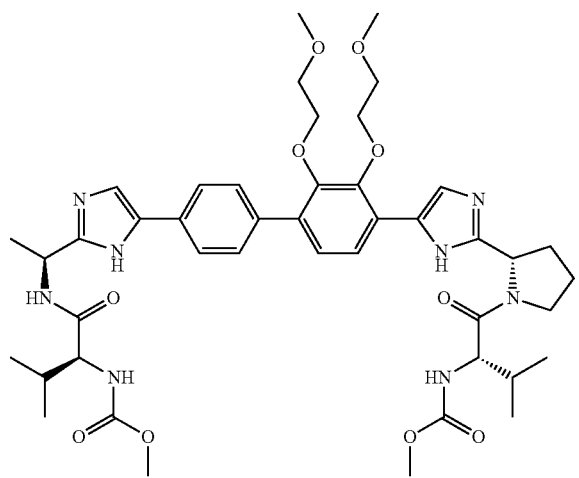

2-10A

Following general procedure G and replacing compound 2-9 with 2-9A, compound 2-10A was obtained. LC-MS (ESI): m/z 861.4 [M+H]⁺.

Example 5

Preparation of 2-9B, (R)-tert-butyl 4-(5-(4'-(2-((S)-1-(tert-butoxycarbonyl)pyrrolidin-2-yl)-1H-imidazol-5-yl)-2',3'-bis(2-methoxyethoxy)biphenyl-4-yl)-1H-imidazole-2-yl)thiazolidine-3-carboxylate

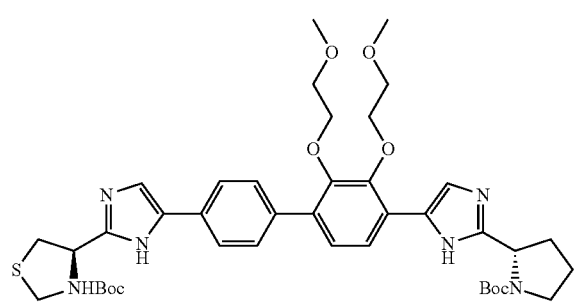

2-9B

Following general procedure F described above for synthesis of 2-9 and replacing (S)-tert-butyl 2-(5-(4-(4,4,5,5-tetramethyl-1,3,2-dioxaborolan-2-yl)phenyl)-1H-imidazol-2-yl)pyrrolidine-1-carboxylate (2-8) with (R)-tert-butyl 4-(5-(4-(4,4,5,5-tetramethyl-1,3,2-dioxaborolan-2-yl)phenyl)-1H-imidazol-2-yl)thiazolidine-3-carboxylate, compound 2-9B was obtained in 28% yield. LC-MS (ESI): m/z 791.4 [M+H]⁺.

Example 6

Preparation of 2-10B

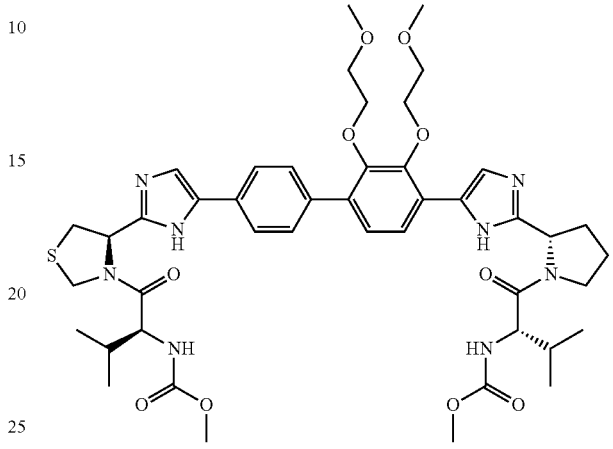

2-10B

Following general procedure G and replacing compound 2-9 with 2-9B, compound 2-10B was obtained. LC-MS (ESI): m/z 905.4 [M+H]⁺.

Example 7

Preparation of 2-9C, (R)-tert-butyl 3-(5-(4'-(2-((S)-1-(tert-butoxycarbonyl)pyrrolidin-2-yl)-1H-imidazol-5-yl)-2',3'-bis(2-methoxyethoxy)biphenyl-4-yl)-1H-imidazole-2-yl)morpholine-4-carboxylate

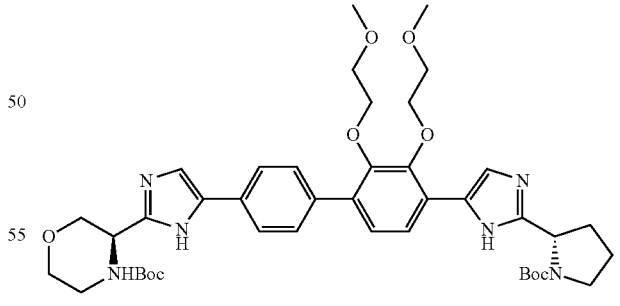

2-9C

Following general procedure F described above for synthesis of 2-9 and replacing (S)-tert-butyl 2-(5-(4-(4,4,5,5-tetramethyl-1,3,2-dioxaborolan-2-yl)phenyl)-1H-imidazol-2-yl)pyrrolidine-1-carboxylate (2-8) with (R)-tert-butyl 3-(5-(4-(4,4,5,5-tetramethyl-1,3,2-dioxaborolan-2-yl)phenyl)-1H-imidazol-2-yl)morpholine-4-carboxylate, compound 2-9C was obtained in 70% yield. LC-MS (ESI): m/z 789.4 [M+H]⁺.

Example 8
Preparation of 2-10C

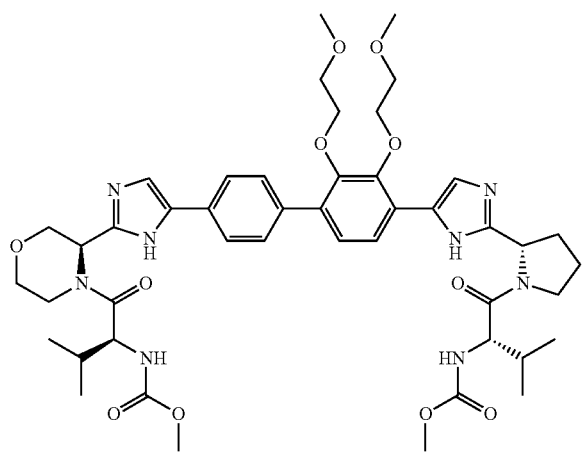

Following general procedure G and replacing compound 2-9 with 2-9C, compound 2-10C was obtained. LC-MS (ESI): m/z 903.5 [M+H]$^+$. Spectroscopic data of the HCl salt of De-Boc-2-9c, which was obtained by treating 2-9c with 4N HCl in dioxane: $^1$H NMR (500 MHz, MeOD-d$_4$) δ 8.37 (s, 1H), 8.09 (s, 1H), 7.96 (d, 2H, J=8.0 Hz), 7.80 (d, 2H, J=8.5 Hz), 7.74 (d, 1H, J=8.0 Hz), 7.38 (d, 1H, J=8.0 Hz), 5.24 (t, 1H, J=8.5 Hz), 5.10-5.08 (m, 1H), 4.44 (d, 2H, J=2.5 Hz), 4.42-4.33 (m, 2H), 4.13-4.12 (m, 2H), 3.93 (t, 2H, J=4.0 Hz), 3.78 (d, 2H, J=3.0 Hz), 3.66-3.57 (m, 3H), 3.51-3.50 (m, 2H), 3.46-3.44 (m, 5H), 3.21 (s, 3H), 2.77-2.74 (m, 1H), 2.60-2.56 (m, 1H), 2.43-2.41 (m, 1H), 2.29-2.25 (m, 1H) ppm. LC-MS (ESI): m/z 589.3 [M+H]$^+$.

Scheme 3

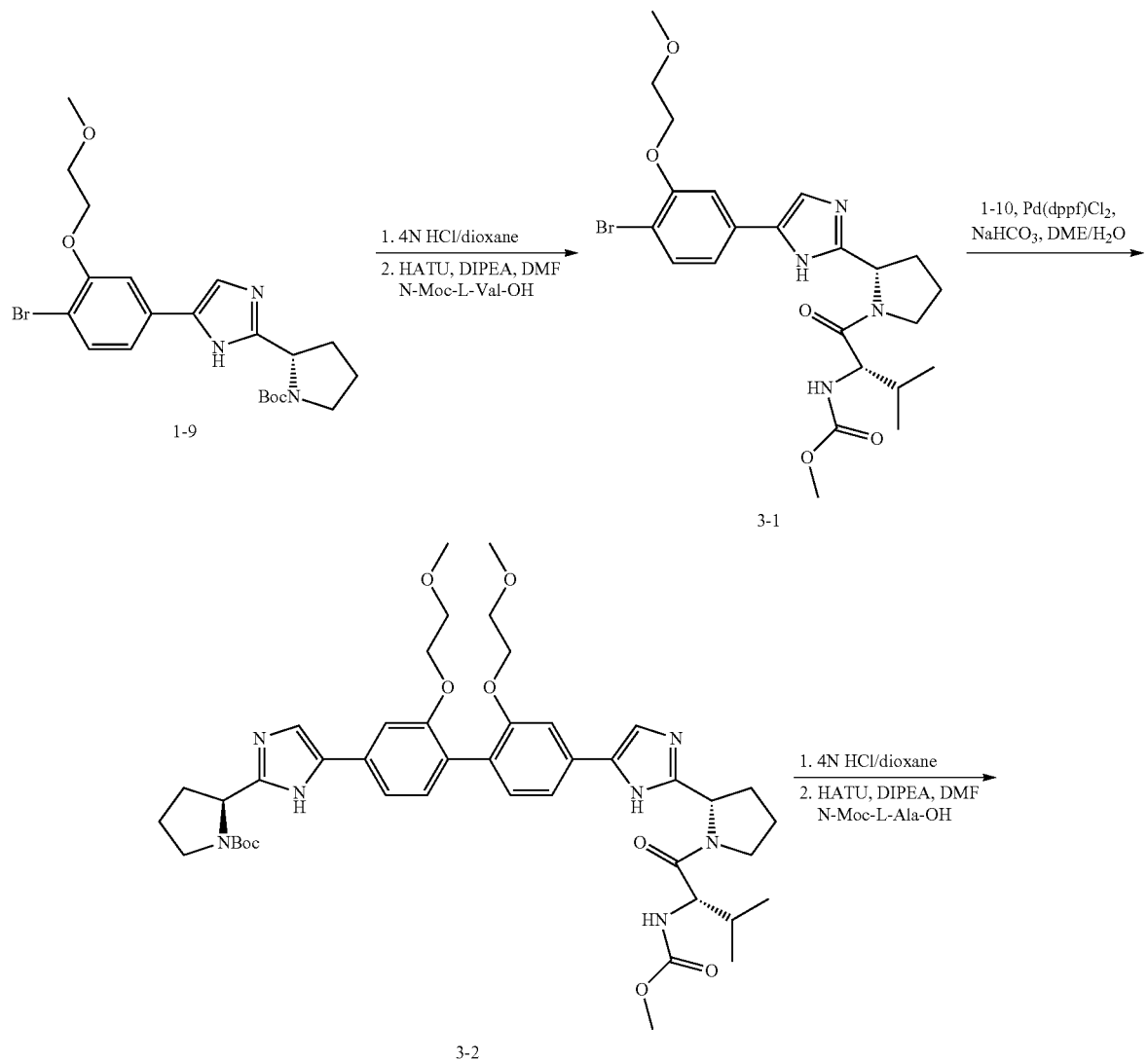

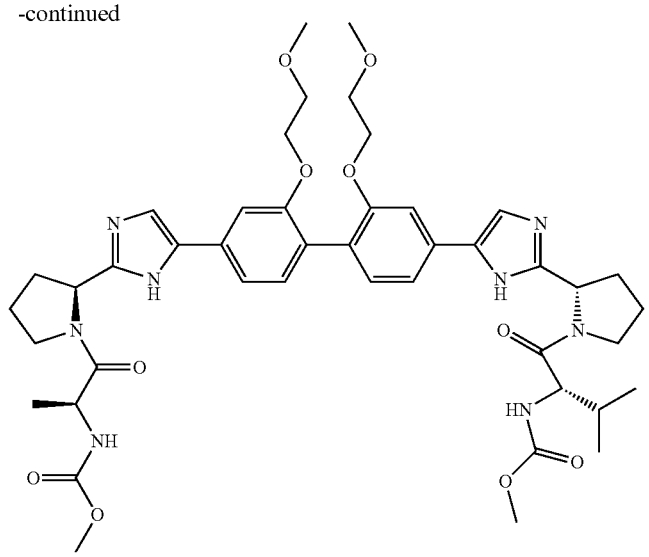

3-3

Example 9

Preparation of 3-3 as described in Scheme 3

Step 1. Preparation of 3-1. Following general procedure G and replacing compound 1-11 with 1-9, compound 3-1 was obtained in 70% yield. $^1$H NMR (500 MHz, CDCl$_3$) δppm 7.48 (d, 1H, J=8.5 Hz), 7.32-7.25 (m, 1H), 7.20 (s, 1H), 7.12 (brs, 1H), 5.39 (d, 1H, J=9.0 Hz), 5.24 (d, 1H, J=4.5 Hz), 4.33 (brs, 1H), 4.25 (t, 2H, J=4.5 Hz), 3.84-3.83 (m, 3H), 3.70 (s, 3H), 3.60 (brs, 1H), 3.51 (s, 3H), 3.01 (brs, 1H), 2.35-1.98 (m, 5H), 0.88-0.85 (m, 6H). LC-MS (ESI): m/z 523.1 [M+H]$^+$.

Step 2. Preparation of 3-2. Following general procedure F and replacing compound 1-9 with 3-1, compound 3-2 was obtained in 60% yield. LC-MS (ESI): m/z 830.4 [M+H]$^+$.

Step 3. Preparation of 3-3. Following general procedure G and replacing compound 1-11 with 3-2 and N-Moc-L-Val-OH with N-Moc-L-Ala-OH, compound 3-3 was obtained. LC-MS (ESI): m/z 859.4 [M+H]$^+$. Spectroscopic data of the HCl salt of De-Boc-3-2, which was obtained by treating 3-2 with 4N HCl in dioxane: $^1$H NMR (500 MHz, MeOD) δ8.16 (brs, 1H), 7.96 (s, 1H), 7.62 (s, 1H), 7.51-7.40 (m, 5H), 5.27-5.26 (m, 2H), 4.27-4.23 (m, 5H), 4.13 (brs, 1H), 3.98-3.92 (m, 1H), 3.68 (s, 8H), 3.32 (s, 4H), 2.60-2.09 (m, 8H), 0.96 (d, 3H, J=6.5 Hz), 0.92 (d, 3H, J=6.5 Hz) ppm. LC-MS (ESI): m/z 730.4 [M+H]$^+$.

Scheme 4

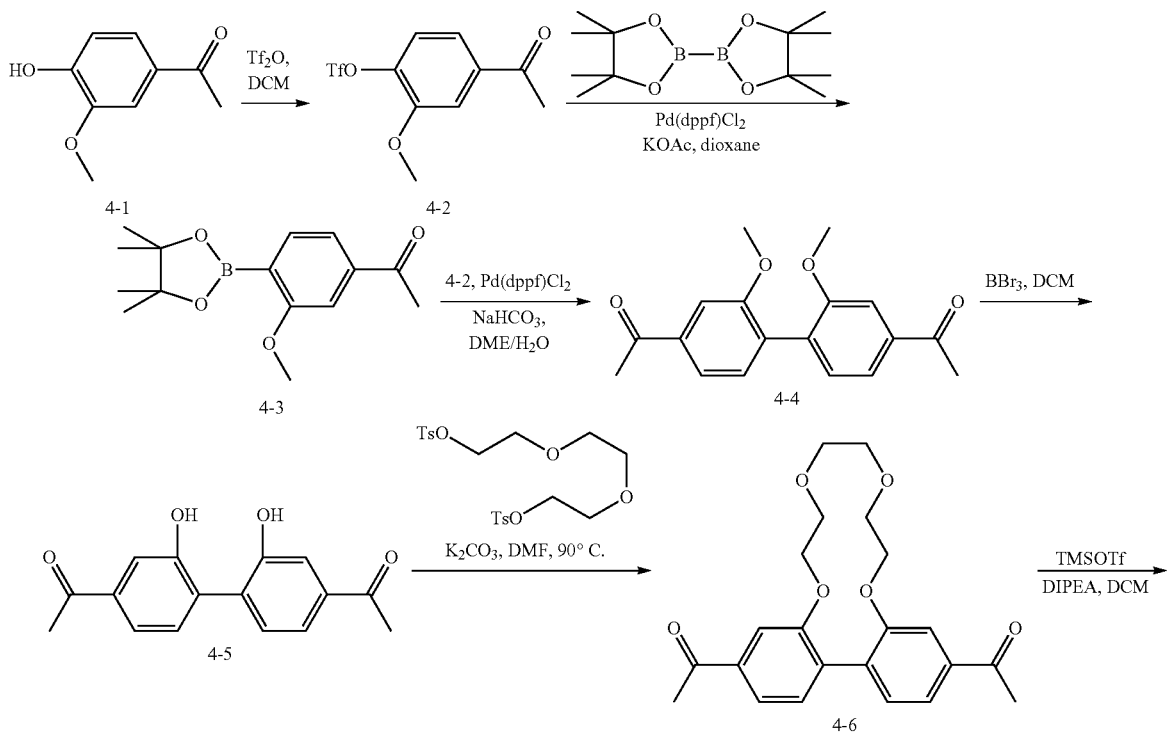

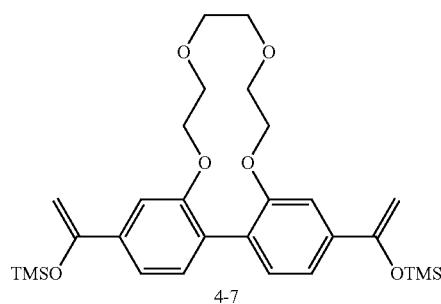

-continued

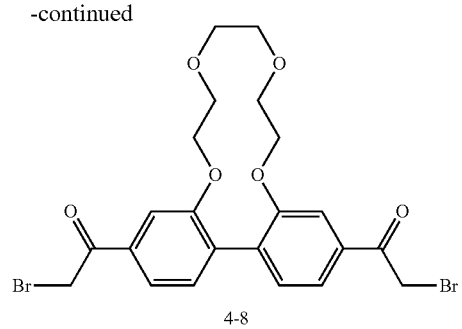

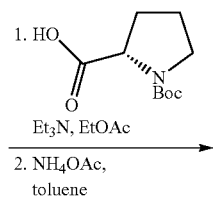

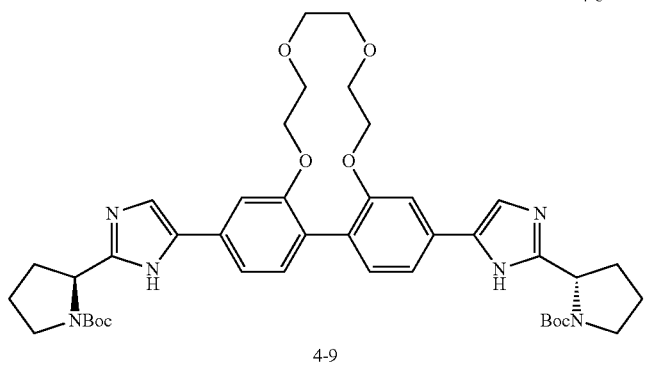

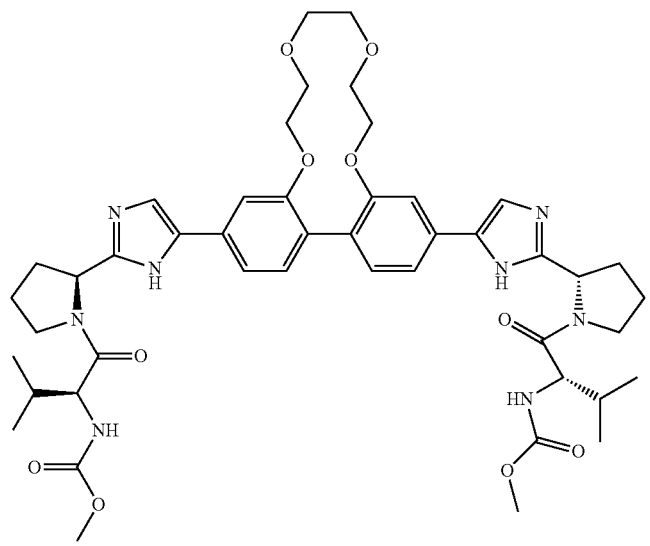

Example 10

Synthesis of 4-10, dimethyl(2S,2'S)-1,1'-((2S,2'S)-2,2'-(5,5'-(2,2'-(5,5'-(6,7,9,10,12,13-hexahydrodibenzo[k,m][1,4,7,10]tetraoxacyclotetradecine-3,16-diyl)bis(1H-imidazole-5,2-diyl))bis(pyrrolidine-2,1-diyl))bis(3-methyl-1-oxobutane-2,1-diyl)dicarbamate as shown in Scheme 4

Step 1. Preparation of 4-2. To a solution of 4-1 (50.0 g, 301 mmol) and Et$_3$N (210 mL) in 750 mL DCM was dropwisely added Tf$_2$O (150 mL, 903 mmol) at 0° C. After stirring at 0° C. for 1 h and then at r.t for 3 hrs, the reaction mixture was concentrated and the residue was purified by silica gel column chromatography (PE/EtOAc=30:1 (v/v) to 5:1 (v/v)) to give 4-2 (56 g, 62% yield) as a white solid. $^1$H NMR (400 MHz, CDCl$_3$): δ 7.66 (d, 1H, J=2.4 Hz), 7.57 (dd, 1H, J=1.6 Hz, 8.4 Hz), 7.32 (d, 1H, J=8.4 Hz), 3.99 (s, 3H), 2.63 (s, 3H). $^{19}$F NMR (376 MHz, CDCl$_3$): δ-73.76 (s, 3F) ppm. LC-MS (ESI) m/z 299.0 [M+H]$^+$.

Step 2. Preparation of 4-3. Following general procedure E and replacing compound 1-9 with 4-2, compound 4-3 was obtained (10.5 g, 94% yield). LC-MS (ESI): m/z 277.2 [M+H]$^+$.

Step 3. Preparation of 4-4. Following general procedure F and replacing compound 1-10 with 4-4, compound 4-4 was obtained (8.9 g, 90% yield) as a yellow solid. $^1$H NMR (500 MHz, CDCl$_3$): δ 7.62-7.60 (m, 4H), 7.34 (d, 2H, J=7.5 Hz), 3.84 (s, 6H), 2.65 (s, 6H) ppm. LC-MS (ESI): m/z 299.1 [M+H]$^+$.

Step 4. General Procedure H. Preparation of 4-5. To a solution of 4-4 (8.8 g, 29.5 mmol) in dichloromethane (250 mL) was slowly added 4 N BBr$_3$/DCM (44.3 mL) at 0° C. After stirring at rt for 30 min, the reaction was quenched by adding ice-cooled water (250 mL). The organic layer was separated and dried over MgSO$_4$. The solvent was removed and the residue was purified by silica gel column chromatography (PE/EA=1:1 (v/v)) to give 4-5 (7.0 g, 88% yield). LC-MS (ESI): m/z 271.1 [M+H]$^+$.

Step 5. General Procedure I. Preparation of 4-6. To a solution of 4-5 (0.80 g, 3.0 mmol) in DMF (60 mL) was added K$_2$CO$_3$ (1.1 g, 7.8 mmol). After stirring at 90° C. for 30 min, a solution of 2,2'-(ethane-1,2-diylbis(oxy))bis(ethane-2,1-diyl) bis(4-methylbenzenefulfonate) (1.6 g, 3.6 mmol) in 60 mL DMF was added slowly and the resulting mixture was stirred at 90° C. overnight. Subsequently, the reaction mixture was cooled to rt, poured into water (400 mL), and extracted with EtOAc (200 mL×3). The organic extracts were combined and washed with brine (200 mL) and dried over anhydrous Na$_2$SO$_4$. The solvent was removed and the residue was purified by silica gel column chromatography (PE/EtOAc=4:1 (v/v) to give 4-6 (450 mg, 40% yield). LC-MS (ESI): m/z 385.2 [M+H]$^+$.

Step 6. General Procedure J. Preparation of 4-7. To a solution of 4-6 (350 mg, 0.91 mmol) in DCM (10 mL) was added i-Pr$_2$NEt (470 mg, 3.64 mmol). The mixture was cooled to 0° C., TMSOTf (610 mg, 2.73 mmol) was dropwisely added to the reaction mixture. The resulting mixture was stirred at 0° C. for 30 min and then concentrated. The residue was diluted with hexane (200 mL), washed with brine, and dried with anhydrous Na$_2$SO$_4$. The solvent was removed and the residue was dried in vacuo to give crude 4-7 (481 mg) as a yellow solid, which was used for the next step without further purification. LC-MS (ESI): m/z 529.2 [M+H]$^+$.

Step 7. General Procedure K. Preparation of 4-8. To a solution of 4-7 (481 mg) in THF (12 mL) was added NBS (308 mg, 1.73 mmol) at 0° C. After stirring at 0° C. for 1 h, the reaction mixture was poured into water (60 mL) and extracted with DCM (50 mL×3). The organic layer was washed with brine (60 mL) and dried with anhydrous Na$_2$SO$_4$. The solvent was removed and the residue was dried in vacuo to give crude 4-8 (493 mg) as yellow oil, which was used for the next step without further purification. LC-MS (ESI): m/z 541.0 [M+H]$^+$.

Step 8. Preparation of 4-9. Following general procedures C and D and replacing compound 1-7 with 4-8, compound 4-9 was obtained as a yellow solid. $^1$H NMR (CD$_3$OD) δ 8.05 (d, 4H, J=12.5 Hz), 7.28 (d, 2H, J=9.0 Hz), 7.10 (d, 2H, J=10.0 Hz), 4.40-4.30 (m, 2H), 3.97 (d, 2H, J=9.0 Hz), 3.79 (brs, 4H), 3.76-3.48 (m, 10H), 2.18-2.16 (m, 2H), 2.06 (brs, 4H), 1.96-1.94 (m, 2H), 1.48 (s, 5H), 1.3 (s, 12H) ppm. LC-MS (ESI): m/z 771.4 [M+H]$^+$.

Step 9. Preparation of 4-10. Following general procedure G and replacing compound 1-11 with 4-9, compound 4-10 was obtained. LC-MS (ESI): m/z 885.4 [M+H]$^+$.

Example 11

Synthesis of 5-9 as shown in Scheme 5

Step 1. Preparation of 5-2. Following general procedure F and replacing compound 1-9 with 5-1 and 1-10 with 4-3, compound 5-2 was obtained in 53% yield. LC-MS (ESI): m/z 285.1 [M+H]$^+$.

Step 2. Preparation of 5-3. Following general procedure H and replacing compound 4-4 with 5-2, compound 5-3 was obtained in 42% yield. LC-MS (ESI): m/z 271.1 [M+H]$^+$.

Step 3. Preparation of 5-4. Following general procedure I and replacing compound 4-5 with 5-3 and 2,2'-(ethane-1,2-diylbis(oxy))bis(ethane-2,1-diyl)bis(4-methyl-benzenefulfonate) with 3,6,9,12-tetraoxatetradecane-1,14-diylbis(4-methylbenzenefulfonate), compound 5-4 was obtained in 22% yield. LC-MS (ESI): m/z 473.2 [M+H]$^+$.

Step 4. Preparation of 5-9. Following the sequence as shown in Scheme 4 for the synthesis of 4-10 from 4-5 and replacing 4-5 with 5-4, 5-9 was obtained. LC-MS (ESI): m/z 973.5 [M+H]$^+$.

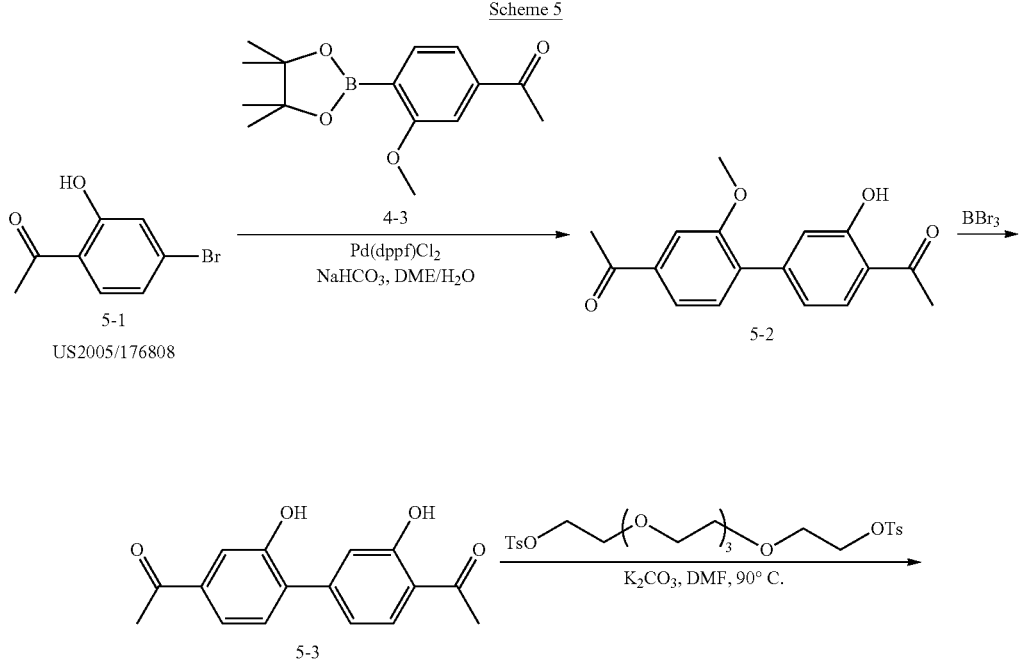

Scheme 5

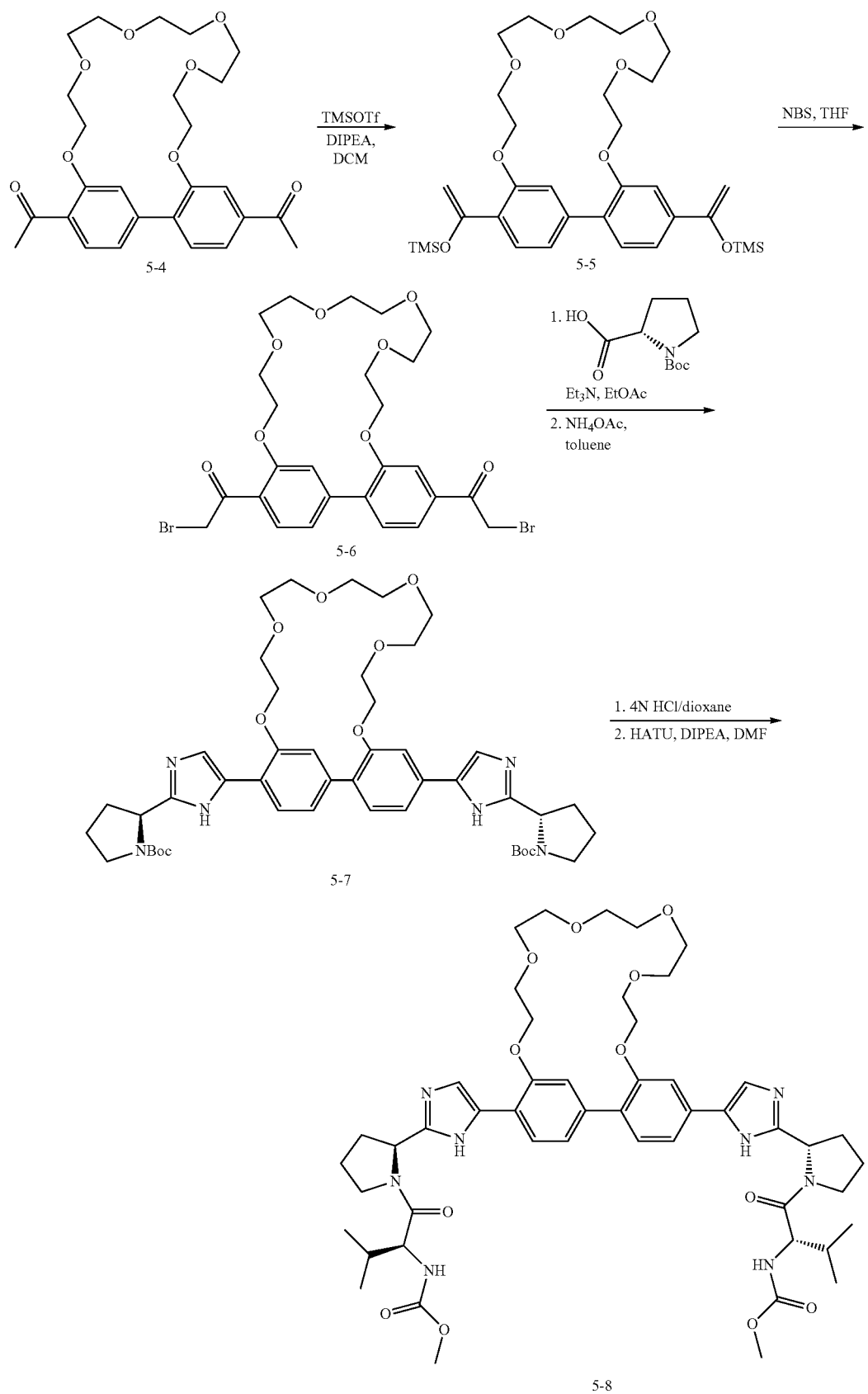

Scheme 6
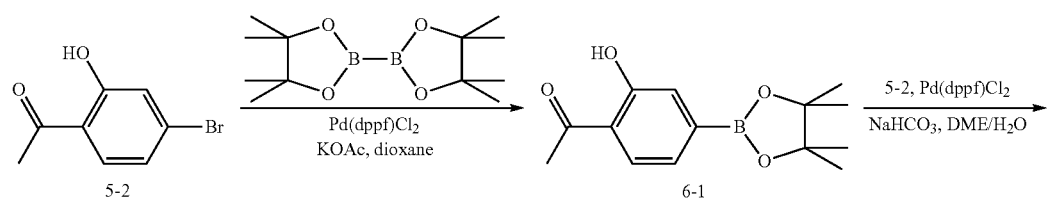
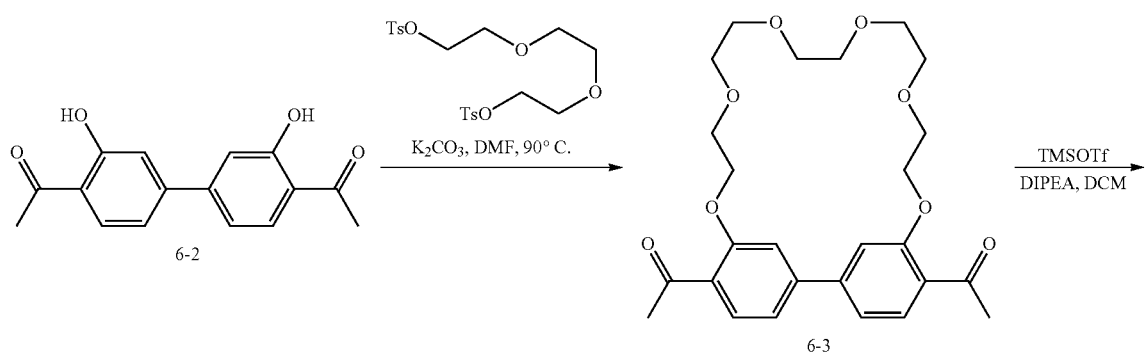
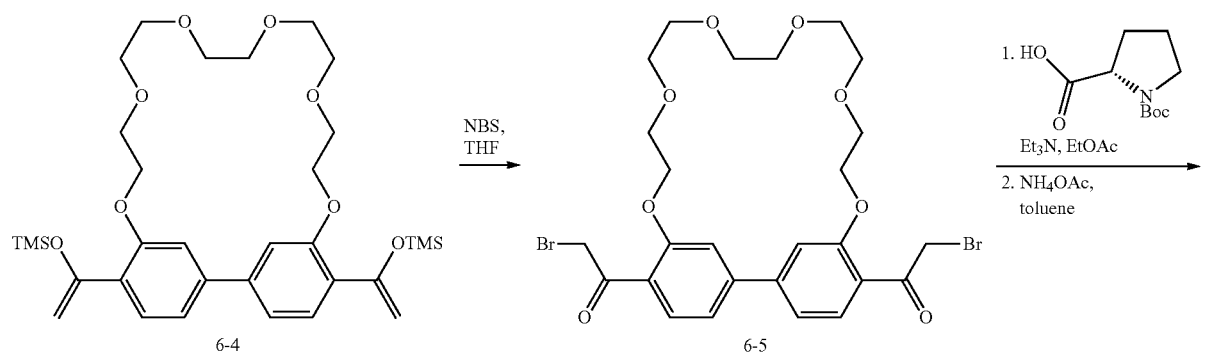
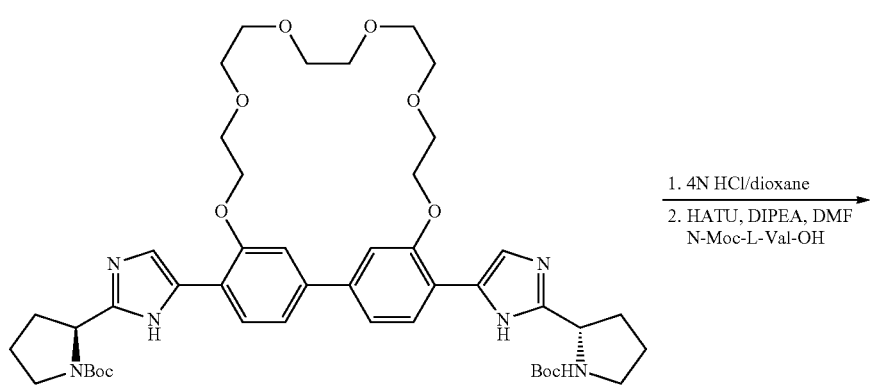

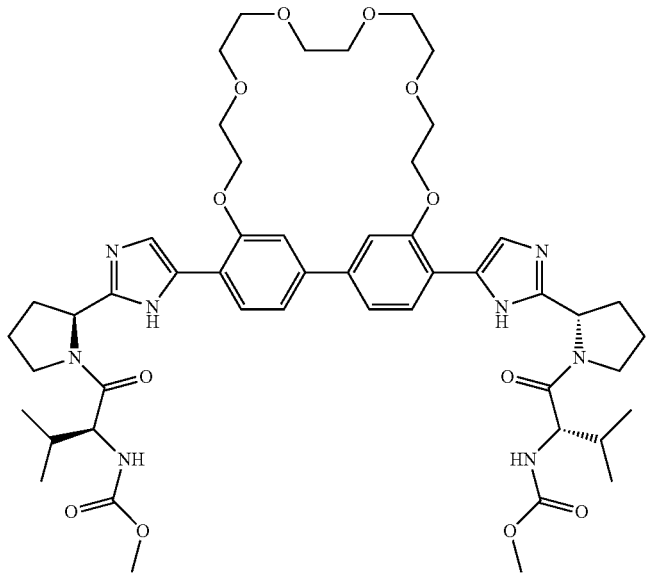

6-7

Example 12

Synthesis of 6-7 as shown in Scheme 6

Step 1. Preparation of 6-1. Following general procedure E and replacing 1-9 with 5-2, 6-1 was obtained in 82% yield. LC-MS (ESI): m/z 263.1 [M+H]$^+$.

Step 2. Preparation of 6-2. Following general procedure F and replacing 1-9 with 5-2 and 1-10 with 6-1, 6-2 was obtained in 48% yield. $^1$H NMR (400 MHz, CDCl$_3$): δ 12.34 (s, 2H), 7.82 (d, 2H, J=8.0 Hz), 7.23 (d, 2H, J=8.0 Hz), 7.15 (dd, 2H, J=8.0 Hz, 2.0 Hz), 2.68 (s, 6H) ppm. LC-MS (ESI): m/z 271.1 [M+H]$^+$.

Step 3. Preparation of 6-7. Following the sequence as shown in Scheme 4 for the synthesis of 4-10 from 4-5 and replacing 4-5 with 6-2, 6-7 was obtained. LC-MS (ESI): m/z 973.5 [M+H]$^+$.

Biological Activity

Biological activity of the compounds of the invention was determined using an HCV replicon assay. The HCV 1b_Huh-Luc/Neo-ET cell line persistently expressing a bicistronic genotype 1b replicon in Huh 7 cells was obtained from ReB-Likon GMBH. This cell line was used to test compound inhibition using luciferase enzyme activity readout as a measurement of compound inhibition of replicon levels.

On Day 1 (the day after plating cells), each compound is added in triplicate to the cells. Plates are incubated for 72 h prior to determining luciferase levels. Enzyme activity was measured using a Bright-Glo Kit (cat. number E2620) manufactured by Promega Corporation. The following equation was used to generate a percent control value for each compound.

$$\% \text{ Control} = (\text{Compound Luciferase Level/Control Luciferase Level})*100$$

The EC$_{50}$ value was determined using GraphPad Prism and the following equation:

$$Y = \text{Bottom asymptote} + (\text{Top asymptote} - \text{Bottom asymptote})/(1+10^{\wedge}((\text{LogEC50}-X)*\text{HillSlope}))$$

EC$_{50}$ values of compounds are determined several times in the replicon assay to generate average EC$_{50}$ values.

Example compounds of the disclosed invention are illustrated in Table 1. The table shows inhibitory activity of many of the example compounds with respect to HCV 1b. The biological activity is indicated as being *, , * or ****, which corresponds to EC$_{50}$ ranges of >1000 nM, 999 nM to 10 nM, 9.9 nM to 1 nM, or <1 nM respectively. The tables further provide mass spectrometry results for the synthesized example compounds.

TABLE 1

| Compound # | Structure | Inhibition of HCB genotype 1b | MS (M + H)+ |
|---|---|---|---|
| 1 | 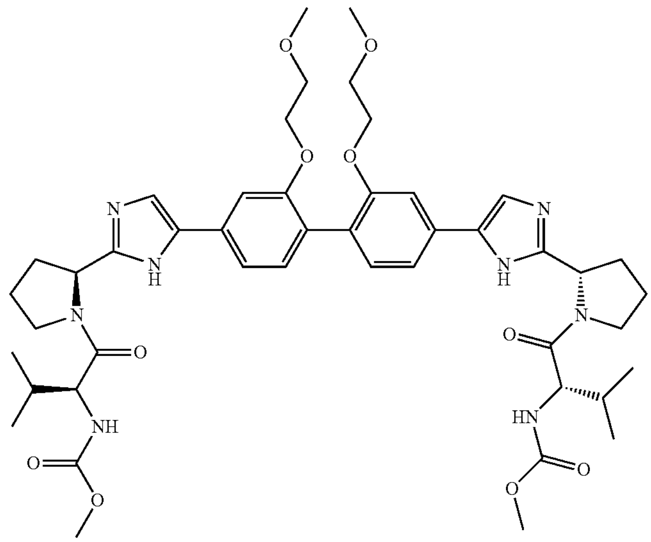 [SMILES: COCCOc1cc(-c2cnc([C@@H]3CCCN3C(=O)[C@@H](NC(=O)OC)C(C)C)[nH]2)ccc1-c1ccc(-c2cnc([C@@H]3CCCN3C(=O)[C@@H](NC(=O)OC)C(C)C)[nH]2)cc1OCCOC] | **** | 887.5 |
| 2 | 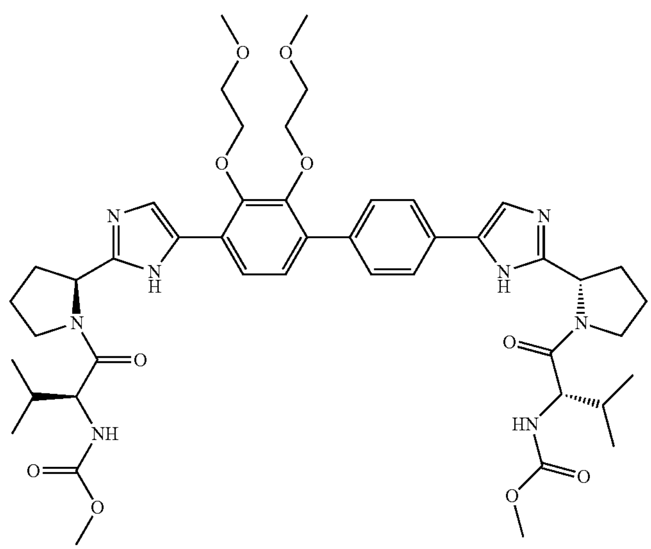 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@@H](NC(=O)OC)C(C)C)[nH]2)c1OCCOC] | **** | 887.5 |

TABLE 1-continued
| Compound # | Structure | Inhibition of HCB genotype 1b | MS (M + H)+ |
|---|---|---|---|
| 3 | 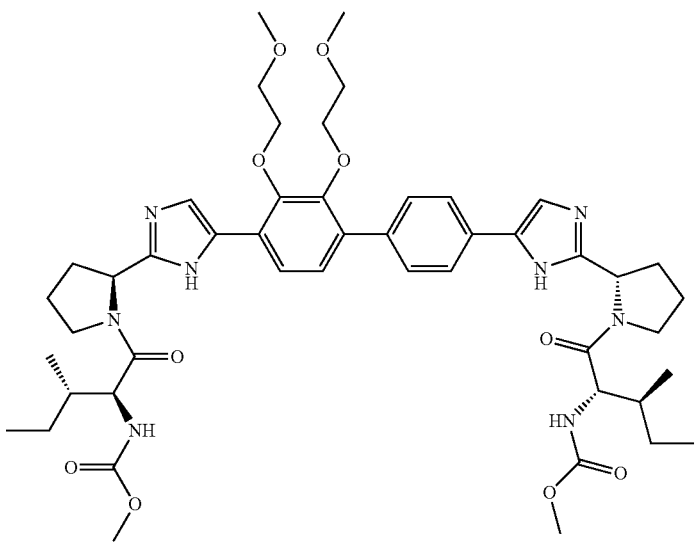 [SMILES: CC[C@H](C)[C@H](NC(=O)OC)C(=O)N1CCC[C@H]1c1ncc(-c2ccc(-c3ccc(-c4cnc([C@@H]5CCCN5C(=O)[C@@H](NC(=O)OC)[C@@H](C)CC)[nH]4)c(OCCOC)c3OCCOC)cc2)[nH]1] | **** | 915.5 |
| 4 | 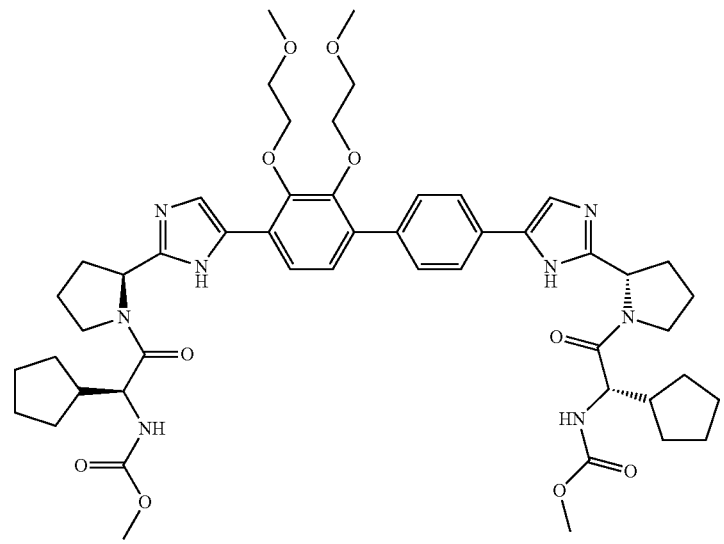 [SMILES: COCCOc1c(-c2ccc(-c3cnc([C@@H]4CCCN4C(=O)[C@@H](NC(=O)OC)C4CCCC4)[nH]3)cc2)ccc(-c2cnc([C@@H]3CCCN3C(=O)[C@@H](NC(=O)OC)C3CCCC3)[nH]2)c1OCCOC] | **** | 939.5 |

TABLE 1-continued

| Compound # | Structure | Inhibition of HCB genotype 1b | MS (M + H)+ |
|---|---|---|---|
| 5 | 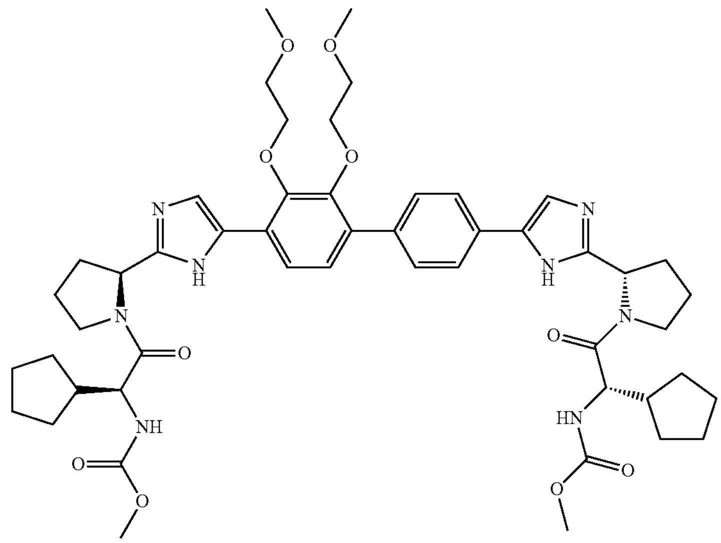 [SMILES: COCCOc1c(-c2ccc(-c3cnc([C@@H]4CCCN4C(=O)[C@@H](NC(=O)OC)C4CCCC4)[nH]3)cc2)ccc(-c2cnc([C@@H]3CCCN3C(=O)[C@@H](NC(=O)OC)C3CCCC3)[nH]2)c1OCCOC] | **** | 967.5 |
| 6 | 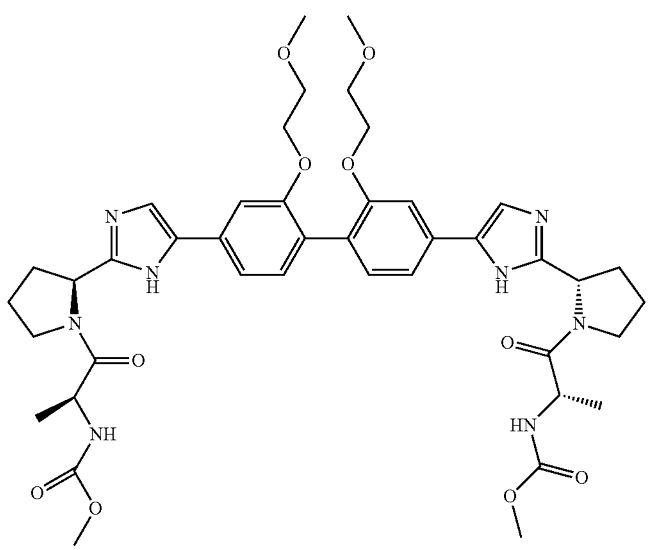 [SMILES: COCCOc1cc(-c2cnc([C@@H]3CCCN3C(=O)[C@H](C)NC(=O)OC)[nH]2)ccc1-c1ccc(-c2cnc([C@@H]3CCCN3C(=O)[C@H](C)NC(=O)OC)[nH]2)cc1OCCOC] | ** | 831.4 |

TABLE 1-continued

| Compound # | Structure | Inhibition of HCB genotype 1b | MS (M + H)+ |
|---|---|---|---|
| 7 | 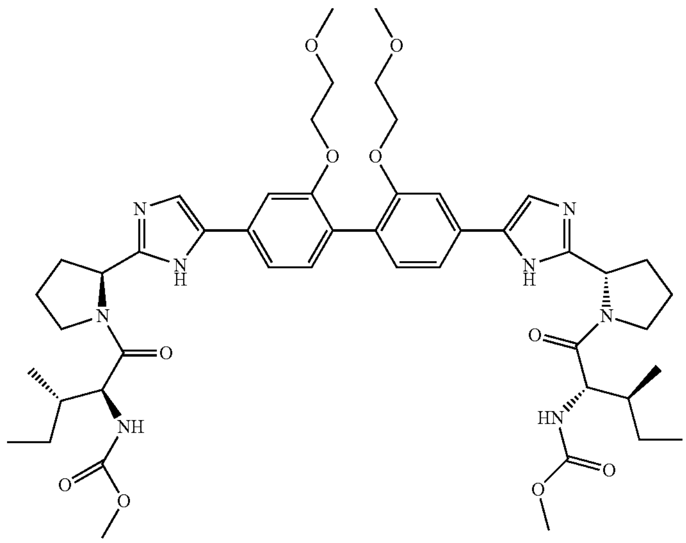 [SMILES: CC[C@H](C)[C@H](NC(=O)OC)C(=O)N1CCC[C@H]1c1ncc(-c2ccc(-c3ccc(-c4cnc([C@@H]5CCCN5C(=O)[C@@H](NC(=O)OC)[C@@H](C)CC)[nH]4)cc3OCCOC)c(OCCOC)c2)[nH]1] | **** | 915.5 |
| 8 | 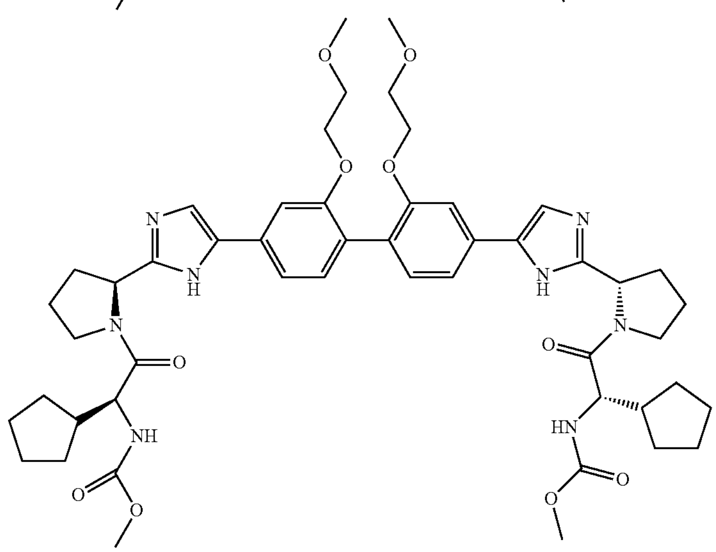 | **** | 939.5 |
| 9 | 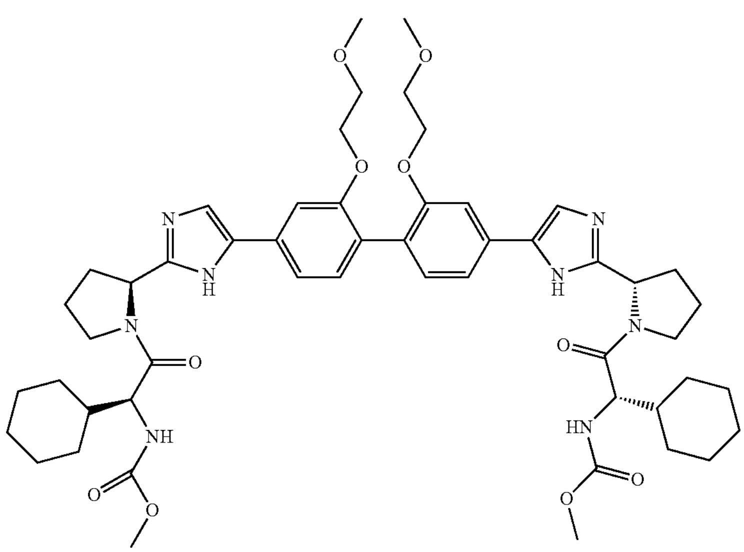 [SMILES: COCCOc1cc(-c2cnc([C@@H]3CCCN3C(=O)[C@@H](NC(=O)OC)C3CCCCC3)[nH]2)ccc1-c1ccc(-c2cnc([C@@H]3CCCN3C(=O)[C@@H](NC(=O)OC)C3CCCCC3)[nH]2)cc1OCCOC] | **** | 967.5 |

TABLE 1-continued
| Compound # | Structure | Inhibition of HCB genotype 1b | MS (M + H)+ |
|---|---|---|---|
| 10 | 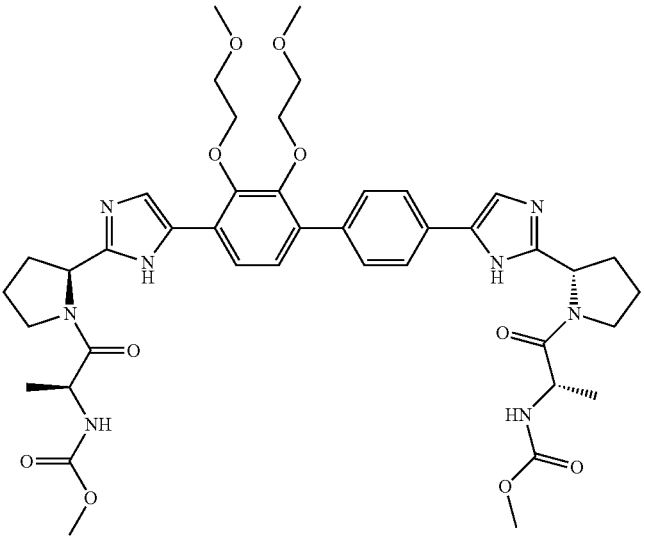 [SMILES: COCCOc1c(-c2ccc(-c3cnc([C@@H]4CCCN4C(=O)[C@H](C)NC(=O)OC)[nH]3)cc2)ccc(-c2cnc([C@@H]3CCCN3C(=O)[C@H](C)NC(=O)OC)[nH]2)c1OCCOC] | **** | 831.4 |
| 11 | 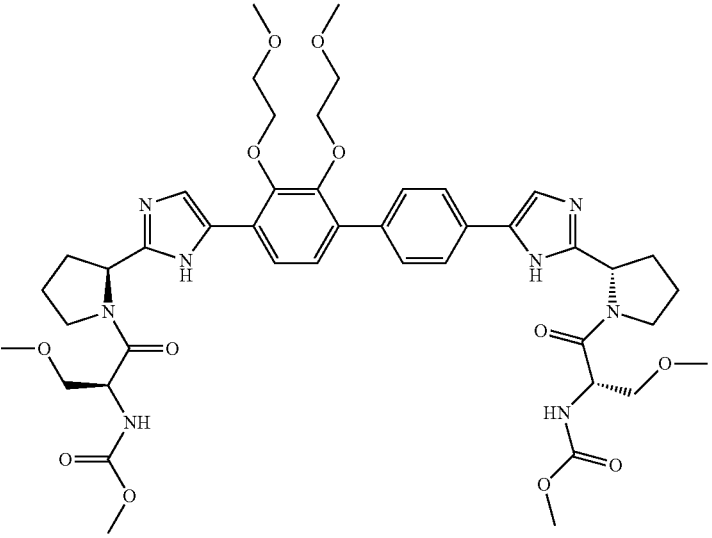 | ** | 891.4 |

TABLE 1-continued
| Compound # | Structure | Inhibition of HCB genotype 1b | MS (M + H)+ |
|---|---|---|---|
| 12 | 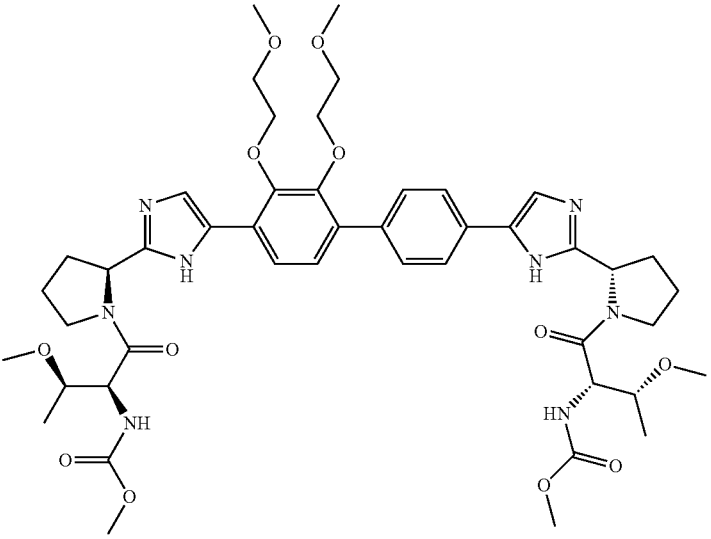 | *** | 919.4 |
| 13 | 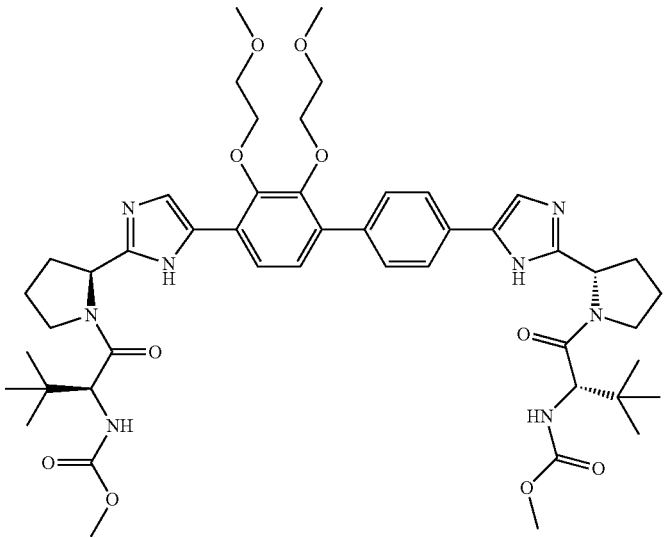 [SMILES: COCCOc1c(-c2ccc(-c3cnc([C@@H]4CCCN4C(=O)[C@@H](NC(=O)OC)C(C)(C)C)[nH]3)cc2)ccc(-c2cnc([C@@H]3CCCN3C(=O)[C@@H](NC(=O)OC)C(C)(C)C)[nH]2)c1OCCOC] | *** | 915.4 |

TABLE 1-continued

| Compound # | Structure | Inhibition of HCB genotype 1b | MS (M + H)+ |
|---|---|---|---|
| 14 | 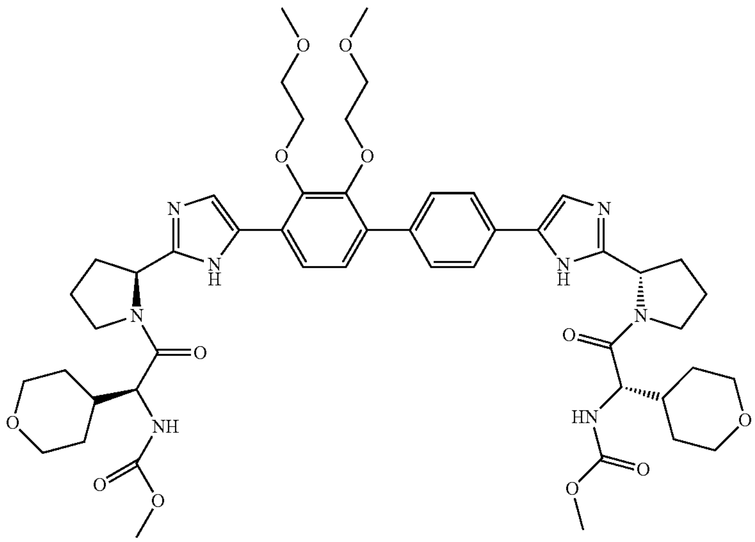 [SMILES: COCCOc1c(-c2ccc(-c3cnc([C@@H]4CCCN4C(=O)[C@@H](NC(=O)OC)C4CCOCC4)[nH]3)cc2)ccc(-c2cnc([C@@H]3CCCN3C(=O)[C@@H](NC(=O)OC)C3CCOCC3)[nH]2)c1OCCOC] | *** | 971.5 |
| 15 | 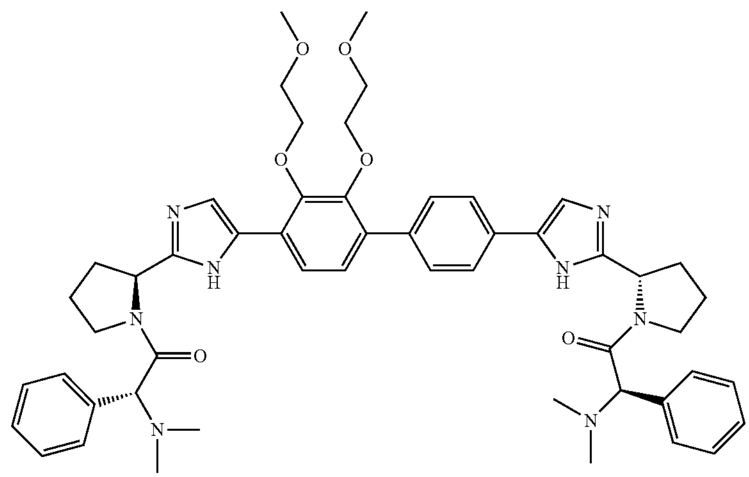 [SMILES: COCCOc1c(-c2ccc(-c3cnc([C@@H]4CCCN4C(=O)[C@@H](c4ccccc4)N(C)C)[nH]3)cc2)ccc(-c2cnc([C@@H]3CCCN3C(=O)[C@@H](c3ccccc3)N(C)C)[nH]2)c1OCCOC] | **** | 895.5 |
| 16 | 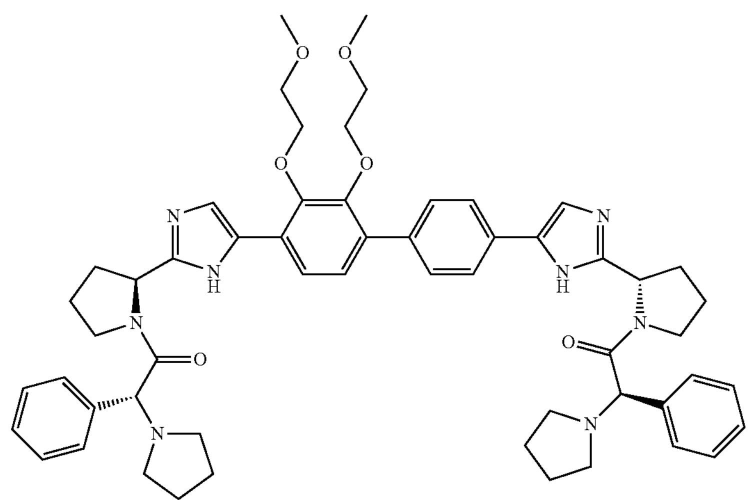 [SMILES: COCCOc1c(-c2ccc(-c3cnc([C@@H]4CCCN4C(=O)[C@@H](c4ccccc4)N4CCCC4)[nH]3)cc2)ccc(-c2cnc([C@@H]3CCCN3C(=O)[C@@H](c3ccccc3)N3CCCC3)[nH]2)c1OCCOC] | *** | 947.5 |

TABLE 1-continued
| Compound # | Structure | Inhibition of HCB genotype 1b | MS (M + H)+ |
|---|---|---|---|
| 17 | 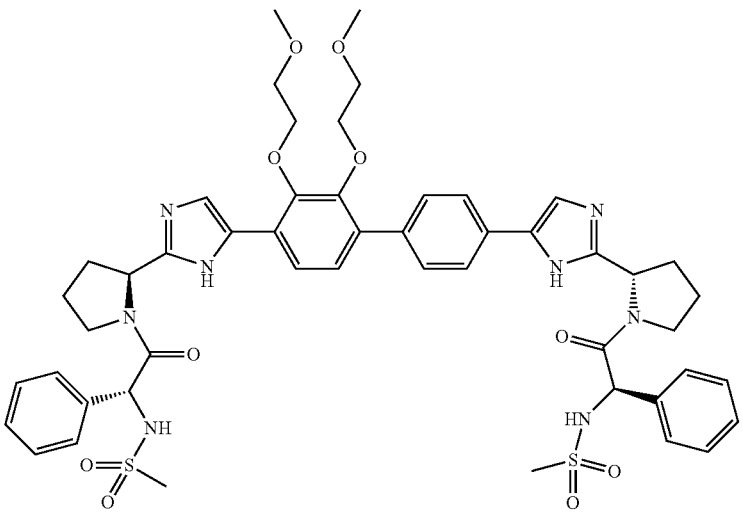 [SMILES: COCCOc1c(-c2ccc(-c3cnc([C@@H]4CCCN4C(=O)[C@H](NS(C)(=O)=O)c4ccccc4)[nH]3)cc2)ccc(-c2cnc([C@@H]3CCCN3C(=O)[C@H](NS(C)(=O)=O)c3ccccc3)[nH]2)c1OCCOC] | **** | 995.4 |
| 18 | 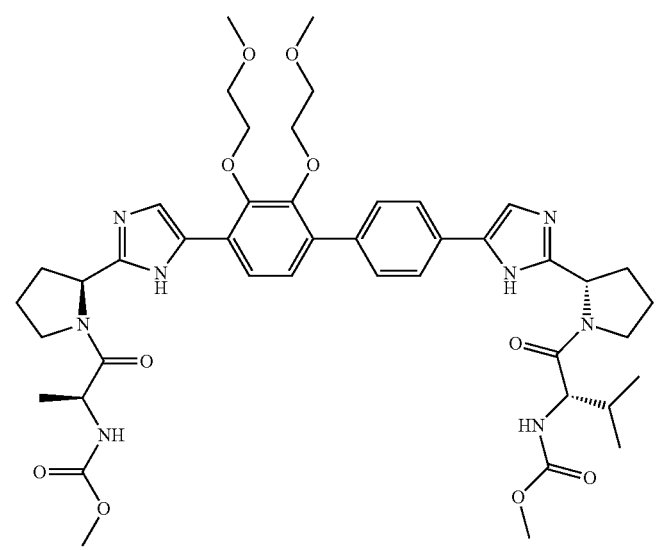 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@H](C)NC(=O)OC)[nH]2)c1OCCOC] | *** | 859.4 |
| 19 | 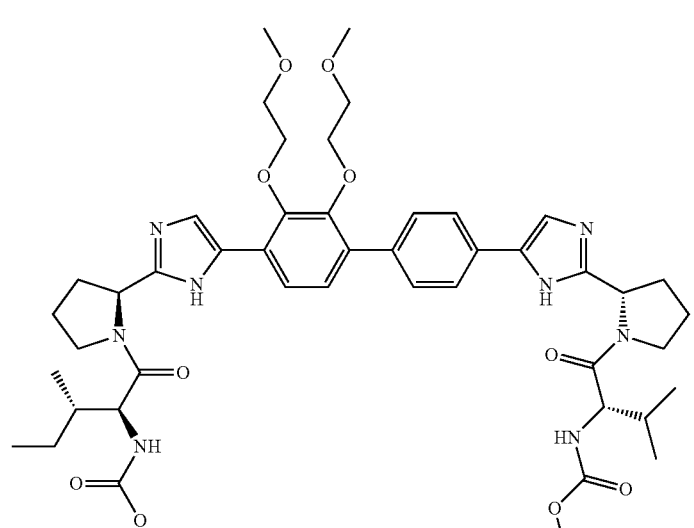 | **** | 901.5 |

TABLE 1-continued

| Compound # | Structure | Inhibition of HCB genotype 1b | MS (M + H)+ |
|---|---|---|---|
| 20 | 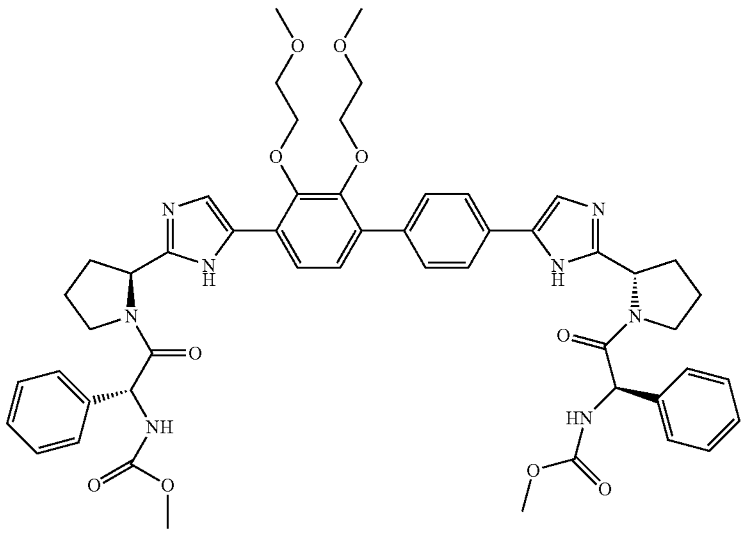 [SMILES: COCCOc1c(-c2ccc(-c3cnc([C@@H]4CCCN4C(=O)[C@H](NC(=O)OC)c4ccccc4)[nH]3)cc2)ccc(-c2cnc([C@@H]3CCCN3C(=O)[C@H](NC(=O)OC)c3ccccc3)[nH]2)c1OCCOC] | | 955.4 |
| 21 | 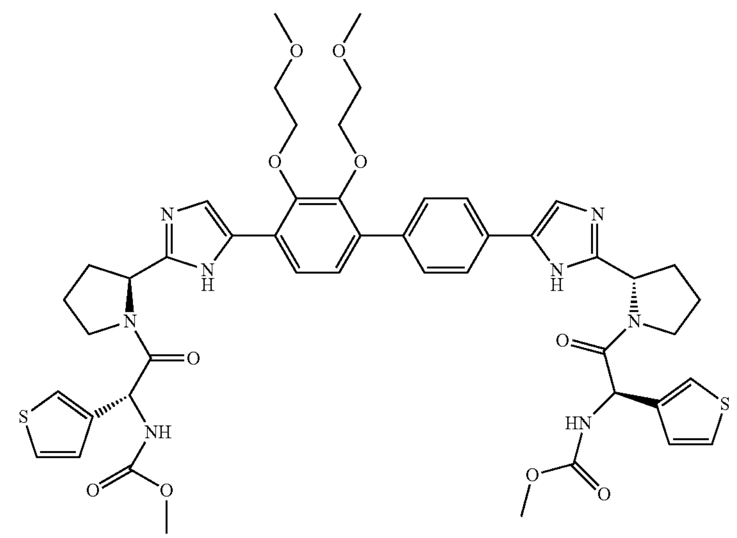 [SMILES: COCCOc1c(-c2ccc(-c3cnc([C@@H]4CCCN4C(=O)[C@H](NC(=O)OC)c4ccsc4)[nH]3)cc2)ccc(-c2cnc([C@@H]3CCCN3C(=O)[C@H](NC(=O)OC)c3ccsc3)[nH]2)c1OCCOC] | | 967.3 |
| 22 | 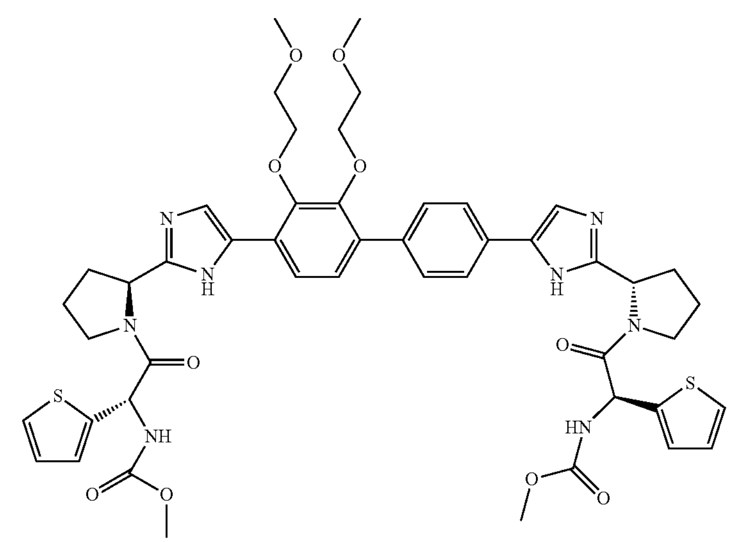 [SMILES: COCCOc1c(-c2ccc(-c3cnc([C@@H]4CCCN4C(=O)[C@H](NC(=O)OC)c4cccs4)[nH]3)cc2)ccc(-c2cnc([C@@H]3CCCN3C(=O)[C@H](NC(=O)OC)c3cccs3)[nH]2)c1OCCOC] | | 967.3 |

TABLE 1-continued

| Compound # | Structure | Inhibition of HCB genotype 1b | MS (M + H)+ |
|---|---|---|---|
| 23 | 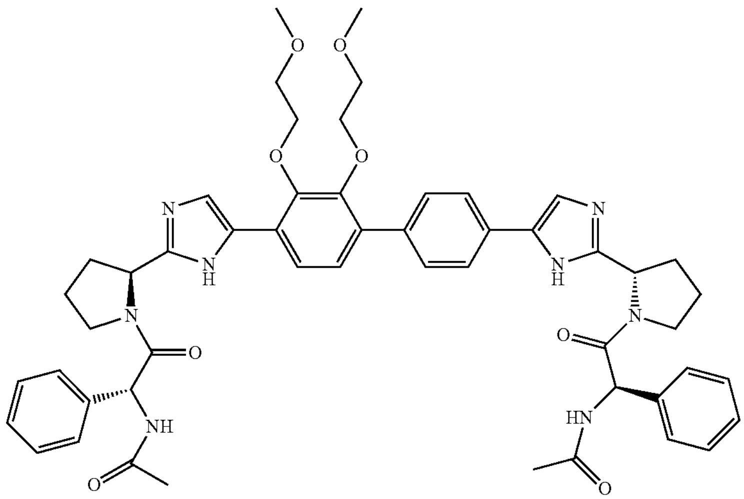 [SMILES: COCCOc1c(-c2ccc(-c3cnc([C@@H]4CCCN4C(=O)[C@H](NC(C)=O)c4ccccc4)[nH]3)cc2)ccc(-c2cnc([C@@H]3CCCN3C(=O)[C@H](NC(C)=O)c3ccccc3)[nH]2)c1OCCOC] | | 923.4 |
| 24 | 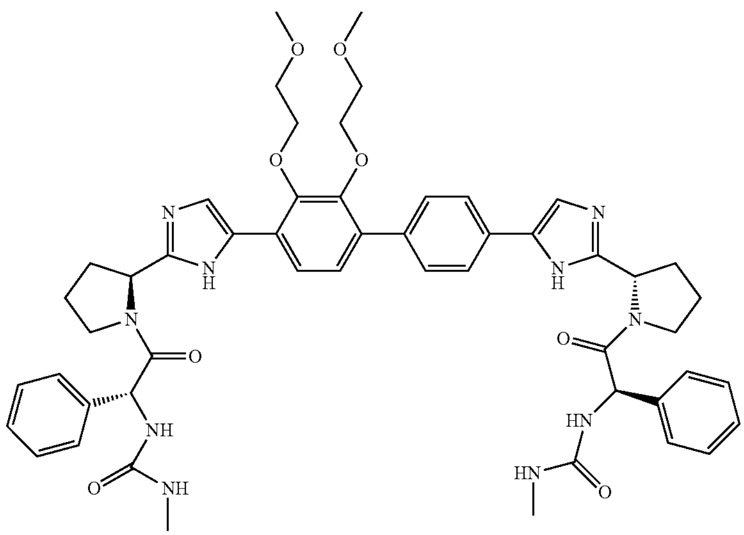 [SMILES: CNC(=O)N[C@@H](C(=O)N1CCC[C@H]1c1ncc(-c2ccc(-c3ccc(-c4cnc([C@@H]5CCCN5C(=O)[C@H](NC(=O)NC)c5ccccc5)[nH]4)c(OCCOC)c3OCCOC)cc2)[nH]1)c1ccccc1] | | 953.5 |
| 25 | 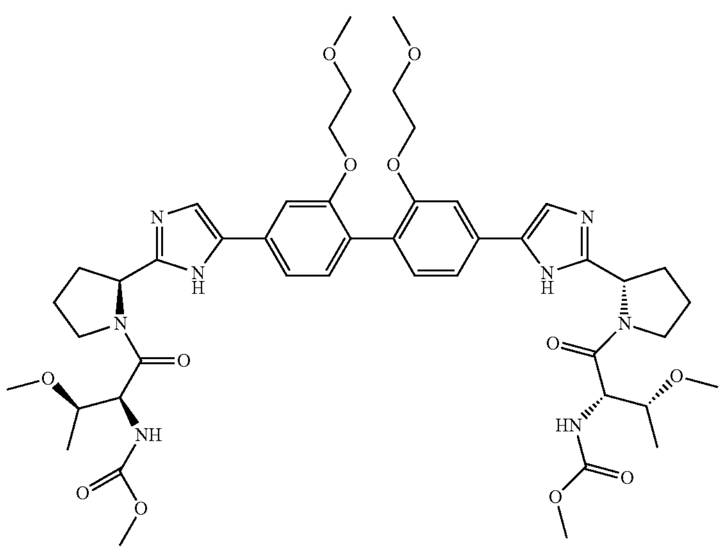 | | 919.4 |

TABLE 1-continued

| Compound # | Structure | Inhibition of HCB genotype 1b | MS (M + H)+ |
|---|---|---|---|
| 26 | 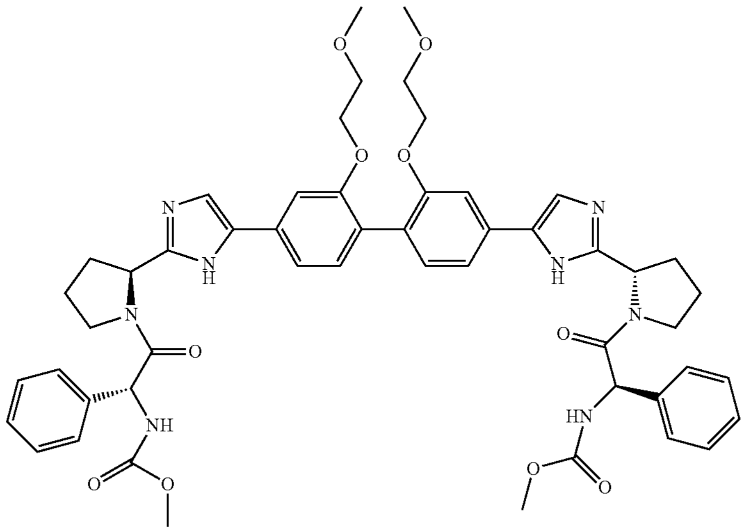 [SMILES: COCCOc1cc(-c2cnc([C@@H]3CCCN3C(=O)[C@H](NC(=O)OC)c3ccccc3)[nH]2)ccc1-c1ccc(-c2cnc([C@@H]3CCCN3C(=O)[C@H](NC(=O)OC)c3ccccc3)[nH]2)cc1OCCOC] | | 955.4 |
| 27 | 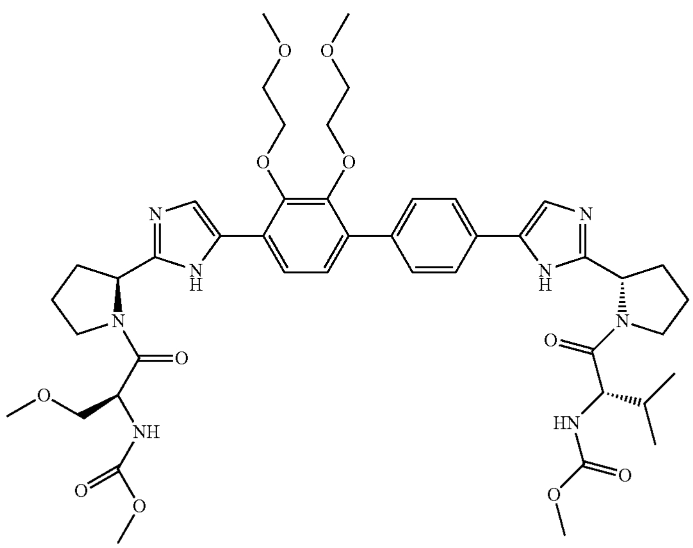 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@H](COC)NC(=O)OC)[nH]2)c1OCCOC] | | 889.4 |

TABLE 1-continued

| Compound # | Structure | Inhibition of HCB genotype 1b | MS (M + H)+ |
|---|---|---|---|
| 28 | 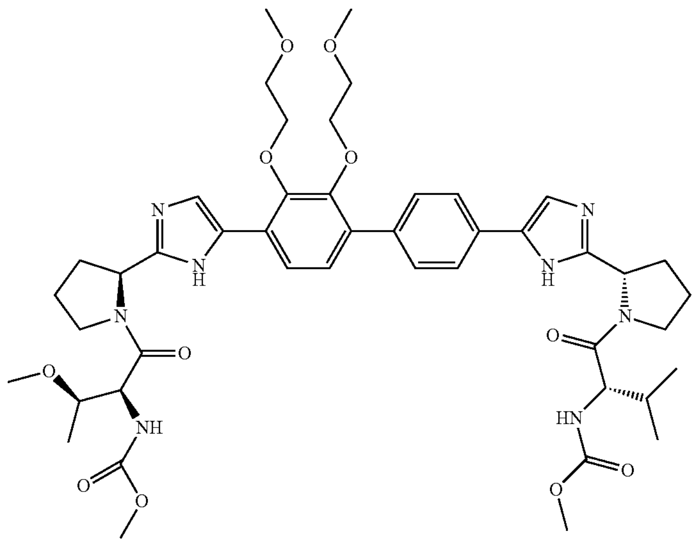 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@@H](NC(=O)OC)[C@@H](C)OC)[nH]2)c1OCCOC] | | 903.5 |
| 29 | 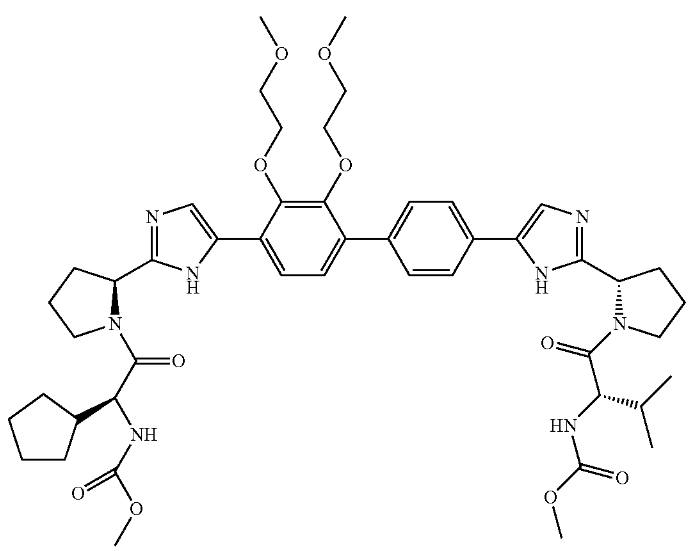 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@@H](NC(=O)OC)C3CCCC3)[nH]2)c1OCCOC] | | 913.5 |

TABLE 1-continued
| Compound # | Structure | Inhibition of HCB genotype 1b | MS (M + H)+ |
|---|---|---|---|
| 30 | 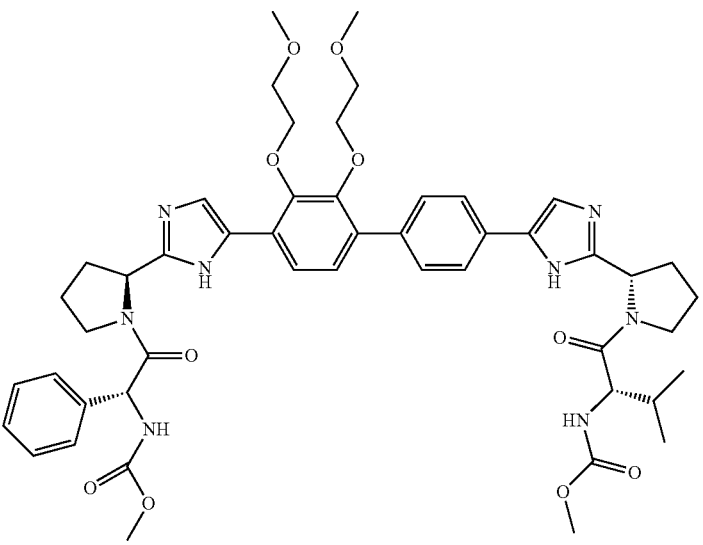 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@H](NC(=O)OC)c3ccccc3)[nH]2)c1OCCOC] | | 921.4 |
| 31 | 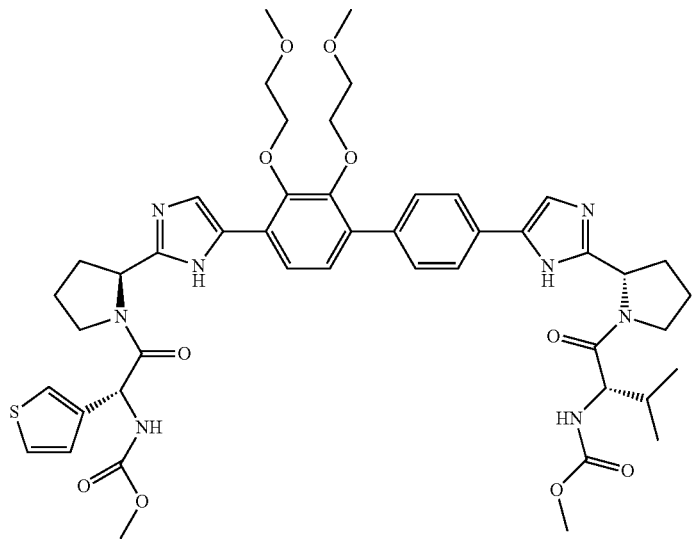 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@H](NC(=O)OC)c3ccsc3)[nH]2)c1OCCOC] | | 927.4 |

TABLE 1-continued
| Compound # | Structure | Inhibition of HCB genotype 1b | MS (M + H)+ |
|---|---|---|---|
| 32 | 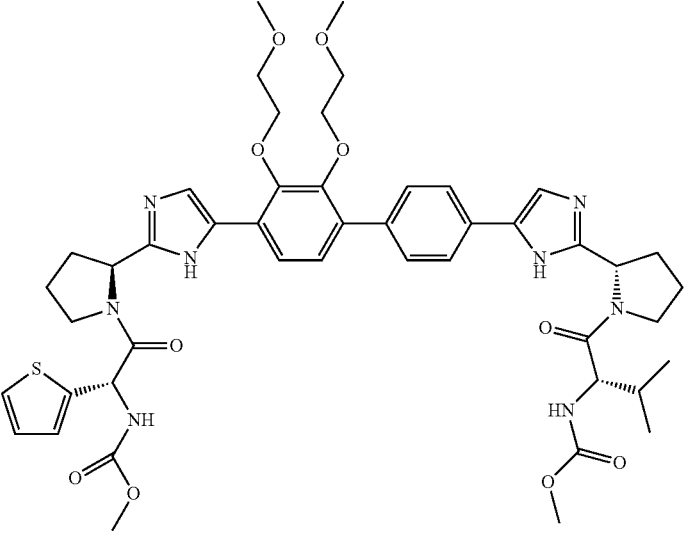 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@H](NC(=O)OC)c3cccs3)[nH]2)c1OCCOC] | | 927.4 |
| 33 | 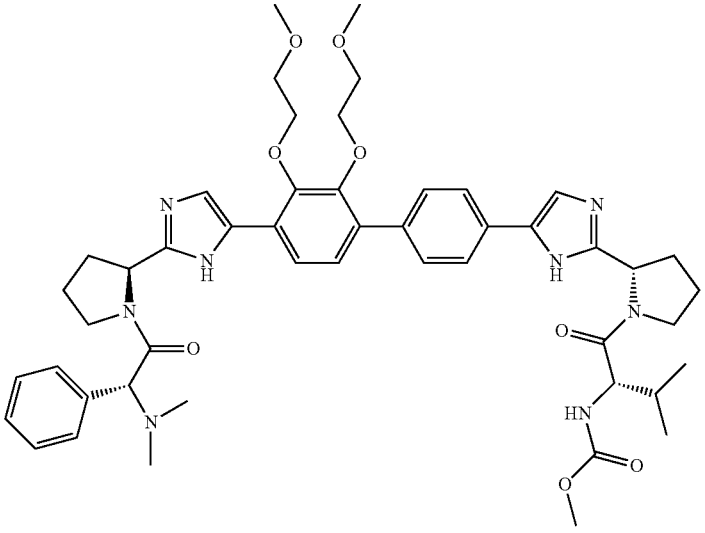 [SMILES: COCCOc1c(-c2ccc(-c3cnc([C@@H]4CCCN4C(=O)[C@@H](NC(=O)OC)C(C)C)[nH]3)cc2)ccc(-c2cnc([C@@H]3CCCN3C(=O)[C@@H](c3ccccc3)N(C)C)[nH]2)c1OCCOC] | | 891.5 |

TABLE 1-continued
| Compound # | Structure | Inhibition of HCB genotype 1b | MS (M + H)+ |
|---|---|---|---|
| 34 | 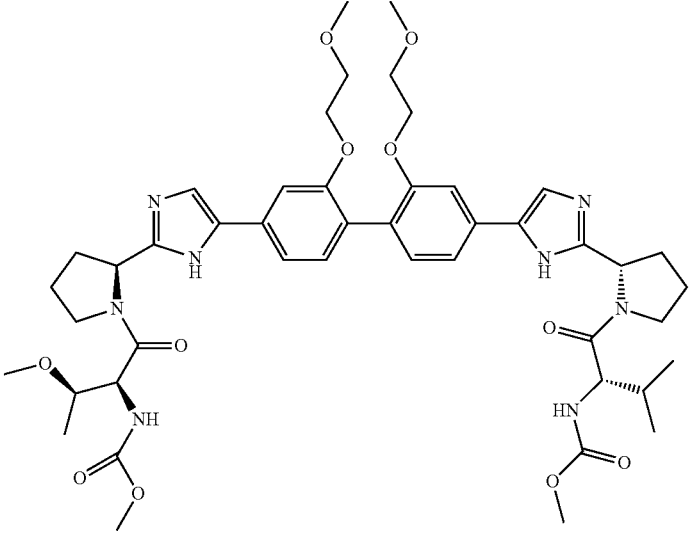 [SMILES: COCCOc1cc(-c2cnc([C@@H]3CCCN3C(=O)[C@@H](NC(=O)OC)C(C)C)[nH]2)ccc1-c1ccc(-c2cnc([C@@H]3CCCN3C(=O)[C@@H](NC(=O)OC)[C@@H](C)OC)[nH]2)cc1OCCOC] | | 903.5 |
| 35 | 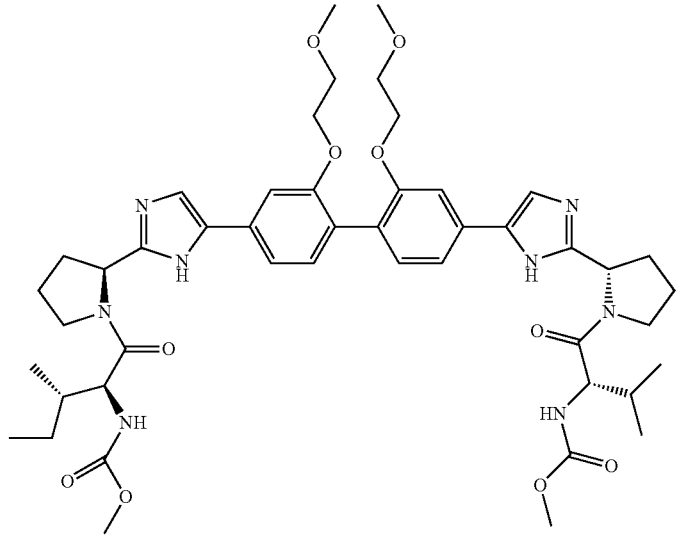 [SMILES: CC[C@H](C)[C@H](NC(=O)OC)C(=O)N1CCC[C@H]1c1ncc(-c2ccc(-c3ccc(-c4cnc([C@@H]5CCCN5C(=O)[C@@H](NC(=O)OC)C(C)C)[nH]4)cc3OCCOC)c(OCCOC)c2)[nH]1] | | 901.5 |

TABLE 1-continued

| Compound # | Structure | Inhibition of HCB genotype 1b | MS (M + H)+ |
|---|---|---|---|
| 36 | 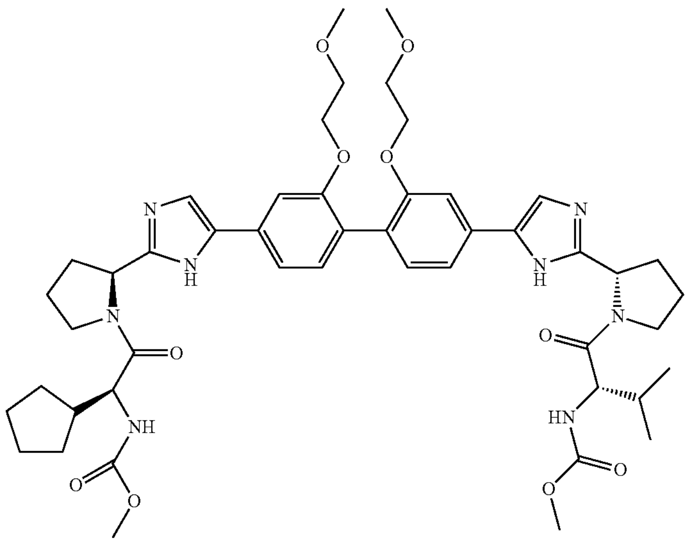 [SMILES: COCCOc1cc(-c2cnc([C@@H]3CCCN3C(=O)[C@@H](NC(=O)OC)C(C)C)[nH]2)ccc1-c1ccc(-c2cnc([C@@H]3CCCN3C(=O)[C@@H](NC(=O)OC)C3CCCC3)[nH]2)cc1OCCOC] | | 913.5 |
| 37 | 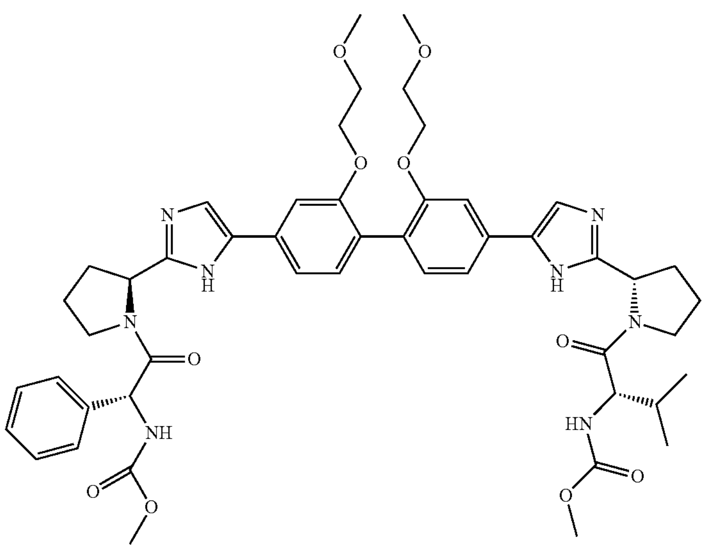 [SMILES: COCCOc1cc(-c2cnc([C@@H]3CCCN3C(=O)[C@@H](NC(=O)OC)C(C)C)[nH]2)ccc1-c1ccc(-c2cnc([C@@H]3CCCN3C(=O)[C@H](NC(=O)OC)c3ccccc3)[nH]2)cc1OCCOC] | | 921.4 |

TABLE 1-continued

| Compound # | Structure | Inhibition of HCB genotype 1b | MS (M + H)+ |
|---|---|---|---|
| 38 | 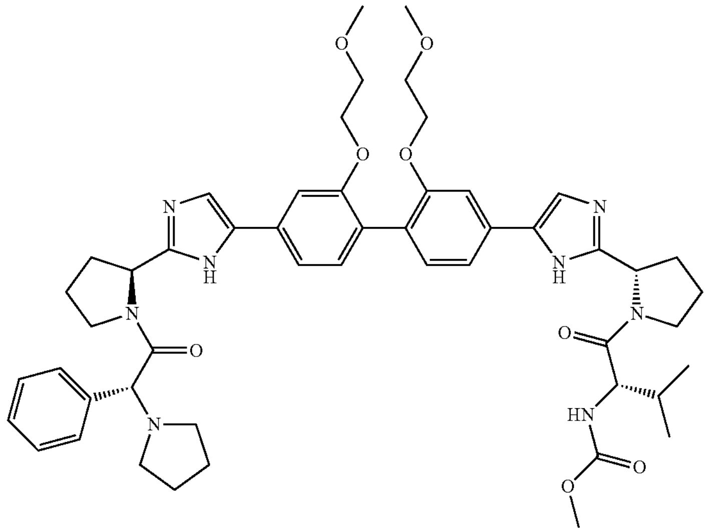 [SMILES: COCCOc1cc(-c2cnc([C@@H]3CCCN3C(=O)[C@@H](NC(=O)OC)C(C)C)[nH]2)ccc1-c1ccc(-c2cnc([C@@H]3CCCN3C(=O)[C@@H](c3ccccc3)N3CCCC3)[nH]2)cc1OCCOC] | | 917.5 |
| 39 | 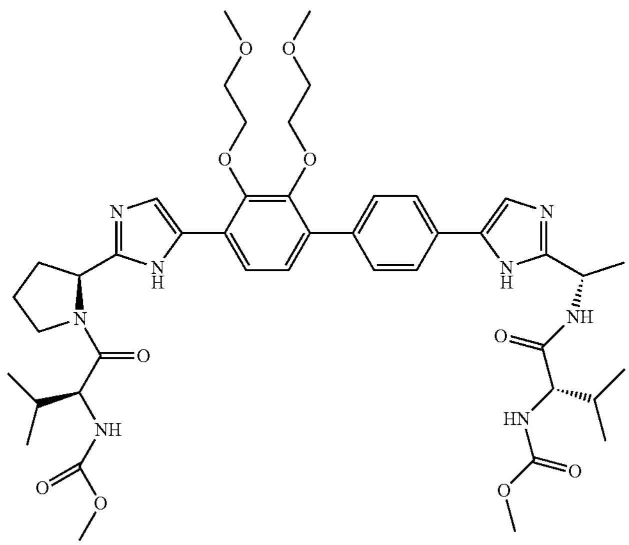 [SMILES: COCCOc1c(-c2ccc(-c3cnc([C@H](C)NC(=O)[C@@H](NC(=O)OC)C(C)C)[nH]3)cc2)ccc(-c2cnc([C@@H]3CCCN3C(=O)[C@@H](NC(=O)OC)C(C)C)[nH]2)c1OCCOC] | | 861.4 |
| 40 | 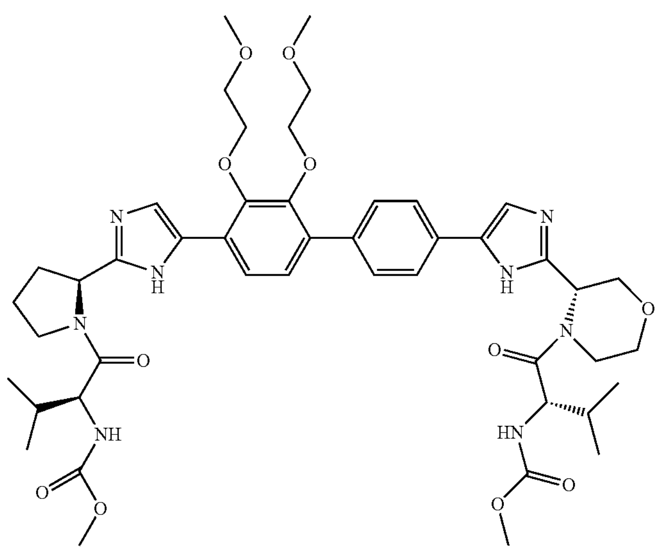 [SMILES: COCCOc1c(-c2ccc(-c3cnc([C@@H]4COCCN4C(=O)[C@@H](NC(=O)OC)C(C)C)[nH]3)cc2)ccc(-c2cnc([C@@H]3CCCN3C(=O)[C@@H](NC(=O)OC)C(C)C)[nH]2)c1OCCOC] | | 903.5 |

TABLE 1-continued

| Compound # | Structure | Inhibition of HCB genotype 1b | MS (M + H)+ |
|---|---|---|---|
| 41 | 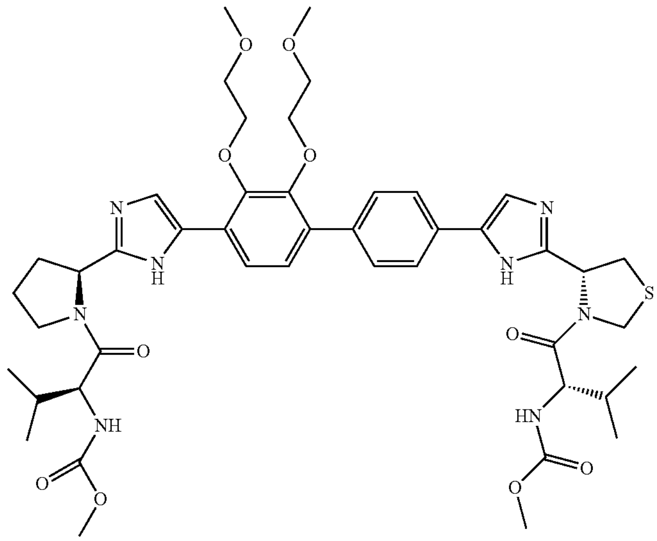 [SMILES: COCCOc1c(-c2ccc(-c3cnc([C@@H]4CSCN4C(=O)[C@@H](NC(=O)OC)C(C)C)[nH]3)cc2)ccc(-c2cnc([C@@H]3CCCN3C(=O)[C@@H](NC(=O)OC)C(C)C)[nH]2)c1OCCOC] | | 905.4 |
| 42 | 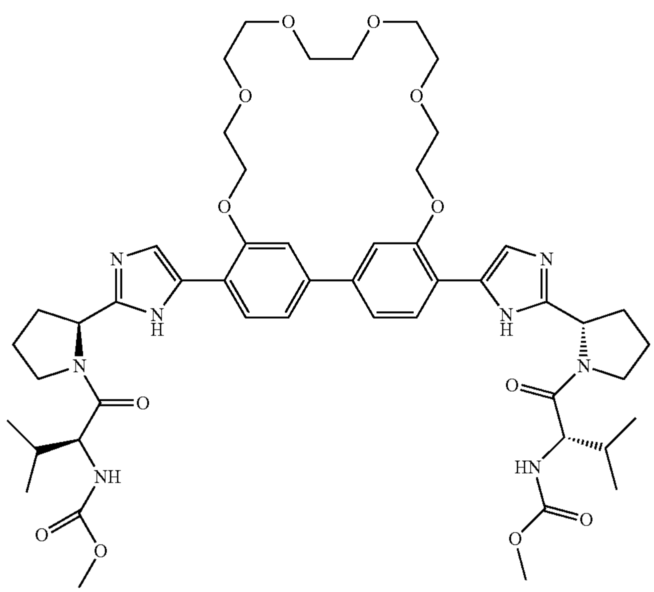 [SMILES: COC(=O)N[C@H](C(=O)N1CCC[C@H]1c1ncc(-c2ccc3cc2OCCOCCOCCOCCOCCOc2cc-3ccc2-c2cnc([C@@H]3CCCN3C(=O)[C@@H](NC(=O)OC)C(C)C)[nH]2)[nH]1)C(C)C] | | 973.5 |

TABLE 1-continued

| Compound # | Structure | Inhibition of HCB genotype 1b | MS (M + H)+ |
| --- | --- | --- | --- |
| 43 | 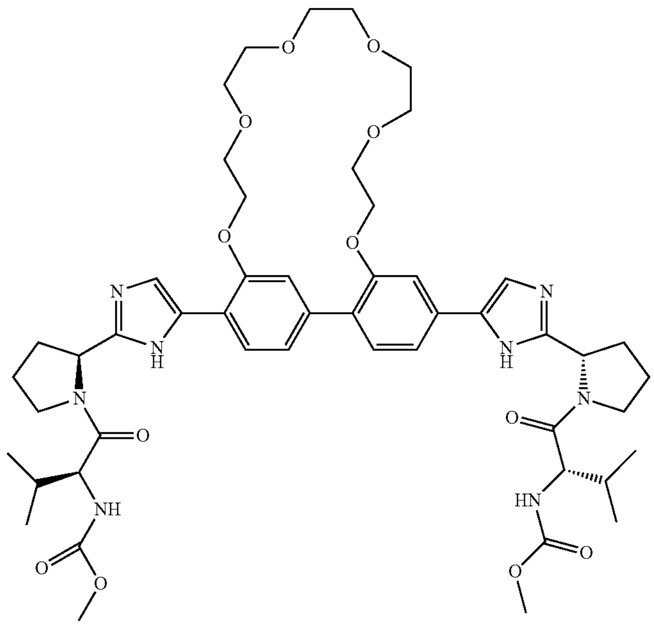 [SMILES: COC(=O)N[C@H](C(=O)N1CCC[C@H]1c1ncc(-c2ccc3c(c2)OCCOCCOCCOCCOCCOc2cc-3ccc2-c2cnc([C@@H]3CCCN3C(=O)[C@@H](NC(=O)OC)C(C)C)[nH]2)[nH]1)C(C)C] | | 973.5 |
| 44 | 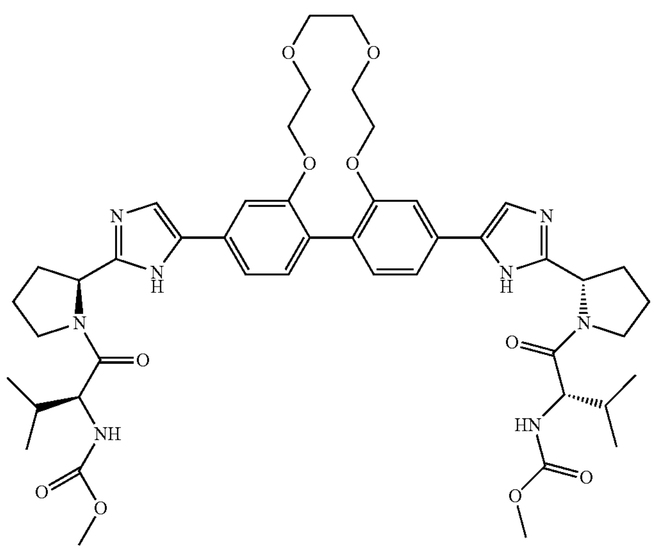 [SMILES: COC(=O)N[C@H](C(=O)N1CCC[C@H]1c1ncc(-c2ccc3c(c2)OCCOCCOCCOc2cc(-c4cnc([C@@H]5CCCN5C(=O)[C@@H](NC(=O)OC)C(C)C)[nH]4)ccc2-3)[nH]1)C(C)C] | | 885.4 |

TABLE 1-continued
| Compound # | Structure | Inhibition of HCB genotype 1b | MS (M + H)+ |
|---|---|---|---|
| 45 | 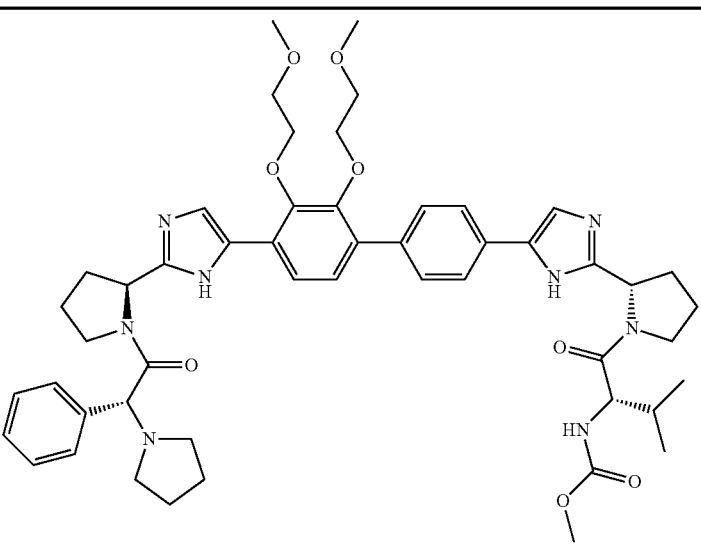 | | 917.5 |
Additional example compounds are provided in Table 2.
TABLE 2
| Compound # | Structure |
|---|---|
| 50 | 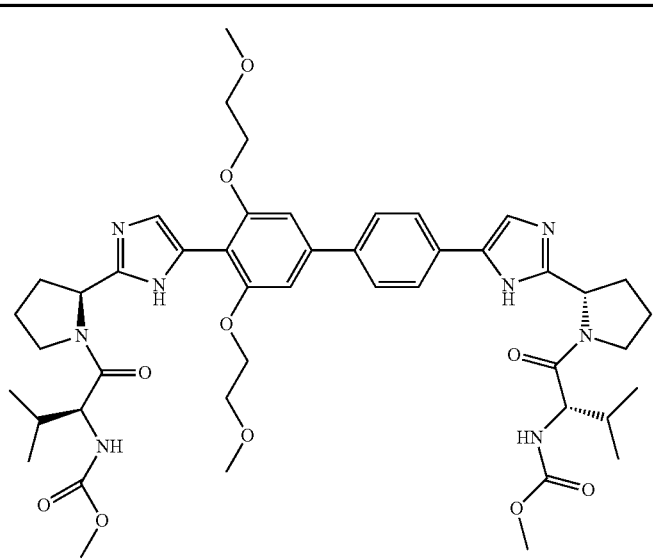 |

TABLE 2-continued

| Compound # | Structure |
|---|---|
| 51 | 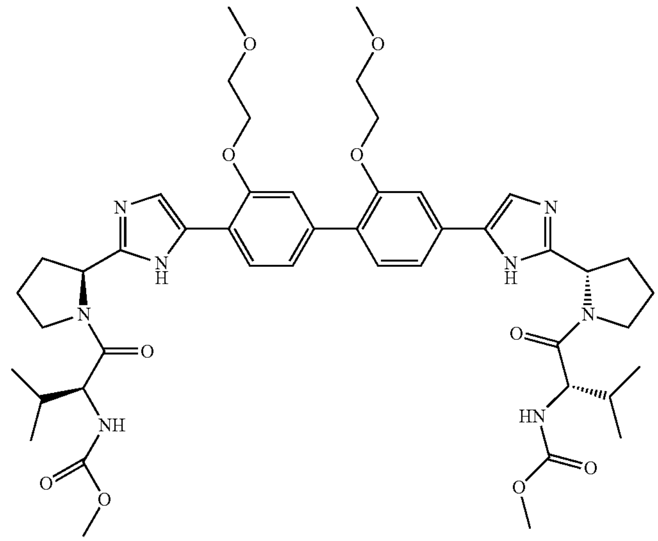 [SMILES: COCCOc1cc(-c2cnc([C@@H]3CCCN3C(=O)[C@@H](NC(=O)OC)C(C)C)[nH]2)ccc1-c1ccc(-c2cnc([C@@H]3CCCN3C(=O)[C@@H](NC(=O)OC)C(C)C)[nH]2)c(OCCOC)c1] |
| 52 | 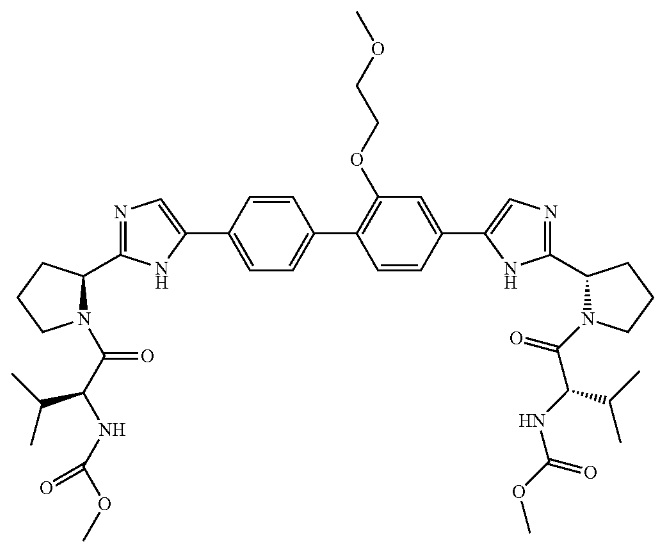 [SMILES: COCCOc1cc(-c2cnc([C@@H]3CCCN3C(=O)[C@@H](NC(=O)OC)C(C)C)[nH]2)ccc1-c1ccc(-c2cnc([C@@H]3CCCN3C(=O)[C@@H](NC(=O)OC)C(C)C)[nH]2)cc1] |
| 53 | 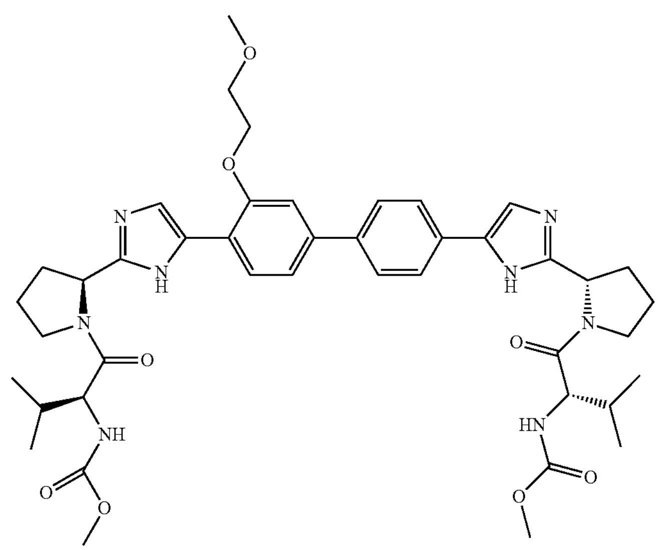 [SMILES: COCCOc1cc(-c2ccc(-c3cnc([C@@H]4CCCN4C(=O)[C@@H](NC(=O)OC)C(C)C)[nH]3)cc2)ccc1-c1cnc([C@@H]2CCCN2C(=O)[C@@H](NC(=O)OC)C(C)C)[nH]1] |

TABLE 2-continued
| Compound # | Structure |
| --- | --- |
| 54 | 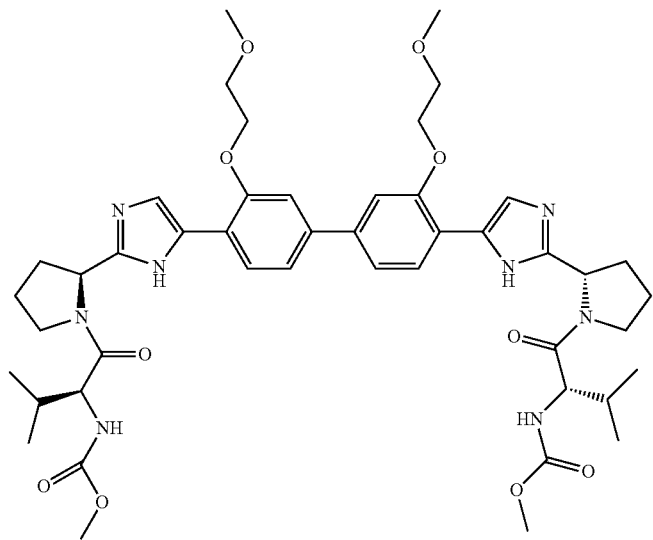 [SMILES: COCCOc1cc(-c2ccc(-c3cnc([C@@H]4CCCN4C(=O)[C@@H](NC(=O)OC)C(C)C)[nH]3)c(OCCOC)c2)ccc1-c1cnc([C@@H]2CCCN2C(=O)[C@@H](NC(=O)OC)C(C)C)[nH]1] |
| 55 | 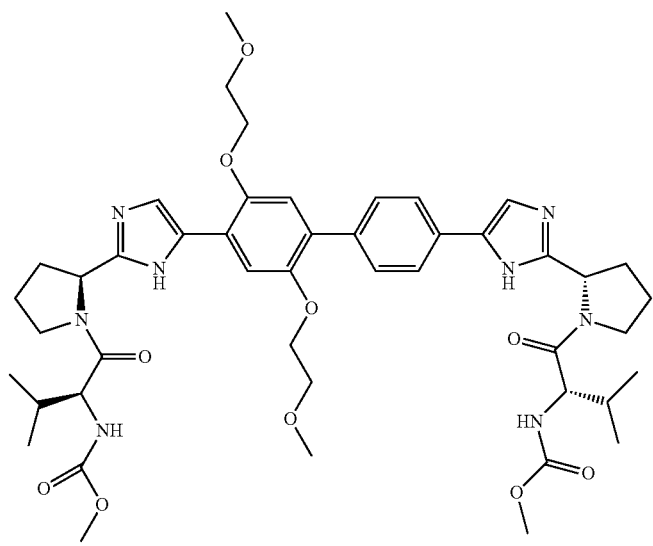 [SMILES: COCCOc1cc(-c2cnc([C@@H]3CCCN3C(=O)[C@@H](NC(=O)OC)C(C)C)[nH]2)c(OCCOC)cc1-c1ccc(-c2cnc([C@@H]3CCCN3C(=O)[C@@H](NC(=O)OC)C(C)C)[nH]2)cc1] |

TABLE 2-continued
| Compound # | Structure |
|---|---|
| 56 | 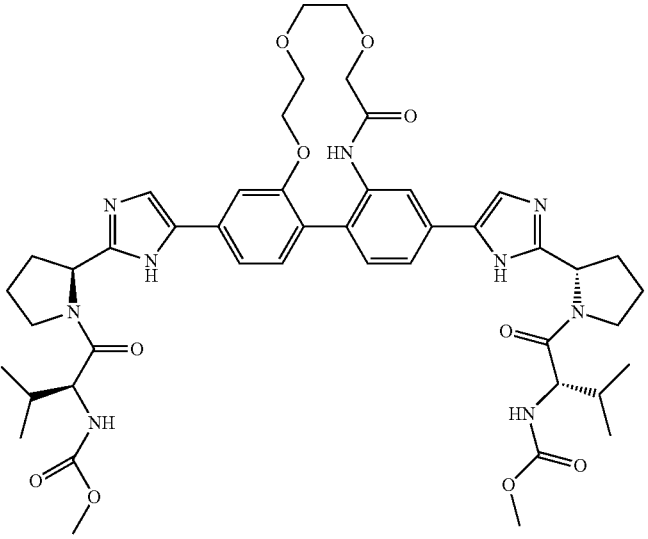 [SMILES: COC(=O)N[C@H](C(=O)N1CCC[C@H]1c1ncc(-c2ccc3c(c2)NC(=O)COCCOCCOc2cc(-c4cnc([C@@H]5CCCN5C(=O)[C@@H](NC(=O)OC)C(C)C)[nH]4)ccc2-3)[nH]1)C(C)C] |
| 57 | 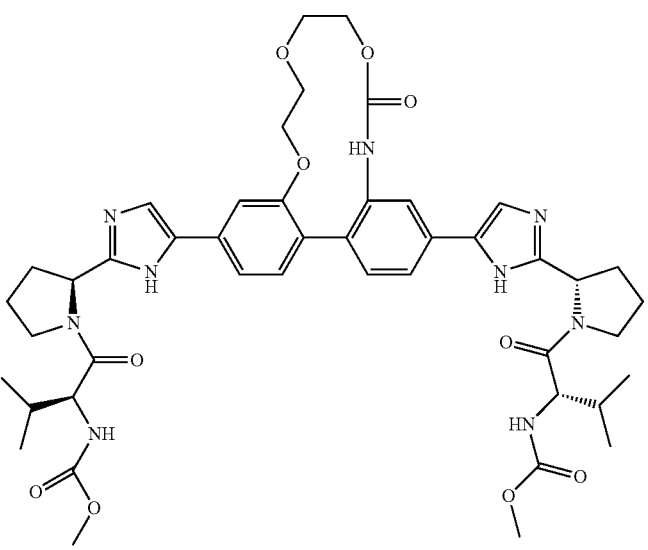 [SMILES: COC(=O)N[C@H](C(=O)N1CCC[C@H]1c1ncc(-c2ccc3c(c2)NC(=O)OCCOCCOc2cc(-c4cnc([C@@H]5CCCN5C(=O)[C@@H](NC(=O)OC)C(C)C)[nH]4)ccc2-3)[nH]1)C(C)C] |
| 58 | 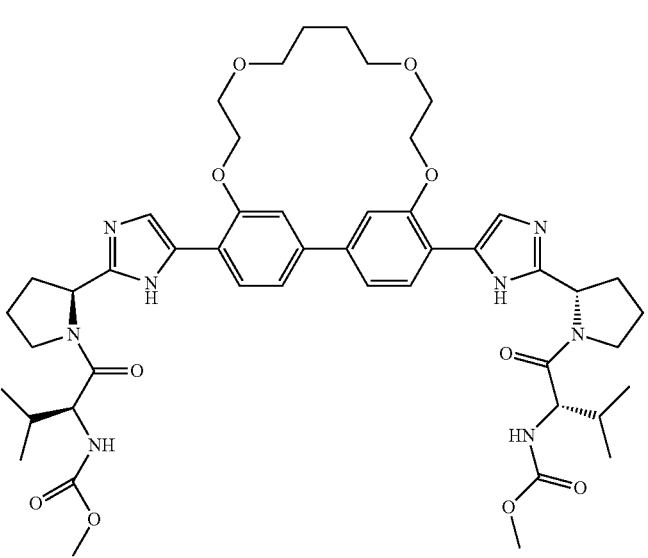 [SMILES: COC(=O)N[C@H](C(=O)N1CCC[C@H]1c1ncc(-c2ccc3cc2OCCOCCCCOCCOc2cc-3ccc2-c2cnc([C@@H]3CCCN3C(=O)[C@@H](NC(=O)OC)C(C)C)[nH]2)[nH]1)C(C)C] |

TABLE 2-continued

| Compound # | Structure |
| --- | --- |
| 59 | 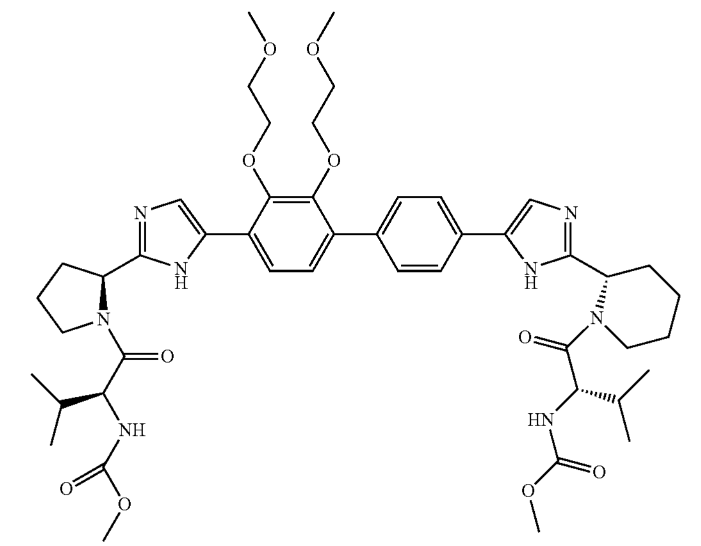 [SMILES: COCCOc1c(-c2ccc(-c3cnc([C@@H]4CCCCN4C(=O)[C@@H](NC(=O)OC)C(C)C)[nH]3)cc2)ccc(-c2cnc([C@@H]3CCCN3C(=O)[C@@H](NC(=O)OC)C(C)C)[nH]2)c1OCCOC] |
| 60 | 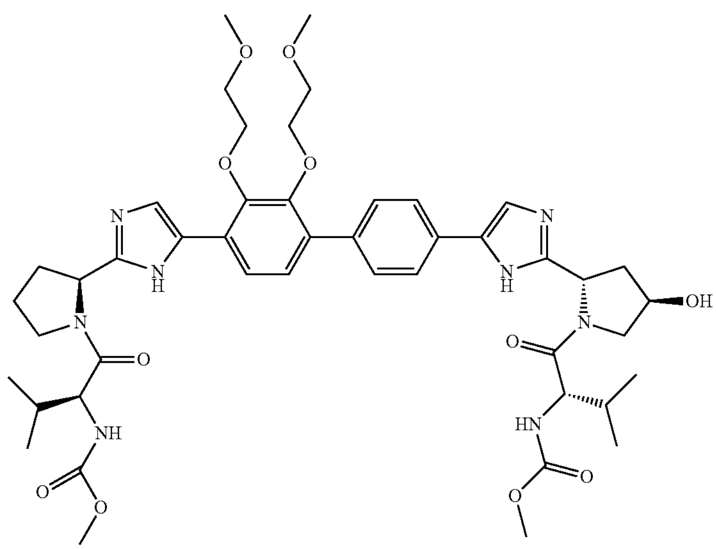 [SMILES: COCCOc1c(-c2ccc(-c3cnc([C@@H]4C[C@@H](O)CN4C(=O)[C@@H](NC(=O)OC)C(C)C)[nH]3)cc2)ccc(-c2cnc([C@@H]3CCCN3C(=O)[C@@H](NC(=O)OC)C(C)C)[nH]2)c1OCCOC] |

Pharmaceutical Compositions

A ninth aspect of the invention provides a pharmaceutical composition comprising the compounds of the invention. In a first embodiment, the pharmaceutical composition further comprises one or more pharmaceutically acceptable excipients or vehicles, and optionally other therapeutic and/or prophylactic ingredients. Such excipients are known to those of skill in the art. The compounds of the present invention include, without limitation, basic compounds such as free bases. A thorough discussion of pharmaceutically acceptable excipients and salts is available in Remington's Pharmaceutical Sciences, 18th Edition (Easton, Pa.: Mack Publishing Company, 1990).

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include an effective amount of the selected drug in combination with a pharmaceutically acceptable carrier and, in addition, may include other pharmaceutical agents, adjuvants, diluents, buffers, etc.

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers and optionally other therapeutic and/or prophylactic ingredients.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate and the like.

For oral administration, the composition will generally take the form of a tablet, capsule, a softgel capsule nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents and the like.

A tenth aspect of the invention provides use of the compounds of the invention in the manufacture of a medicament.

In a first embodiment of the tenth aspect the medicament is for the treatment of hepatitis C.

An eleventh aspect of the invention provides a method of treating hepatitis C comprising administering to a subject in need thereof, a therapeutically effective amount of a compound of the invention, optionally in a pharmaceutical composition. A pharmaceutically or therapeutically effective amount of the composition will be delivered to the subject. The precise effective amount will vary from subject to subject and will depend upon the species, age, the subject's size and health, the nature and extent of the condition being treated, recommendations of the treating physician, and the therapeutics or combination of therapeutics selected for administration. Thus, the effective amount for a given situation can be determined by routine experimentation. The subject may be administered as many doses as is required to reduce and/or alleviate the signs, symptoms or causes of the disorder in question, or bring about any other desired alteration of a biological system. One of ordinary skill in the art of treating such diseases will be able, without undue experimentation and in reliance upon personal knowledge and the disclosure of this application, to ascertain a therapeutically effective amount of the compounds of this invention for a given disease.

Combination Therapy

The compounds of the present invention and their isomeric forms and pharmaceutically acceptable salts thereof are useful in treating and preventing HCV infection alone or when used in combination with other compounds targeting viral or cellular elements or functions involved in the HCV lifecycle. Classes of compounds useful in the invention may include, without limitation, all classes of HCV antivirals. For combination therapies, mechanistic classes of agents that may be useful when combined with the compounds of the present invention include, for example, nucleoside and non-nucleoside inhibitors of the HCV polymerase, protease inhibitors, helicase inhibitors, NS4B inhibitors and medicinal agents that functionally inhibit the internal ribosomal entry site (IRES) and other medicaments that inhibit HCV cell attachment or virus entry, HCV RNA translation, HCV RNA transcription, replication or HCV maturation, assembly or virus release. Specific compounds in these classes and useful in the invention include, but are not limited to, macrocyclic, heterocyclic and linear HCV protease inhibitors such as telaprevir (VX-950), boceprevir (SCH-503034), narlaprevir (SCH-900518), ITMN-191 (R-7227), TMC-435350 (a.k.a. TMC-435), MK-7009, BI-201335, BI-2061 (ciluprevir), BMS-650032, ACH-1625, ACH-1095 (HCV NS4A protease co-factor inhibitor), VX-500, VX-813, PHX-1766, PHX2054, IDX-136, IDX-316, ABT-450 EP-013420 (and congeners) and VBY-376; the Nucleosidic HCV polymerase (replicase) inhibitors useful in the invention include, but are not limited to, R7128, PSI-7851, IDX-184, IDX-102, R1479, UNX-08189, PSI-6130, PSI-938 and PSI-879 and various other nucleoside and nucleotide analogs and HCV inhibitors including (but not limited to) those derived as 2'-C-methyl modified nucleos(t)ides, 4'-aza modified nucleos(t)ides, and 7'-deaza modified nucleos(t)ides. Non-nuclosidic HCV polymerase (replicase) inhibitors useful in the invention, include, but are not limited to, HCV-796, HCV-371, VCH-759, VCH-916, VCH-222, ANA-598, MK-3281, ABT-333, ABT-072, PF-00868554, BI-207127, GS-9190, A-837093, JKT-109, GL-59728 and GL-60667.

In addition, NS5A inhibitors of the present invention may be used in combination with cyclophyllin and immunophyllin antagonists (eg, without limitation, DEBIO compounds, NM-811 as well as cyclosporine and its derivatives), kinase inhibitors, inhibitors of heat shock proteins (e.g., HSP90 and HSP70), other immunomodulatory agents that may include, without limitation, interferons (-alpha, -beta, -omega, -gamma, -lambda or synthetic) such as Intron A™, Roferon-A™, Canferon-A300™, Advaferon™, Infergen™, Humoferon™, Sumiferon MP™, Alfaferone™, IFN-β™, Feron™ and the like; polyethylene glycol derivatized (pegylated) interferon compounds, such as PEG interferon-α-2a (Pegasys™), PEG interferon-α-2b (PEGIntron™), pegylated IFN-α-con1 and the like; long acting formulations and derivatizations of interferon compounds such as the albumin-fused interferon, Albuferon™, Locteron™ and the like; interferons with various types of controlled delivery systems (e.g. ITCA-638, omega-interferon delivered by the DUROS™ subcutaneous delivery system); compounds that stimulate the synthesis of interferon in cells, such as resiquimod and the like; interleukins; compounds that enhance the development of type 1 helper T cell response, such as SCV-07 and the like; TOLL-like receptor agonists such as CpG-10101 (actilon), isotorabine, ANA773 and the like; thymosin α-1; ANA-245 and ANA-246; histamine dihydrochloride; propagermanium; tetrachlorodecaoxide; ampligen; IMP-321; KRN-7000; antibodies, such as civacir, XTL-6865 and the like and prophylactic and therapeutic vaccines such as InnoVac C, HCV E1E2/MF59 and the like. In addition, any of the above-described methods involving administering an NS5A inhibitor, a Type I interferon receptor agonist (e.g., an IFN-α) and a Type II interferon receptor agonist (e.g., an IFN-γ) can be augmented by administration of an effective amount of a TNF-α antagonist. Exemplary, non-limiting TNF-α antagonists that are suitable for use in such combination therapies include ENBREL™, REMICADE™ and HUMIRA™.

In addition, NS5A inhibitors of the present invention may be used in combination with antiprotozoans and other antivirals thought to be effective in the treatment of HCV infection, such as, without limitation, the prodrug nitazoxanide. Nitazoxanide can be used as an agent in combination the compounds disclosed in this invention as well as in combination with other agents useful in treating HCV infection such as peginterferon alfa-2a and ribavarin (see, for example, Rossignol, J F and Keeffe, E B, *Future Microbiol.* 3:539-545, 2008).

NS5A inhibitors of the present invention may also be used with alternative forms of interferons and pegylated interferons, ribavirin or its analogs (e.g., tarabavarin, levoviron), microRNA, small interfering RNA compounds (e.g., SIRPLEX-140-N and the like), nucleotide or nucleoside analogs, immunoglobulins, hepatoprotectants, anti-inflammatory agents and other inhibitors of NS5A Inhibitors of other targets in the HCV lifecycle include NS3 helicase inhibitors; NS4A co-factor inhibitors; antisense oligonucleotide inhibitors, such as ISIS-14803, AVI-4065 and the like; vector-encoded short hairpin RNA (shRNA); HCV specific ribozymes such as heptazyme, RPI, 13919 and the like; entry inhibitors such as HepeX-C, HuMax-HepC and the like; alpha glucosidase inhibitors such as celgosivir, UT-231B and the like; KPE- 02003002 and BIVN 401 and IMPDH inhibitors. Other illustrative HCV inhibitor compounds include those disclosed in the following publications: U.S. Pat. No. 5,807,876; U.S. Pat. No. 6,498,178; U.S. Pat. No. 6,344,465; U.S. Pat. No. 6,054,472; WO97/40028; WO98/40381; WO00/56331, WO 02/04425; WO 03/007945; WO 03/010141; WO 03/000254; WO 01/32153; WO 00/06529; WO 00/18231; WO 00/10573; WO 00/13708; WO 01/85172; WO 03/037893; WO 03/037894; WO 03/037895; WO 02/100851; WO 02/100846; EP 1256628; WO 99/01582; WO 00/09543; WO02/18369; WO98/17679, WO00/056331; WO 98/22496; WO 99/07734; WO 05/073216, WO 05/073195 and WO 08/021,927.

Additionally, combinations of, for example, ribavirin and interferon, may be administered as multiple combination therapy with at least one of the compounds of the present invention. The present invention is not limited to the aforementioned classes or compounds and contemplates known and new compounds and combinations of biologically active agents (see, Strader, D. B., Wright, T., Thomas, D. L. and Seeff, L. B., *AASLD Practice Guidelines*. 1-22, 2009 and Manns, M. P., Foster, G. R., Rockstroh, J. K., Zeuzem, S., Zoulim, F. and Houghton, M., *Nature Reviews Drug Discovery*. 6:991-1000, 2007, Pawlotsky, J-M., Chevaliez, S, and McHutchinson, J. G., *Gastroenterology*. 132:179-1998, 2007, Lindenbach, B. D. and Rice, C. M., *Nature* 436:933-938, 2005, Klebl, B. M., Kurtenbach, A., Salassidis, K., Daub, H. and Herget, T., *Antiviral Chemistry & Chemotherapy*. 16:69-90, 2005, Beaulieu, P. L., *Current Opinion in Investigational Drugs*. 8:614-634, 2007, Kim, S-J., Kim, J-H., Kim, Y-G., Lim, H-S, and Oh, W-J., *The Journal of Biological Chemistry*. 48:50031-50041, 2004, Okamoto, T., Nishimura, Y., Ichimura, T., Suzuki, K., Miyamura, T., Suzuki, T., Moriishi, K. and Matsuura, Y., *The EMBO Journal*. 1-11, 2006, Soriano, V., Peters, M. G. and Zeuzem, S. *Clinical Infectious Diseases*. 48:313-320, 2009, Huang, Z., Murray, M. G. and Secrist, J. A., *Antiviral Research*. 71:351-362, 2006 and Neyts, J., *Antiviral Research*. 71:363-371, 2006, each of which is incorporated by reference in their entirety herein). It is intended that combination therapies of the present invention include any chemically compatible combination of a compound of this inventive group with other compounds of the inventive group or other compounds outside of the inventive group, as long as the combination does not eliminate the anti-viral activity of the compound of this inventive group or the anti-viral activity of the pharmaceutical composition itself Combination therapy can be sequential, that is treatment with one agent first and then a second agent (for example, where each treatment comprises a different compound of the invention or where one treatment comprises a compound of the invention and the other comprises one or more biologically active agents) or it can be treatment with both agents at the same time (concurrently). Sequential therapy can include a reasonable time after the completion of the first therapy before beginning the second therapy. Treatment with both agents at the same time can be in the same daily dose or in separate doses. Combination therapy need not be limited to two agents and may include three or more agents. The dosages for both concurrent and sequential combination therapy will depend on absorption, distribution, metabolism and excretion rates of the components of the combination therapy as well as other factors known to one of skill in the art. Dosage values will also vary with the severity of the condition to be alleviated. It is to be further understood that for any particular subject, specific dosage regimens and schedules may be adjusted over time according to the individual's need and the professional judgment of the person administering or supervising the administration of the combination therapy.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

We claim:
1. A compound having formula I:

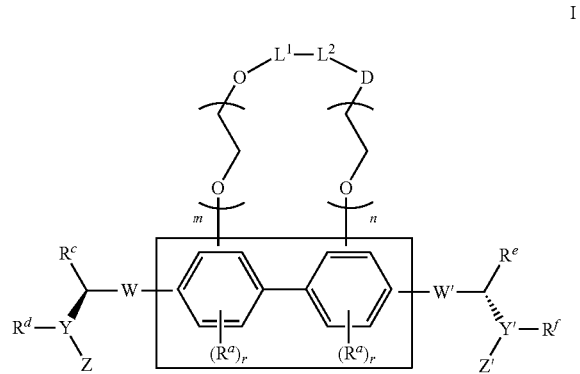

wherein:
L$^1$ and L$^2$ are either linked or not linked, when not linked, L$^1$ and L$^2$ are independently H or lower alkyl (containing 1 to 4 carbons) moieties;
when linked, L$^1$-L$^2$ are independently —CH$_2$C(O)—, —C(O)—, —(CH$_2$CH$_2$—O—CH$_2$CH$_2$)$_p$— wherein p is independently 1, 2 or 3, or lower alkyl (containing 1 to 4 carbons) moieties;
D is O;
m and n are independently 0, 1, 2, 3 or 4 and m and n may not be both 0;
each R$^a$ is independently selected from the group consisting of —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino;
each r is independently 0, 1, 2 or 3;
W and W' are each independently selected from the group consisting of

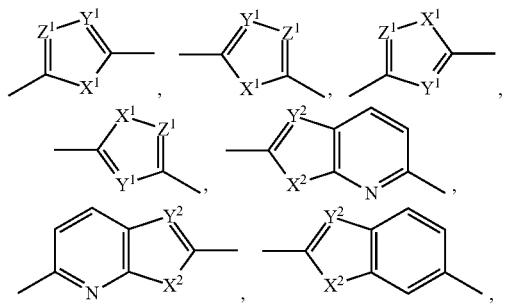

-continued

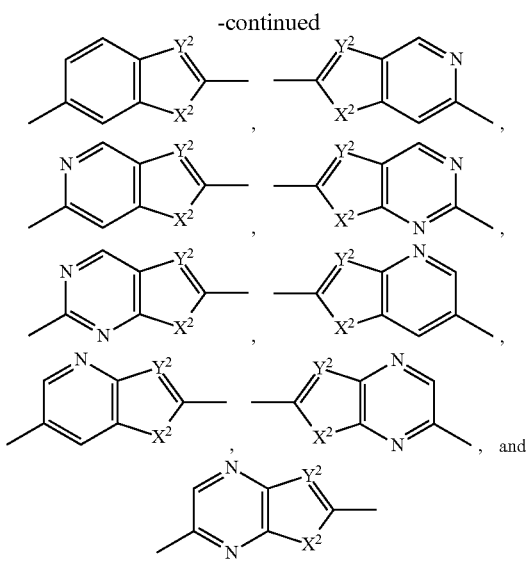

wherein:
X$^1$ is CH$_2$, NH, O or S,
Y$^1$, Y$^2$ and Z$^1$ are each independently CH or N,
X$^2$ is NH, O or S,
W and W' are each independently optionally substituted with one or more substituents selected from the group consisting of —CN, —NO$_2$, halogen, C$_1$ to C$_{12}$ alkyl, C$_1$ to C$_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate, sulfonamide and amino, and
W and W' attached to the central biphenyl moiety can have the following substitution patterns:

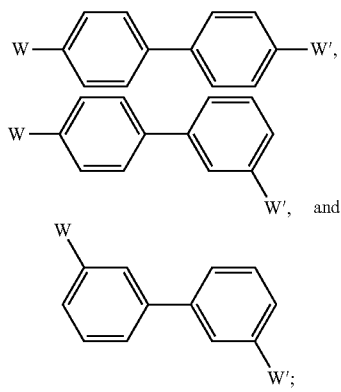

wherein,
the biphenyl moiety can be substituted with 0-4 nitrogen atom(s); and
each R$^c$, R$^d$, R$^e$ and R$^f$ is independently selected from the group consisting of: hydrogen, C$_1$ to C$_8$ alkyl, C$_1$ to C$_8$ heteroalkyl, aralkyl and a 4- to 8-membered ring which may be cycloalkyl, heterocycle, heteroaryl or aryl, wherein,
each hetero atom, if present, is independently N, O or S,
each of R$^c$, R$^d$, R$^e$ and R$^f$ may optionally be substituted by C$_1$ to C$_8$ alkyl, C$_1$ to C$_8$ heteroalkyl, aralkyl, or a 4- to 8-membered ring which may be cycloalkyl, heterocycle, heteroaryl or aryl and wherein each heteroatom, if present, is independently N, O or S, R$^c$ and R$^d$ are optionally joined to form a 4- to 8-membered heterocycle which is optionally fused to another 3- to 5-membered heterocycle or heteroaryl ring, and
R$^e$ and R$^f$ are optionally joined to form a 4- to 8-membered heterocycle which is optionally fused to another 3- to 5-membered heterocycle or heteroaryl ring;
Y and Y' are each independently carbon or nitrogen; and
Z and Z' are independently selected from the group consisting of hydrogen, C$_1$ to C$_8$ alkyl, C$_1$ to C$_8$ heteroalkyl, cycloalkyl, heterocycle, aryl, heteroaryl, aralkyl, 1-3 amino acids, —[U—(CR$^4$$_2$)$_t$—NR$^5$—C(R$^4$$_2$)$_t$]$_u$—U—(CR$^4$$_2$)$_t$—NR$^7$—(CR$^4$$_2$)$_t$—R$^8$, —U—(CR$^4$$_2$)$_t$—R$^8$, and —[U—(CR$^4$$_2$)$_t$—NR$^5$—(CR$^4$$_2$)$_t$]$_u$—U—(CR$^4$$_2$)$_t$—O—(CR$^4$$_2$)$_t$—R$^8$, wherein,
U is selected from the group consisting of —C(O)—, —C(S)— and —S(O)$_2$—,
each R$^4$, R$^5$ and R$^7$ is independently selected from the group consisting of hydrogen, C$_1$ to C$_8$ alkyl, C$_1$ to C$_8$ heteroalkyl, cycloalkyl, heterocycle, aryl, heteroaryl and aralkyl,
R$^8$ is selected from the group consisting of hydrogen, C$_1$ to C$_8$ alkyl, C$_1$ to C$_8$ heteroalkyl, cycloalkyl, heterocycle, aryl, heteroaryl, aralkyl, —C(O)—R$^{81}$, —C(S)—R$^{81}$, —C(O)—O—R$^{81}$, —C(O)—N—R$^{81}$$_2$, —S(O)$_2$—R$^{81}$ and —S(O)$_2$—N—R$^{81}$$_2$, wherein each R$^{81}$ is independently chosen from the group consisting of hydrogen, C$_1$ to C$_8$ alkyl, C$_1$ to C$_8$ heteroalkyl, cycloalkyl, heterocycle, aryl, heteroaryl and aralkyl,
optionally, R$^7$ and R$^8$ together form a 4-7 membered ring,
each t is independently 0, 1, 2, 3, or 4, and
u is 0, 1, or 2.

2. The compound of claim 1 wherein one or both of W and W' are selected from the group consisting of

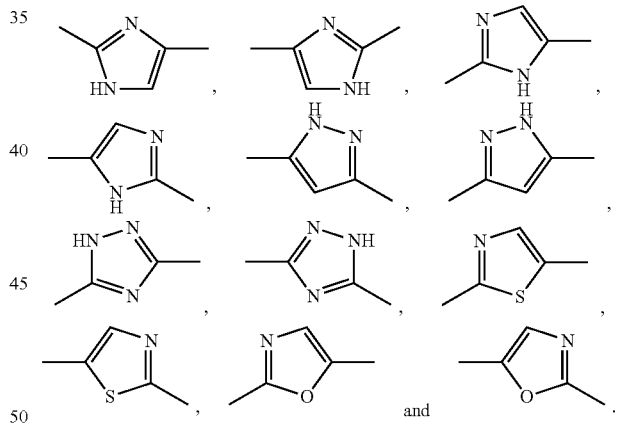

3. The compound of claim 1 wherein R$^c$ and R$^d$ are joined and form a heterocyclic fused ring system selected from the group consisting of:

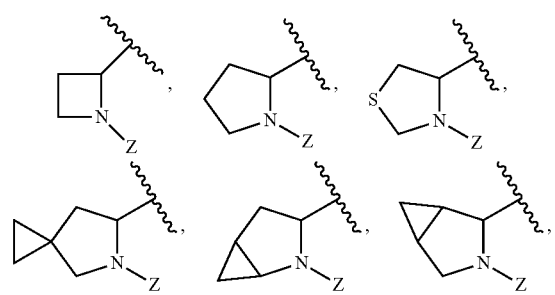

-continued

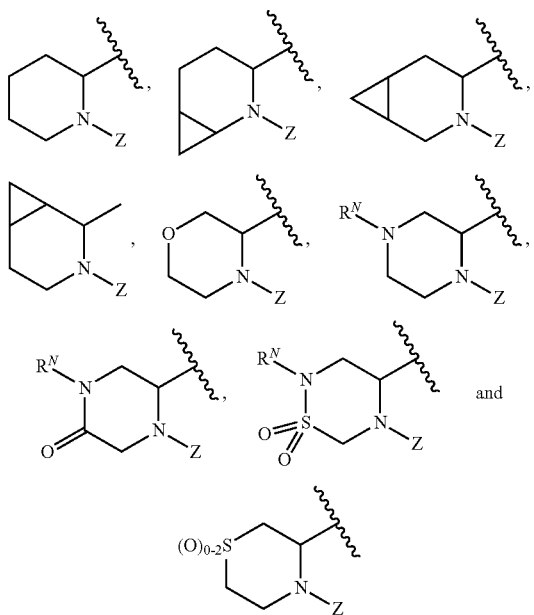

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

4. The compound of claim 1 wherein $R^e$ and $R^f$ are joined and form a heterocyclic fused ring system selected from the group consisting of:

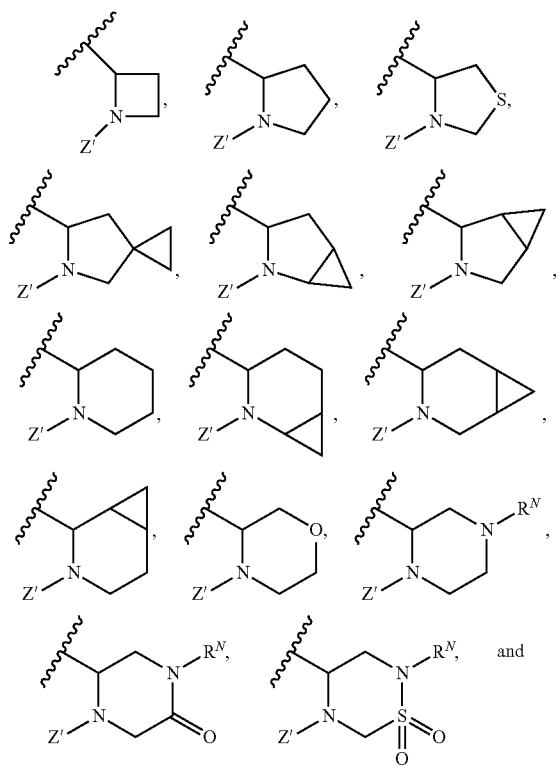

-continued

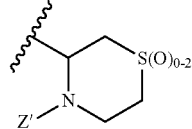

wherein $R^N$ is selected from the group consisting of hydrogen, —OH, $C_1$ to $C_{12}$ alkyl, $C_1$ to $C_{12}$ heteroalkyl, cycloalkyl, heterocycle, aryl, heteroaryl, aralkyl, alkoxy, alkoxycarbonyl, alkanoyl, carbamoyl, substituted sulfonyl, sulfonate and sulfonamide.

5. The compound of claim 1 having formula IIIa:

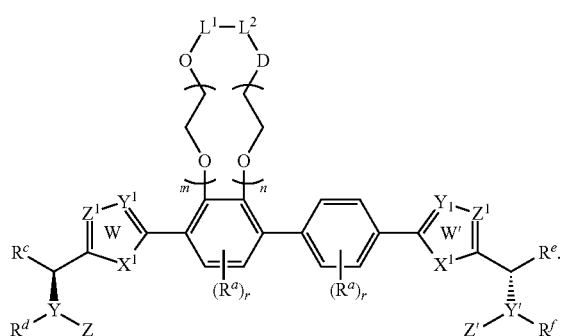

IIIa

6. The compound of claim 1 having formula IIIb:

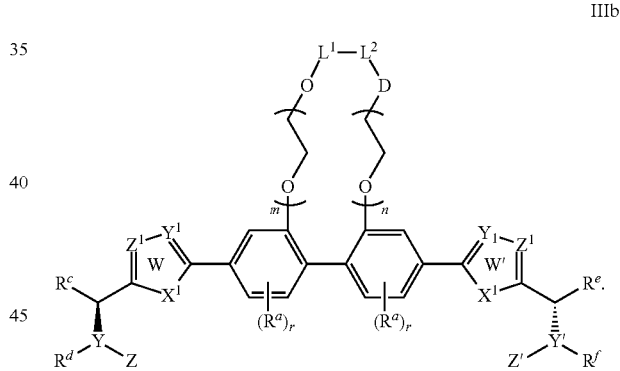

IIIb

7. The compound of claim 1 having formula IIIc:

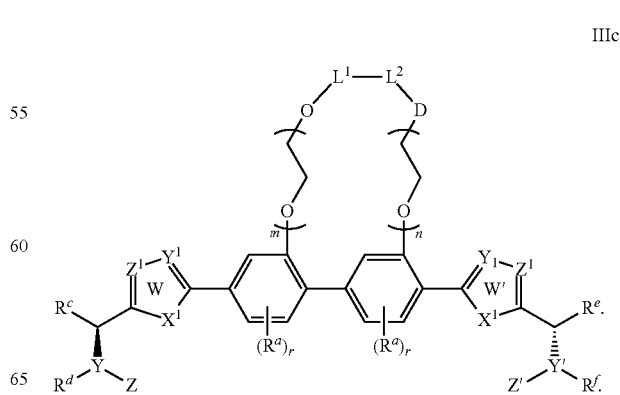

IIIc

8. The compound of claim 1 having formula IIId:

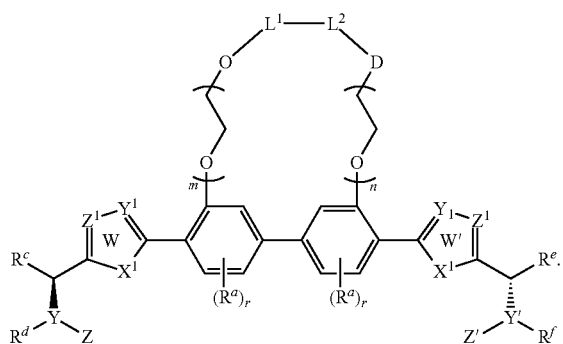

IIId

9. The compound of claim 1 wherein one or both of $X^1$ are —NH—.

10. The compound of claim 1 wherein one or both of $Z^1$ is —N—.

11. The compound of claim 1 wherein Z and Z' are each 1-3 amino acids.

12. The compound of claim 1 wherein one or both of Z and Z' are —C(O)—$(CR^4{}_2)_t$—$NR^7$—$(CR^4{}_2)_t$—$R^8$.

13. The compound of claim 1 wherein one or both of Z and Z' are —C(O)—$(CR^4{}_2)_n$—$NR^7$—C(O)—O—$R^{81}$.

14. The compound of claim 1 wherein one or both of Z and Z' are —C(O)—$(CR^4{}_2)_t$—$R^8$.

15. The compound of claim 1 wherein one or both of Z and Z' are —C(O)—$(CR^4{}_2)_t$—O—$(CR^4{}_2)_t$—$R^8$.

16. A pharmaceutical composition comprising any one the compounds of the claim 1.

17. A method of treating hepatitis C comprising administering to a subject in need thereof, a therapeutically effective amount of a compound of any one of the compounds of claim 1.

* * * * *